United States Patent
Noorchashm et al.

(10) Patent No.: US 8,362,224 B2
(45) Date of Patent: Jan. 29, 2013

(54) SCREENING FOR CD93 (C1QRP)-ASSOCIATED POLYMORPHISM(S) IN THE DIAGNOSIS, PREVENTION AND TREATMENT OF AUTOIMMUNE DISEASES

(75) Inventors: Hooman Noorchashm, Narberth, PA (US); Ali Naji, North Wales, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 315 days.

(21) Appl. No.: 12/520,515

(22) PCT Filed: Dec. 19, 2007

(86) PCT No.: PCT/US2007/025832
§ 371 (c)(1),
(2), (4) Date: Dec. 30, 2009

(87) PCT Pub. No.: WO2008/082519
PCT Pub. Date: Jul. 10, 2008

(65) Prior Publication Data
US 2011/0014608 A1     Jan. 20, 2011

Related U.S. Application Data

(60) Provisional application No. 60/875,556, filed on Dec. 19, 2006, provisional application No. 60/905,573, filed on Mar. 8, 2007.

(51) Int. Cl.
C12N 5/12       (2006.01)
C12N 15/63      (2006.01)
C07H 21/04      (2006.01)
C07K 14/705     (2006.01)

(52) U.S. Cl. .................... 536/23.5; 435/320.1; 530/395

(58) Field of Classification Search .................. None
See application file for complete search history.

(56) References Cited

FOREIGN PATENT DOCUMENTS
WO   WO-2004074320 A2 *  9/2004

OTHER PUBLICATIONS

Harhausen et al. CD93/AA4.1: a novel regulator of inflammation in murine focal cerebral ischemia. J Immunol. Jun. 1, 2010;184(11):6407-17. Epub May 3, 2010.*

* cited by examiner

*Primary Examiner* — David Romeo
(74) *Attorney, Agent, or Firm* — Mark S. Cohen; Pearl Cohen Zedek Latzer, LLP

(57) ABSTRACT

This invention is directed to a marker gene for autoimmune disease. Specifically, the invention is directed to the use of a polymorph of CD93 in methods and compositions for the detection, prognosis and therapy of Type I Diabetes and systemic lupus erythematosus (SLE).

4 Claims, 17 Drawing Sheets

```
C57BL/6 (B6): TGGGGCAGCTCAGGCCCCACTCTGTGTCAGCCCCCAAGTTTGGTTGCAGTTTGCAGTTTGCTTCGAGGATTGCTTCGAAGGTGGC
BALB/c:      TGGGGCAGCTCAGGCCCCACTCTGTGTCAGCCCCCAAGTTTGGTTGCAGTTTGCAGTTTGCAGGATTGCTTCGAAGGTGGC
NOD:         TGGGGCAGCTCAGGCCCCACTCTGTGTCAGCCCCCAAGTTTGGTTGCAGTTTGCACAACGGGGGCTGCCAGCAGGATTGCTTCGAAGGTGGC
NZB/W F1:    TGGGGCAGCTCAGGCCCCACTCTGTGTCAGCCCCCAAGTTTGGTTGCAGTTTGCACAACGGGGGCTGCCAGCAGGATTGCTTCGAAGGTGGC
MRL/MpJ+/+:  TGGGGCAGCTCAGGCCCCACTCTGTGTCAGCCCCCAAGTTTGGTTGCAGTTTGCACAACGGGGGCTGCCAGCAGGATTGCTTCGAAGGTGGC
                                                            738                      790
```

*Figure. 7A*

```
C57BL/6(B6): ASVANVACGDEAKSETHYFLCNEKTPGIFHWGSSGPLCVSPKFGCSFNNGGCQQDCFEGGDGSFRCGCRPGFRLLDDLVTCASRNPCSSNPCT
BALB/c:      ASVANVACGDEAKSETHYFLCNEKTPGIFHWGSSGPLCVSPKFGCSFNNGGCQQDCFEGGDGSFRCGCRPGFRLLDDLVTCASRNPCSSNPCT
NOD:         ASVANVACGDEAKSETHYFLCNEKTPGIFHWGSSGPLCVSPKFGCSFHNGGCQQDCFEGGDGSFRCGCRPGFRLLDDLVTCASRNPCSSNPCT
NZB/W F1:    ASVANVACGDEAKSETHYFLCNEKTPGIFHWGSSGPLCVSPKFGCSFHNGGCQQDCFEGGDGSFRCGCRPGFRLLDDLVTCASRNPCSSNPCT
MRL/MpJ+/+:  ASVANVACGDEAKSETHYFLCNEKTPGIFHWGSSGPLCVSPKFGCSFHNGGCQQDCFEGGDGSFRCGCRPGFRLLDDLVTCASRNPCSSNPCT
                  217                                    264                                    309
```

*Figure. 7B*

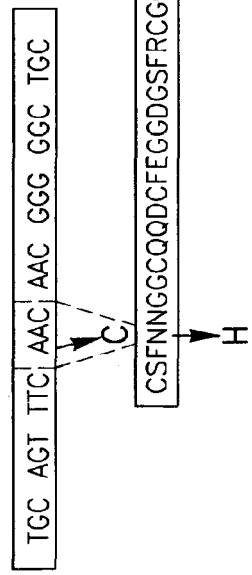

*Figure. 7C*

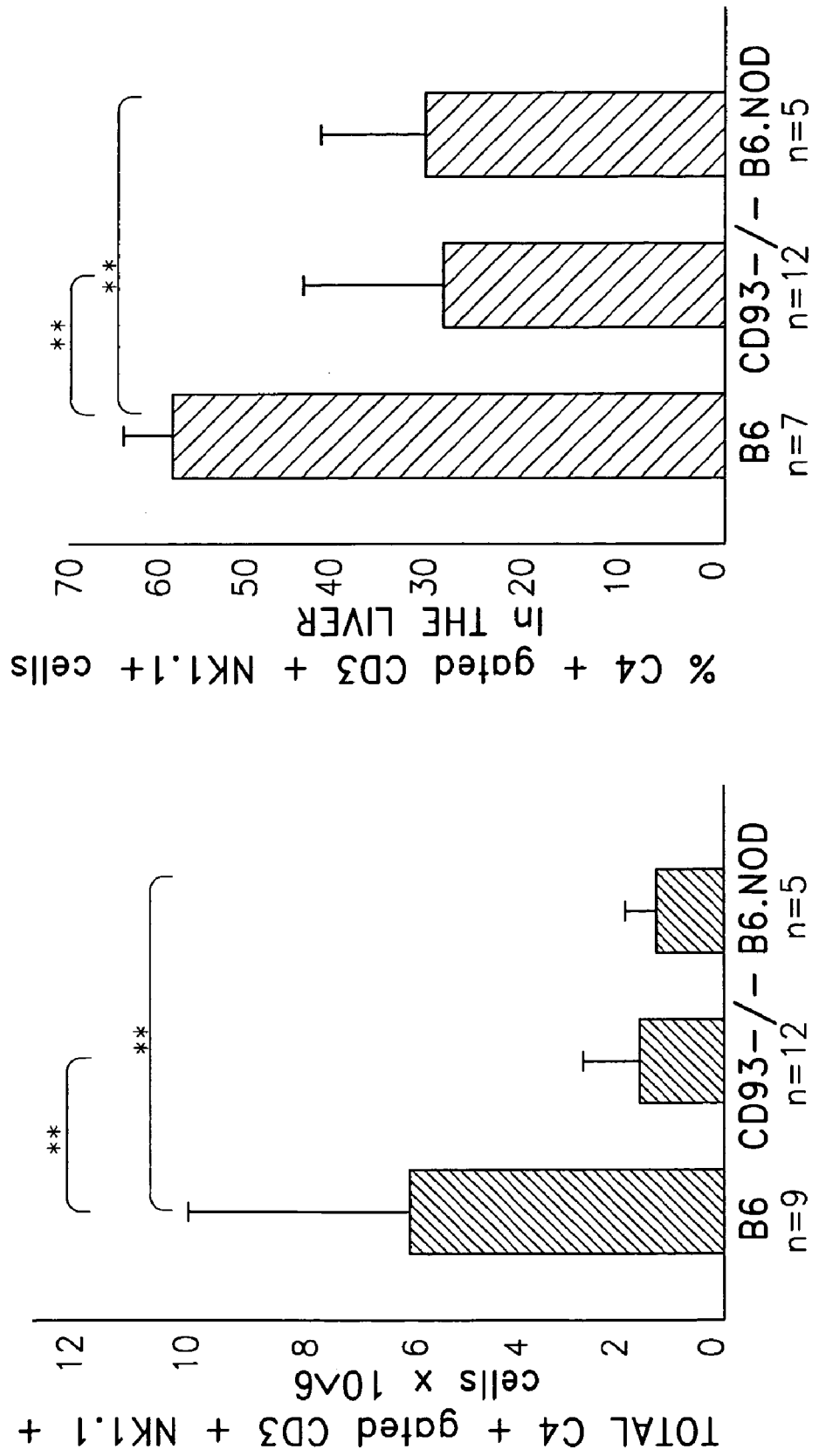

SEQUENCE LISTING

<160> NUMBER OF SEQ ID NOS: 10

<210> SEQ ID NO 1
<211> LENGTH: 1935
<212> TYPE: DNA
<213> ORGANISM: Mus musculus

<400> SEQUENCE: 1

```
atggccatct caactggttt gttcctgctg ctggggctcc ttggccagcc ctgggcaggg      60
gctgctgctg attcacaggc tgtggtgtgc gaggggactg cctgctatac agcccattgg     120
ggcaagctga gtgccgctga agcccagcat cgctgcaatg agaatggagg caatcttgcc     180
accgtgaaga gtgaggagga ggcccggcat gttcagcaag ccctgactca gctcctgaag     240
accaaggcac ccttggaagc aaagatgggc aaattctgga tcgggctcca gcgagagaag     300
ggcaactgta cgtaccatga tttgccaatg aggggcttca gctgggtggg tggtggagag     360
gacacagctt attcaaactg gtacaaagcc agcaagagct cctgtatctt taaacgctgt     420
gtgtccctca tactggacct gtccttgaca cctcacccca gccatctgcc caagtggcat     480
gagagtccct gtgggacccc cgaagctcca ggtaacagca ttgaaggttt cctgtgcaag     540
ttcaacttca aaggcatgtg taggccactg gcgctgggtg gtccagggcg ggtgacctat     600
accacccctt tccaggccac tacctcctct ctggaggctg tgccttttgc ctctgtagcc     660
aatgtagctt gtggggatga agctaagagt gaaacccact atttcctatg caatgaaaag     720
actccaggaa tatttcactg gggcagctca ggcccactct gtgtcagccc caagtttggt     780
tgcagtttca acaacggggg ctgccagcag gattgcttcg aaggtggcga tggctccttc     840
cgctgcggct gccggcctgg atttcgactg ctggatgatc tagtaacttg tgcctccagg     900 aaccctgca gctcaaaccc atgcacagga ggtggcatgt gccattctgt accactcagt     960
gaaaactaca cttgccgttg tcccagcggc taccagctgg actctagcca agtgcactgt    1020
gtggatatag atgagtgcca ggactccccc tgtgcccagg attgtgtcaa cactctaggg    1080
agcttccact gtgaatgttg ggttggttac caacccagtg gccccaagga agaggcctgt    1140
gaagatgtgg atgagtgtgc agctgccaac tcgccctgtg cccaaggctg catcaacact    1200
gatggctctt tctactgctc ctgtaaagag ggctatattg tgtctgggga agacagtacc    1260
cagtgtgagg atatagatga gtgttcggac gcaaggggca atccatgtga ttccctgtgc    1320
ttcaacacag atggttcctt caggtgtggc tgcccgccag gctgggagct ggctcccaat    1380
```

-continued

```
ggggtctttt gtagcagggg cactgtgttt tctgaactac cagccaggcc tccccaaaag   1440
gaagacaacg atgacagaaa ggagagtact atgcctccta ctgaaatgcc cagttctcct   1500
agtggctcta aggatgtctc caacagagca cagacaacag gtctcttcgt ccaatcagat   1560
attcccactg cctctgttcc actagaaata gaaatcccta gtgaagtatc tgatgtctgg   1620
ttcgagttgg gcacataccT ccccacgacc tccggccaca gcaagccgac acatgaagat   1680
tctgtgtctg cacacagtga caccgatggg cagaacctgc ttctgtttta catcctgggg   1740
acggtggtgg ccatctcact cttgctggtg ctggccctag ggattctcat ttatcataaa   1800
cggagagcca agaaggagga gataaaagag aagaagcctc agaatgcagc cgacagctat   1860
tcctgggttc cagagcgagc agagagccaa gccccggaga atcagtacag cccaacacca   1920
gggacagact gctga                                                    1935
```

<210> SEQ ID NO 2
<211> LENGTH: 644
<212> TYPE: PRT
<213> ORGANISM: Mus musculus

<400> SEQUENCE: 2

```
Met Ala Ile Ser Thr Gly Leu Phe Leu Leu Leu Gly Leu Leu Gly Gln
1               5                   10                  15

Pro Trp Ala Gly Ala Ala Asp Ser Gln Ala Val Val Cys Glu Gly
            20                  25                  30

Thr Ala Cys Tyr Thr Ala His Trp Gly Lys Leu Ser Ala Ala Glu Ala
        35                  40                  45

Gln His Arg Cys Asn Glu Asn Gly Gly Asn Leu Ala Thr Val Lys Ser
    50                  55                  60

Glu Glu Glu Ala Arg His Val Gln Gln Ala Leu Thr Gln Leu Leu Lys
65                  70                  75                  80

Thr Lys Ala Pro Leu Glu Ala Lys Met Gly Lys Phe Trp Ile Gly Leu
                85                  90                  95

Gln Arg Glu Lys Gly Asn Cys Thr Tyr His Asp Leu Pro Met Arg Gly
            100                 105                 110

Phe Ser Trp Val Gly Gly Glu Asp Thr Ala Tyr Ser Asn Trp Tyr
        115                 120                 125

Lys Ala Ser Lys Ser Ser Cys Ile Phe Lys Arg Cys Val Ser Leu Ile
    130                 135                 140

Leu Asp Leu Ser Leu Thr Pro His Pro Ser His Leu Pro Lys Trp His
145                 150                 155                 160

Glu Ser Pro Cys Gly Thr Pro Glu Ala Pro Gly Asn Ser Ile Glu Gly
                165                 170                 175

Phe Leu Cys Lys Phe Asn Phe Lys Gly Met Cys Arg Pro Leu Ala Leu
            180                 185                 190

Gly Gly Pro Gly Arg Val Thr Tyr Thr Thr Pro Phe Gln Ala Thr Thr
        195                 200                 205

Ser Ser Leu Glu Ala Val Pro Phe Ala Ser Val Ala Asn Val Ala Cys
    210                 215                 220

Gly Asp Glu Ala Lys Ser Glu Thr His Tyr Phe Leu Cys Asn Glu Lys
225                 230                 235                 240

Thr Pro Gly Ile Phe His Trp Gly Ser Ser Gly Pro Leu Cys Val Ser
                245                 250                 255

Pro Lys Phe Gly Cys Ser Phe Asn Asn Gly Gly Cys Gln Gln Asp Cys
            260                 265                 270

Phe Glu Gly Gly Asp Gly Ser Phe Arg Cys Gly Cys Arg Pro Gly Phe
```

```
                    275                 280                 285
Arg Leu Leu Asp Asp Leu Val Thr Cys Ala Ser Arg Asn Pro Cys Ser
290                 295                 300
Ser Asn Pro Cys Thr Gly Gly Met Cys His Ser Val Pro Leu Ser
305                 310             315                 320
Glu Asn Tyr Thr Cys Arg Cys Pro Ser Gly Tyr Gln Leu Asp Ser Ser
                325                 330                 335
Gln Val His Cys Val Asp Ile Asp Glu Cys Gln Asp Ser Pro Cys Ala
            340                 345                 350
Gln Asp Cys Val Asn Thr Leu Gly Ser Phe His Cys Glu Cys Trp Val
        355                 360                 365
Gly Tyr Gln Pro Ser Gly Pro Lys Glu Glu Ala Cys Glu Asp Val Asp
    370                 375                 380
Glu Cys Ala Ala Ala Asn Ser Pro Cys Ala Gln Gly Cys Ile Asn Thr
385                 390                 395                 400
Asp Gly Ser Phe Tyr Cys Ser Cys Lys Glu Gly Tyr Ile Val Ser Gly
                405                 410                 415
Glu Asp Ser Thr Gln Cys Glu Asp Ile Asp Glu Cys Ser Asp Ala Arg
            420                 425                 430
Gly Asn Pro Cys Asp Ser Leu Cys Phe Asn Thr Asp Gly Ser Phe Arg
        435                 440                 445
Cys Gly Cys Pro Pro Gly Trp Glu Leu Ala Pro Asn Gly Val Phe Cys
    450                 455                 460
Ser Arg Gly Thr Val Phe Ser Glu Leu Pro Ala Arg Pro Pro Gln Lys
465                 470                 475                 480
Glu Asp Asn Asp Asp Arg Lys Glu Ser Thr Met Pro Pro Thr Glu Met
                485                 490                 495
Pro Ser Ser Pro Ser Gly Ser Lys Asp Val Ser Asn Arg Ala Gln Thr
            500                 505                 510
Thr Gly Leu Phe Val Gln Ser Asp Ile Pro Thr Ala Ser Val Pro Leu
        515                 520                 525
Glu Ile Glu Ile Pro Ser Glu Val Ser Asp Val Trp Phe Glu Leu Gly
    530                 535                 540
Thr Tyr Leu Pro Thr Thr Ser His Ser Lys Pro Thr His Glu Asp
545                 550                 555                 560
Ser Val Ser Ala His Ser Asp Thr Asp Gly Gln Asn Leu Leu Phe
                565                 570                 575
Tyr Ile Leu Gly Thr Val Val Ala Ile Ser Leu Leu Val Leu Ala
            580                 585                 590
Leu Gly Ile Leu Ile Tyr His Lys Arg Arg Ala Lys Lys Glu Glu Ile
        595                 600                 605
Lys Glu Lys Lys Pro Gln Asn Ala Ala Asp Ser Tyr Ser Trp Val Pro
    610                 615                 620
Glu Arg Ala Glu Ser Gln Ala Pro Glu Asn Gln Tyr Ser Pro Thr Pro
625                 630                 635                 640
Gly Thr Asp Cys
```

<210> SEQ ID NO 3
<211> LENGTH: 1935
<212> TYPE: DNA
<213> ORGANISM: Mus musculus

<400> SEQUENCE: 3
atggccatct caactggttt gttcctgctg ctggggctcc ttggccagcc ctgggcaggg    60

-continued

```
gctgctgctg attcacaggc tgtggtgtgc gaggggactg cctgctatac agcccattgg    120
ggcaagctga gtgccgctga agcccagcat cgctgcaatg agaatggagg caatcttgcc    180
accgtgaaga gtgaggagga ggcccggcat gttcagcaag ccctgactca gctcctgaag    240
accaaggcac ccttggaagc aaagatgggc aaattctgga tcgggctcca gcgagagaag    300
ggcaactgta cgtaccatga tttgccaatg aggggcttca gctgggtggg tggtggagag    360
gacacagctt attcaaactg gtacaaagcc agcaagagct cctgtatctt aaacgctgt     420
gtgtccctca tactggacct gtccttgaca cctcacccca gccatctgcc caagtggcat    480
gagagtccct gtgggacccc cgaagctcca ggtaacagca ttgaaggttt cctgtgcaag    540
ttcaacttca aaggcatgtg taggccactg gcgctgggtg gtccagggcg ggtgacctat    600
accacccctt tccaggccac tacctcctct ctggaggctg tgccttttgc ctctgtagcc    660
aatgtagctt gtggggatga agctaagagt gaaacccact atttcctatg caatgaaaag    720
actccaggaa tatttcactg gggcagctca ggcccactct gtgtcagccc aagtttggt     780
tgcagtttcc acaacggggg ctgccagcag gattgcttcg aaggtggcga tggctccttc    840
cgctgcggct gccggcctgg atttcgactg ctggatgatc tagtaacttg tgcctccagg    900
aaccctgca gctcaaaccc atgcacagga ggtggcatgt gccattctgt accactcagt     960
gaaaactaca cttgccgttg tcccagcggc taccagctgg actctagcca agtgcactgt    1020
gtggatatag atgagtgcca ggactccccc tgtgcccagg attgtgtcaa cactctaggg    1080
agcttccact gtgaatgttg ggttggttac caacccagtg gccccaagga agaggcctgt    1140
gaagatgtgg atgagtgtgc agctgccaac tcgccctgtg cccaaggctg catcaacact    1200
gatggctctt tctactgctc ctgtaaagag ggctatattg tgtctgggga agacagtacc    1260
cagtgtgagg atatagatga gtgttcggac gcaagggggca atccatgtga ttccctgtgc    1320
ttcaacacag atggttcctt caggtgtggc tgcccgccag gctgggagct ggctcccaat    1380
ggggtctttt gtagcagggg cactgtgttt tctgaactac cagccaggcc tccccaaaag    1440
gaagacaacg atgacagaaa ggagagtact atgcctccta ctgaaatgcc cagttctcct    1500
agtggctcta aggatgtctc caacagagca cagacaacag gtctcttcgt ccaatcagat    1560
attcccactg cctctgttcc actagaaata gaaatcccta gtgaagtatc tgatgtctgg    1620
ttcgagttgg gcacatacct ccccacgacc tccggccaca gcaagccgac acatgaagat    1680
tctgtgtctg cacacagtga caccgatggg cagaacctgc ttctgttta catcctgggg     1740
acggtggtgg ccatctcact cttgctggtg ctggcctag ggattctcat ttatcataaa     1800
cggagagcca agaaggagga gataaaagag aagaagcctc agaatgcagc cgacagctat    1860
tcctgggttc cagagcgagc agagagccaa gccccggaga atcagtacag cccaacacca    1920
gggacagact gctga                                                     1935
```

<210> SEQ ID NO 4
<211> LENGTH: 644
<212> TYPE: PRT
<213> ORGANISM: Mus musculus

<400> SEQUENCE: 4

```
Met Ala Ile Ser Thr Gly Leu Phe Leu Leu Gly Leu Leu Gly Gln
1               5                   10                  15

Pro Trp Ala Gly Ala Ala Ala Asp Ser Gln Ala Val Val Cys Glu Gly
            20                  25                  30

Thr Ala Cys Tyr Thr Ala His Trp Gly Lys Leu Ser Ala Ala Glu Ala
        35                  40                  45
```

```
Gln His Arg Cys Asn Glu Asn Gly Gly Asn Leu Ala Thr Val Lys Ser
    50                  55                  60
Glu Glu Glu Ala Arg His Val Gln Gln Ala Leu Thr Gln Leu Leu Lys
65                  70                  75                  80
Thr Lys Ala Pro Leu Glu Ala Lys Met Gly Lys Phe Trp Ile Gly Leu
                85                  90                  95
Gln Arg Glu Lys Gly Asn Cys Thr Tyr His Asp Leu Pro Met Arg Gly
            100                 105                 110
Phe Ser Trp Val Gly Gly Gly Glu Asp Thr Ala Tyr Ser Asn Trp Tyr
        115                 120                 125
Lys Ala Ser Lys Ser Ser Cys Ile Phe Lys Arg Cys Val Ser Leu Ile
    130                 135                 140
Leu Asp Leu Ser Leu Thr Pro His Pro Ser His Leu Pro Lys Trp His
145                 150                 155                 160
Glu Ser Pro Cys Gly Thr Pro Glu Ala Pro Gly Asn Ser Ile Glu Gly
                165                 170                 175
Phe Leu Cys Lys Phe Asn Phe Lys Gly Met Cys Arg Pro Leu Ala Leu
            180                 185                 190
Gly Gly Pro Gly Arg Val Thr Tyr Thr Thr Pro Phe Gln Ala Thr Thr
        195                 200                 205
Ser Ser Leu Glu Ala Val Pro Phe Ala Ser Val Ala Asn Val Ala Cys
    210                 215                 220
Gly Asp Glu Ala Lys Ser Glu Thr His Tyr Phe Leu Cys Asn Glu Lys
225                 230                 235                 240
Thr Pro Gly Ile Phe His Trp Gly Ser Ser Gly Pro Leu Cys Val Ser
                245                 250                 255
Pro Lys Phe Gly Cys Ser Phe His Asn Gly Gly Cys Gln Gln Asp Cys
            260                 265                 270
Phe Glu Gly Gly Asp Gly Ser Phe Arg Cys Gly Cys Arg Pro Gly Phe
        275                 280                 285
Arg Leu Leu Asp Asp Leu Val Thr Cys Ala Ser Arg Asn Pro Cys Ser
    290                 295                 300
Ser Asn Pro Cys Thr Gly Gly Gly Met Cys His Ser Val Pro Leu Ser
305                 310                 315                 320
Glu Asn Tyr Thr Cys Arg Cys Pro Ser Gly Tyr Gln Leu Asp Ser Ser
                325                 330                 335
Gln Val His Cys Val Asp Ile Asp Glu Cys Gln Asp Ser Pro Cys Ala
            340                 345                 350
Gln Asp Cys Val Asn Thr Leu Gly Ser Phe His Cys Glu Cys Trp Val
        355                 360                 365
Gly Tyr Gln Pro Ser Gly Pro Lys Glu Glu Ala Cys Glu Asp Val Asp
    370                 375                 380
Glu Cys Ala Ala Ala Asn Ser Pro Cys Ala Gln Gly Cys Ile Asn Thr
385                 390                 395                 400
Asp Gly Ser Phe Tyr Cys Ser Cys Lys Glu Gly Tyr Ile Val Ser Gly
                405                 410                 415
Glu Asp Ser Thr Gln Cys Glu Asp Ile Asp Glu Cys Ser Asp Ala Arg
            420                 425                 430
Gly Asn Pro Cys Asp Ser Leu Cys Phe Asn Thr Asp Gly Ser Phe Arg
        435                 440                 445
Cys Gly Cys Pro Pro Gly Trp Glu Leu Ala Pro Asn Gly Val Phe Cys
    450                 455                 460
Ser Arg Gly Thr Val Phe Ser Glu Leu Pro Ala Arg Pro Pro Gln Lys
```

```
                465                 470                 475                 480
Glu Asp Asn Asp Arg Lys Glu Ser Thr Met Pro Pro Thr Glu Met
                        485                 490                 495
Pro Ser Ser Pro Ser Gly Ser Lys Asp Val Ser Asn Arg Ala Gln Thr
                500                 505                 510
Thr Gly Leu Phe Val Gln Ser Asp Ile Pro Thr Ala Ser Val Pro Leu
                515                 520                 525
Glu Ile Glu Ile Pro Ser Glu Val Ser Asp Val Trp Phe Glu Leu Gly
            530                 535                 540
Thr Tyr Leu Pro Thr Thr Ser Gly His Ser Lys Pro Thr His Glu Asp
545                 550                 555                 560
Ser Val Ser Ala His Ser Asp Thr Asp Gly Gln Asn Leu Leu Leu Phe
                565                 570                 575
Tyr Ile Leu Gly Thr Val Val Ala Ile Ser Leu Leu Val Leu Ala
                580                 585                 590
Leu Gly Ile Leu Ile Tyr His Lys Arg Arg Ala Lys Lys Glu Glu Ile
                595                 600                 605
Lys Glu Lys Lys Pro Gln Asn Ala Ala Asp Ser Tyr Ser Trp Val Pro
            610                 615                 620
Glu Arg Ala Glu Ser Gln Ala Pro Glu Asn Gln Tyr Ser Pro Thr Pro
625                 630                 635                 640
Gly Thr Asp Cys

<210> SEQ ID NO 5
<211> LENGTH: 1959
<212> TYPE: DNA
<213> ORGANISM: Mus musculus

<400> SEQUENCE: 5
atggccacct ccatgggcct gctgctgctg ctgctgctgc tcctgaccca gcccggggcg       60
gggacgggag ctgacacgga ggcggtggtc tgcgtgggga ccgcctgcta cacggcccac      120
tcgggcaagc tgagcgctgc cgaggcccag aaccactgca accagaacgg gggcaacctg      180
gccactgtga gagcaagga ggaggcccag cacgtccagc gagtactggc ccagctcctg      240
aggcgggagg cagccctgac ggcgaggatg agcaagttct ggattgggct ccagcgagag      300
aagggcaagt gcctggaccc tagtctgccg ctgaaggggt tcagctgggt gggcggggg       360
gaggacacgc cttactctaa ctggcacaag gagctccgga actcgtgcat ctccaagcgc      420
tgtgtgtctc tgctgctgga cctgtcccag ccgctccttc ccagccgcct ccccaagtgg      480
tctgagggcc cctgtgggag cccaggctcc cccggaagta acattgaggg cttcgtgtgc      540
aagttcagct tcaaaggcat gtgccggcct ctggccctgg ggggcccagg tcaggtgacc      600
tacaccaccc ccttccagac caccagttcc tccttggagg ctgtgccctt tgcctctgcg      660
gccaatgtag cctgtgggga aggtgacaag gacgagactc agagtcatta tttcctgtgc      720
aaggagaagg cccccgatgt gttcgactgg ggcagctcgg gccccctctg tgtcagcccc      780
aagtatggct gcaacttcaa caatgggggc tgccaccagg actgctttga agggggggat      840
ggctccttcc tctgcggctg ccgaccagga ttccggctgc tggatgacct ggtgacctgt      900
gcctctcgaa acccttgcag ctccagccca tgtcgtgggg gggccacgtg cgccctggga      960
ccccatggga aaaactacac gtgccgctgc cccaagggt accagctgga ctcgagtcag     1020
ctggactgtg tggacgtgga tgaatgccag gactccccct gtgccagga gtgtgtcaac     1080
accccctgggg gcttccgctg cgaatgctgg gttggctatg agccgggcgg tcctggagag     1140
```

```
ggggcctgtc aggatgtgga tgagtgtgct ctgggtcgct cgccttgcgc ccagggctgc    1200
accaacacag atggctcatt tcactgctcc tgtgaggagg gctacgtcct ggccggggag    1260
gacgggactc agtgccagga cgtggatgag tgtgtgggcc ggggggcccc cctctgcgac    1320
agcttgtgct tcaacacaca agggtccttc cactgtggct gcctgccagg ctgggtgctg    1380
gccccaaatg gggtctcttg caccatgggg cctgtgtctc tgggaccacc atctgggccc    1440
cccgatgagg aggacaaagg agagaaagaa gggagcaccg tgccccgcgc tgcaacagcc    1500
agtcccacaa ggggccccga gggcaccccc aaggctacac ccaccacaag tagaccttcg    1560
ctgtcatctg acgccccat cacatctgcc ccactcaaga tgctggcccc cagtgggtcc    1620
tcaggcgtct ggagggagcc cagcatccat cacgccacag ctgcctctgg ccccaggag    1680 cctgcaggtg gggactcctc cgtggccaca caaaacaacg atggcactga cgggcaaaag    1740
ctgcttttat tctacatcct aggcaccgtg gtggccatcc tactcctgct ggccctggct    1800
ctggggctac tggtctatcg caagcggaga gcgaagaggg aggagaagaa ggagaagaag    1860
ccccagaatg cggcagacag ttactcctgg gttccagagc gagctgagag cagggccatg    1920
gagaaccagt acagtccgac acctgggaca gactgctga                          1959
```

<210> SEQ ID NO 6
<211> LENGTH: 652
<212> TYPE: PRT
<213> ORGANISM: Mus musculus

<400> SEQUENCE: 6

```
Met Ala Thr Ser Met Gly Leu Leu Leu Leu Leu Leu Leu Leu Leu Thr
1               5                   10                  15

Gln Pro Gly Ala Gly Thr Gly Ala Asp Thr Glu Ala Val Val Cys Val
            20                  25                  30

Gly Thr Ala Cys Tyr Thr Ala His Ser Gly Lys Leu Ser Ala Ala Glu
        35                  40                  45

Ala Gln Asn His Cys Asn Gln Asn Gly Gly Asn Leu Ala Thr Val Lys
    50                  55                  60

Ser Lys Glu Glu Ala Gln His Val Gln Arg Val Leu Ala Gln Leu Leu
65                  70                  75                  80

Arg Arg Glu Ala Ala Leu Thr Ala Arg Met Ser Lys Phe Trp Ile Gly
                85                  90                  95

Leu Gln Arg Glu Lys Gly Lys Cys Leu Asp Pro Ser Leu Pro Leu Lys
            100                 105                 110

Gly Phe Ser Trp Val Gly Gly Glu Asp Thr Pro Tyr Ser Asn Trp
        115                 120                 125

His Lys Glu Leu Arg Asn Ser Cys Ile Ser Lys Arg Cys Val Ser Leu
    130                 135                 140

Leu Leu Asp Leu Ser Gln Pro Leu Leu Pro Ser Arg Leu Pro Lys Trp
145                 150                 155                 160

Ser Glu Gly Pro Cys Gly Ser Pro Gly Ser Pro Gly Ser Asn Ile Glu
                165                 170                 175

Gly Phe Val Cys Lys Phe Ser Phe Lys Gly Met Cys Arg Pro Leu Ala
            180                 185                 190

Leu Gly Gly Pro Gly Gln Val Thr Tyr Thr Thr Pro Phe Gln Thr Thr
        195                 200                 205

Ser Ser Ser Leu Glu Ala Val Pro Phe Ala Ser Ala Asn Val Ala
    210                 215                 220

Cys Gly Glu Gly Asp Lys Asp Glu Thr Gln Ser His Tyr Phe Leu Cys
225                 230                 235                 240
```

```
Lys Glu Lys Ala Pro Asp Val Phe Asp Trp Gly Ser Gly Pro Leu
                245                 250                 255

Cys Val Ser Pro Lys Tyr Gly Cys Asn Phe Asn Asn Gly Cys His
                260                 265                 270

Gln Asp Cys Phe Glu Gly Gly Asp Gly Ser Phe Leu Cys Gly Cys Arg
            275                 280                 285

Pro Gly Phe Arg Leu Leu Asp Asp Leu Val Thr Cys Ala Ser Arg Asn
    290                 295                 300

Pro Cys Ser Ser Pro Cys Arg Gly Ala Thr Cys Ala Leu Gly
305             310                 315                 320

Pro His Gly Lys Asn Tyr Thr Cys Arg Cys Pro Gln Gly Tyr Gln Leu
                325                 330                 335

Asp Ser Ser Gln Leu Asp Cys Val Asp Val Asp Glu Cys Gln Asp Ser
            340                 345                 350

Pro Cys Ala Gln Glu Cys Val Asn Thr Pro Gly Gly Phe Arg Cys Glu
            355                 360                 365

Cys Trp Val Gly Tyr Glu Pro Gly Gly Pro Gly Glu Gly Ala Cys Gln
    370                 375                 380

Asp Val Asp Glu Cys Ala Leu Gly Arg Ser Pro Cys Ala Gln Gly Cys
385                 390                 395                 400

Thr Asn Thr Asp Gly Ser Phe His Cys Ser Cys Glu Glu Gly Tyr Val
                405                 410                 415

Leu Ala Gly Glu Asp Gly Thr Gln Cys Gln Asp Val Asp Glu Cys Val
            420                 425                 430

Gly Pro Gly Gly Pro Leu Cys Asp Ser Leu Cys Phe Asn Thr Gln Gly
    435                 440                 445

Ser Phe His Cys Gly Cys Leu Pro Gly Trp Val Leu Ala Pro Asn Gly
    450                 455                 460

Val Ser Cys Thr Met Gly Pro Val Ser Leu Gly Pro Pro Ser Gly Pro
465                 470                 475                 480

Pro Asp Glu Glu Asp Lys Gly Glu Lys Glu Gly Ser Thr Val Pro Arg
                485                 490                 495

Ala Ala Thr Ala Ser Pro Thr Arg Gly Pro Glu Gly Thr Pro Lys Ala
            500                 505                 510

Thr Pro Thr Thr Ser Arg Pro Ser Leu Ser Ser Asp Ala Pro Ile Thr
            515                 520                 525

Ser Ala Pro Leu Lys Met Leu Ala Pro Ser Gly Ser Ser Gly Val Trp
530                 535                 540

Arg Glu Pro Ser Ile His His Ala Thr Ala Ala Ser Gly Pro Gln Glu
545                 550                 555                 560

Pro Ala Gly Gly Asp Ser Ser Val Ala Thr Gln Asn Asn Asp Gly Thr
                565                 570                 575

Asp Gly Gln Lys Leu Leu Leu Phe Tyr Ile Leu Gly Thr Val Val Ala
            580                 585                 590

Ile Leu Leu Leu Leu Ala Leu Ala Leu Gly Leu Leu Val Tyr Arg Lys
    595                 600                 605

Arg Arg Ala Lys Arg Glu Glu Lys Lys Glu Lys Lys Pro Gln Asn Ala
610                 615                 620

Ala Asp Ser Tyr Ser Trp Val Pro Glu Arg Ala Glu Ser Arg Ala Met
625                 630                 635                 640

Glu Asn Gln Tyr Ser Pro Thr Pro Gly Thr Asp Cys
                645                 650
```

<210> SEQ ID NO 7
<211> LENGTH: 1959
<212> TYPE: DNA
<213> ORGANISM: Mus musculus

<400> SEQUENCE: 7

| | | | | | |
|---|---|---|---|---|---|
| atggccacct | ccatgggcct | gctgctgctg | ctgctgctgc | tcctgaccca | gcccggggcg | 60 |
| gggacgggag | ctgacacgga | ggcggtggtc | tgcgtgggga | ccgcctgcta | cacggcccac | 120 |
| tcgggcaagc | tgagcgctgc | cgaggcccag | aaccactgca | accagaacgg | gggcaacctg | 180 |
| gccactgtga | agagcaagga | ggaggcccag | cacgtccagc | gagtactggc | ccagctcctg | 240 |
| aggcgggagg | cagccctgac | ggcgaggatg | agcaagttct | ggattgggct | ccagcgagag | 300 |
| aagggcaagt | gcctggaccc | tagtctgccg | ctgaagggct | tcagctgggt | gggcggggg | 360 |
| gaggacacgc | cttactctaa | ctggcacaag | gagctccgga | actcgtgcat | ctccaagcgc | 420 |
| tgtgtgtctc | tgctgctgga | cctgtcccag | ccgctccttc | ccagccgcct | ccccaagtgg | 480 |
| tctgagggcc | cctgtgggag | cccaggctcc | cccggaagta | acattgaggg | cttcgtgtgc | 540 |
| aagttcagct | tcaaaggcat | gtgccggcct | ctggccctgg | ggggcccagg | tcaggtgacc | 600 |
| tacaccaccc | ccttccagac | caccagttcc | tccttggagg | ctgtgccctt | tgcctctgcg | 660 |
| gccaatgtag | cctgtgggga | aggtgacaag | gacgagactc | agagtcatta | tttcctgtgc | 720 |
| aaggagaagg | cccccgatgt | gttcgactgg | ggcagctcgg | gcccctctg | tgtcagcccc | 780 |
| aagtatggct | gcaacttcaa | ccatgggggc | tgccaccagg | actgctttga | agggggggat | 840 |
| ggctccttcc | tctgcggctg | ccgaccagga | ttccggctgc | tggatgacct | ggtgacctgt | 900 |
| gcctctcgaa | acccttgcag | ctccagccca | tgtcgtgggg | gggccacgtg | cgccctggga | 960 |
| ccccatggga | aaaactacac | gtgccgctgc | ccccaagggt | accagctgga | ctcgagtcag | 1020 |
| ctggactgtg | tggacgtgga | tgaatgccag | gactcccct | gtgcccagga | gtgtgtcaac | 1080 |
| accctgggg | gcttccgctg | cgaatgctgg | gttggctatg | agccgggcgg | tcctggagag | 1140 |
| ggggcctgtc | aggatgtgga | tgagtgtgct | ctgggtcgct | cgccttgcgc | ccagggctgc | 1200 |
| accaacacag | atggctcatt | tcactgctcc | tgtgaggagg | ctacgtcct | ggccggggag | 1260 |
| gacgggactc | agtgccagga | cgtggatgag | tgtgtgggcc | cggggggccc | cctctgcgac | 1320 |
| agcttgtgct | tcaacacaca | agggtccttc | cactgtggct | gcctgccagg | ctgggtgctg | 1380 |
| gccccaaatg | gggtctcttg | caccatgggg | cctgtgtctc | tgggaccacc | atctgggccc | 1440 |
| cccgatgagg | aggacaaagg | agagaaagaa | gggagcaccg | tgccccgcgc | tgcaacagcc | 1500 |
| agtcccacaa | ggggccccga | gggcaccccc | aaggctacac | ccaccacaag | tagaccttcg | 1560 |
| ctgtcatctg | acgcccccat | cacatctgcc | ccactcaaga | tgctggcccc | cagtgggtcc | 1620 |
| tcaggcgtct | ggagggagcc | cagcatccat | cacgccacag | ctgcctctgg | ccccaggag | 1680 |
| cctgcaggtg | gggactcctc | cgtggccaca | caaaacaacg | atggcactga | cgggcaaaag | 1740 |
| ctgcttttat | tctacatcct | aggcaccgtg | gtggccatcc | tactcctgct | ggccctggct | 1800 |
| ctggggctac | tggtctatcg | caagcggaga | gcgaagaggg | aggagaagaa | ggagaagaag | 1860 |
| ccccagaatg | cggcagacag | ttactcctgg | gttccagagc | gagctgagag | cagggccatg | 1920 |
| gagaaccagt | acagtccgac | acctgggaca | gactgctga | | | 1959 |

<210> SEQ ID NO 8
<211> LENGTH: 652
<212> TYPE: PRT
<213> ORGANISM: Mus musculus

<400> SEQUENCE: 8

```
Met Ala Thr Ser Met Gly Leu Leu Leu Leu Leu Leu Leu Thr
1               5                   10                  15

Gln Pro Gly Ala Gly Thr Gly Ala Asp Thr Glu Ala Val Val Cys Val
            20                  25                  30

Gly Thr Ala Cys Tyr Thr Ala His Ser Gly Lys Leu Ser Ala Ala Glu
                35                  40                  45

Ala Gln Asn His Cys Asn Gln Asn Gly Gly Asn Leu Ala Thr Val Lys
            50                  55                  60

Ser Lys Glu Glu Ala Gln His Val Gln Arg Val Leu Ala Gln Leu Leu
65                  70                  75                  80

Arg Arg Glu Ala Ala Leu Thr Ala Arg Met Ser Lys Phe Trp Ile Gly
                85                  90                  95

Leu Gln Arg Glu Lys Gly Lys Cys Leu Asp Pro Ser Leu Pro Leu Lys
            100                 105                 110

Gly Phe Ser Trp Val Gly Gly Glu Asp Thr Pro Tyr Ser Asn Trp
            115                 120                 125

His Lys Glu Leu Arg Asn Ser Cys Ile Ser Lys Arg Cys Val Ser Leu
            130                 135                 140

Leu Leu Asp Leu Ser Gln Pro Leu Leu Pro Ser Arg Leu Pro Lys Trp
145                 150                 155                 160

Ser Glu Gly Pro Cys Gly Ser Pro Gly Ser Pro Gly Ser Asn Ile Glu
                165                 170                 175

Gly Phe Val Cys Lys Phe Ser Phe Lys Gly Met Cys Arg Pro Leu Ala
            180                 185                 190

Leu Gly Gly Pro Gly Gln Val Thr Tyr Thr Thr Pro Phe Gln Thr Thr
            195                 200                 205

Ser Ser Ser Leu Glu Ala Val Pro Phe Ala Ser Ala Asn Val Ala
            210                 215                 220

Cys Gly Glu Gly Asp Lys Asp Glu Thr Gln Ser His Tyr Phe Leu Cys
225                 230                 235                 240

Lys Glu Lys Ala Pro Asp Val Phe Asp Trp Gly Ser Ser Gly Pro Leu
                245                 250                 255

Cys Val Ser Pro Lys Tyr Gly Cys Asn Phe His Asn Gly Gly Cys His
            260                 265                 270

Gln Asp Cys Phe Glu Gly Gly Asp Gly Ser Phe Leu Cys Gly Cys Arg
            275                 280                 285

Pro Gly Phe Arg Leu Leu Asp Asp Leu Val Thr Cys Ala Ser Arg Asn
            290                 295                 300

Pro Cys Ser Ser Ser Pro Cys Arg Gly Gly Ala Thr Cys Ala Leu Gly
305                 310                 315                 320

Pro His Gly Lys Asn Tyr Thr Cys Arg Cys Pro Gln Gly Tyr Gln Leu
                325                 330                 335

Asp Ser Ser Gln Leu Asp Cys Val Asp Val Asp Glu Cys Gln Asp Ser
            340                 345                 350

Pro Cys Ala Gln Glu Cys Val Asn Thr Pro Gly Gly Phe Arg Cys Glu
            355                 360                 365

Cys Trp Val Gly Tyr Glu Pro Gly Gly Pro Gly Glu Gly Ala Cys Gln
            370                 375                 380

Asp Val Asp Glu Cys Ala Leu Gly Arg Ser Pro Cys Ala Gln Gly Cys
385                 390                 395                 400

Thr Asn Thr Asp Gly Ser Phe His Cys Ser Cys Glu Glu Gly Tyr Val
                405                 410                 415

Leu Ala Gly Glu Asp Gly Thr Gln Cys Gln Asp Val Asp Glu Cys Val
```

```
                    420             425             430
Gly Pro Gly Gly Pro Leu Cys Asp Ser Leu Cys Phe Asn Thr Gln Gly
            435                 440                 445

Ser Phe His Cys Gly Cys Leu Pro Gly Trp Val Leu Ala Pro Asn Gly
        450                 455                 460

Val Ser Cys Thr Met Gly Pro Val Ser Leu Gly Pro Pro Ser Gly Pro
465                 470                 475                 480

Pro Asp Glu Glu Asp Lys Gly Glu Lys Glu Gly Ser Thr Val Pro Arg
                485                 490                 495

Ala Ala Thr Ala Ser Pro Thr Arg Gly Pro Glu Gly Thr Pro Lys Ala
            500                 505                 510

Thr Pro Thr Thr Ser Arg Pro Ser Leu Ser Ser Asp Ala Pro Ile Thr
        515                 520                 525

Ser Ala Pro Leu Lys Met Leu Ala Pro Ser Gly Ser Ser Gly Val Trp
    530                 535                 540

Arg Glu Pro Ser Ile His His Ala Thr Ala Ala Ser Gly Pro Gln Glu
545                 550                 555                 560

Pro Ala Gly Gly Asp Ser Ser Val Ala Thr Gln Asn Asn Asp Gly Thr
                565                 570                 575

Asp Gly Gln Lys Leu Leu Leu Phe Tyr Ile Leu Gly Thr Val Val Ala
            580                 585                 590

Ile Leu Leu Leu Ala Leu Ala Leu Gly Leu Leu Val Tyr Arg Lys
        595                 600                 605

Arg Arg Ala Lys Arg Glu Glu Lys Lys Glu Lys Lys Pro Gln Asn Ala
    610                 615                 620

Ala Asp Ser Tyr Ser Trp Val Pro Glu Arg Ala Glu Ser Arg Ala Met
625                 630                 635                 640

Glu Asn Gln Tyr Ser Pro Thr Pro Gly Thr Asp Cys
                645                 650

<210> SEQ ID NO 9
<211> LENGTH: 20
<212> TYPE: DNA
<213> ORGANISM: Mus musculus

<400> SEQUENCE: 9
atggccatct caactggttt                                           20

<210> SEQ ID NO 10
<211> LENGTH: 20
<212> TYPE: DNA
<213> ORGANISM: Mus musculus

<400> SEQUENCE: 10
tcagcagtct gtccctggtg                                           20
```

SCREENING FOR CD93 (C1QRP)-ASSOCIATED POLYMORPHISM(S) IN THE DIAGNOSIS, PREVENTION AND TREATMENT OF AUTOIMMUNE DISEASES

CROSS REFERENCE TO RELATED APPLICATIONS

This application is a national stage application of PCT application PCT/US07/25832, filed Dec. 19, 2007 and claims priority to U.S. Provisional Patent Applications 60/875,556, filed Dec. 19, 2006 and 60/905,573, filed Mar. 8, 2007, which are incorporated herein by reference in their entirety.

FIELD OF INVENTION

The invention is directed to a marker gene for autoimmune disease. Specifically, the invention is directed to the use of a polymorph of CD93 in methods and compositions for the detection, prognosis and therapy of Type I Diabetes and systemic lupus erythematosus (SLE).

BACKGROUND OF THE INVENTION

Type I, or insulin-dependent, diabetes mellitus (also referred to herein as DM-I) is known to occur spontaneously in humans, rats and mice. There is a genetic susceptibility to DM-I associated with certain haplotypes of Class II antigens of the major histocompatability complex (MHC). The pathology of DM-I consists of the progressive inflammatory infiltration of pancreatic islets (i.e., insulitis) containing immunocytes targeted specifically to insulin-secreting β-cells. This pathology develops over an indeterminate period of time (months to years).

DM-I is a chronic disease that requires life-long treatment to prevent acute illness and to reduce the risk of long-term complications. Restrictive diets and daily insulin injections can be burdensome for patients, thus reducing compliance, and even with treatment complications such as cataracts, retinopathy, glaucoma, renal disease and circulatory disease are prevalent.

Systemic lupus erythematosus (SLE), is a chronic, inflammatory autoimmune disease characterized by the production of autoantibodies having specificity for a wide range of self-antigens. SLE autoantibodies mediate organ damage by directly binding to host tissues and by forming immune complexes that deposit in vascular tissues and activate immune cells. Organs targeted in SLE include the skin, kidneys, vasculature, joints, various blood elements, and the central nervous system (CNS). The severity of disease, the spectrum of clinical involvement, and the response to therapy vary widely among patients. This clinical heterogeneity makes it challenging to diagnose and manage lupus.

CD93 is expressed by endothelial cells, cells of myeloid lineage, platelets and early hematopoeitic stem cells, and is a lineage specific marker of early B cell developmental stages. Normally, CD93 is expressed at high levels on Pro-, Pre- and immature BM B cell progenitors, as well as, TR B cells in the periphery (FIG. 1). The CD93 gene is located at 84 cM on murine chromosome 2 and encodes a type I O-glycosylated transmembrane protein whose domain structure includes an amino-terminal C-type lectin domain, a tandem array of five EGF-like repeats, a single hydrophobic trans-membrane region, and a short cytoplasmic domain that contains a PDZ binding domain and a moesin interaction site. This domain structure bears a unique resemblance to the selectin-family of adhesion molecules. Additionally, the CD93 is subject to metalloprotease mediated ectodomain cleavage, or shedding, which is characteristic of several inflammatory mediators and adhesion molecules including TNF-α, TGF-α, TGF-β, EGF, CD44 and L-selectin. Despite its initial identification as a receptor for the C1q component of complement and demonstration of an in vivo kinetic defect in the clearance of apoptotic cells in CD93−/− mice, the in vivo function of the molecule is yet to be elucidated.

SUMMARY OF THE INVENTION

In one embodiment, provided herein is a marker gene for autoimmune disease. In another embodiment, provided herein is the use of a polymorph of CD93 in methods and compositions for the detection, prognosis and therapy of Type I Diabetes and systemic lupus erythematosus (SLE).

In one embodiment, the invention provides an isolated nucleic acid molecule encoding a mutated CD93 protein.

In another embodiment, the invention provides a method of providing a prognosis for a subject developing an autoimmune disease, comprising the steps of: Obtaining a biological sample from the subject; and Analyzing the sample for a mutation in a CD93 gene or its encoded protein, whereby if the CD93 gene or its encoded protein is mutated, the subject has an increased risk of developing an autoimmune disease.

In another embodiment, the invention provides a method of providing a prognosis for a subject developing Type I diabetes (DM(I)), comprising the steps of: Obtaining a biological sample from the subject; and Analyzing the sample for a mutation in a CD93 gene or its encoded protein, whereby if the CD93 gene or its encoded protein is mutated, the subject has an increased risk of developing an autoimmune disease In another embodiment, the invention provides a method of providing a prognosis for a subject developing systemic lupus erythematosus (SLE), comprising the steps of: Obtaining a biological sample from the subject; and Analyzing the sample for a mutation in a CD93 gene or its encoded protein, whereby if the CD93 gene or its encoded protein is mutated, the subject has an increased risk of developing systemic lupus erythematosus (SLE).

BRIEF DESCRIPTION OF THE DRAWINGS

The invention will be better understood from a reading of the following detailed description taken in conjunction with the drawings in which like reference designators are used to designate like elements, and in which:

FIG. 7 shows identification of a coding polymorphism in the first EGF-like domain of CD93 in NOD and NZB/W F1 mice. Panel A compares the coding sequences of that domain for B6, BALB/c, NOD, NZB/W F1, and MRL mice, respectively. For B6, BALB/c, and MRL mice nucleotides 738 to 828 of SEQ ID NO: 1 are shown, while for NOD and NZB/W F1 mice nucleotides 738 to 828 of SEQ ID NO: 3 are shown. Panel B compares the protein sequences in that region for B6, BALB/c, NOD, NZB/W F1, and MRL mice, respectively. For B6, BALB/c, and MRL mice residues 217 to 309 of SEQ ID NO: 2 are shown, while for NOD and NZB/W F1 mice nucleotides 217 to 309 of SEQ ID NO: 4 are shown. Panel C depicts the overall domain structure of CD93, as well as nucleotides 781 to 804 of SEQ ID NO: 1 and residues 261-297 of SEQ ID NO: 2;

DETAILED DESCRIPTION OF THE INVENTION

Figure 1A:
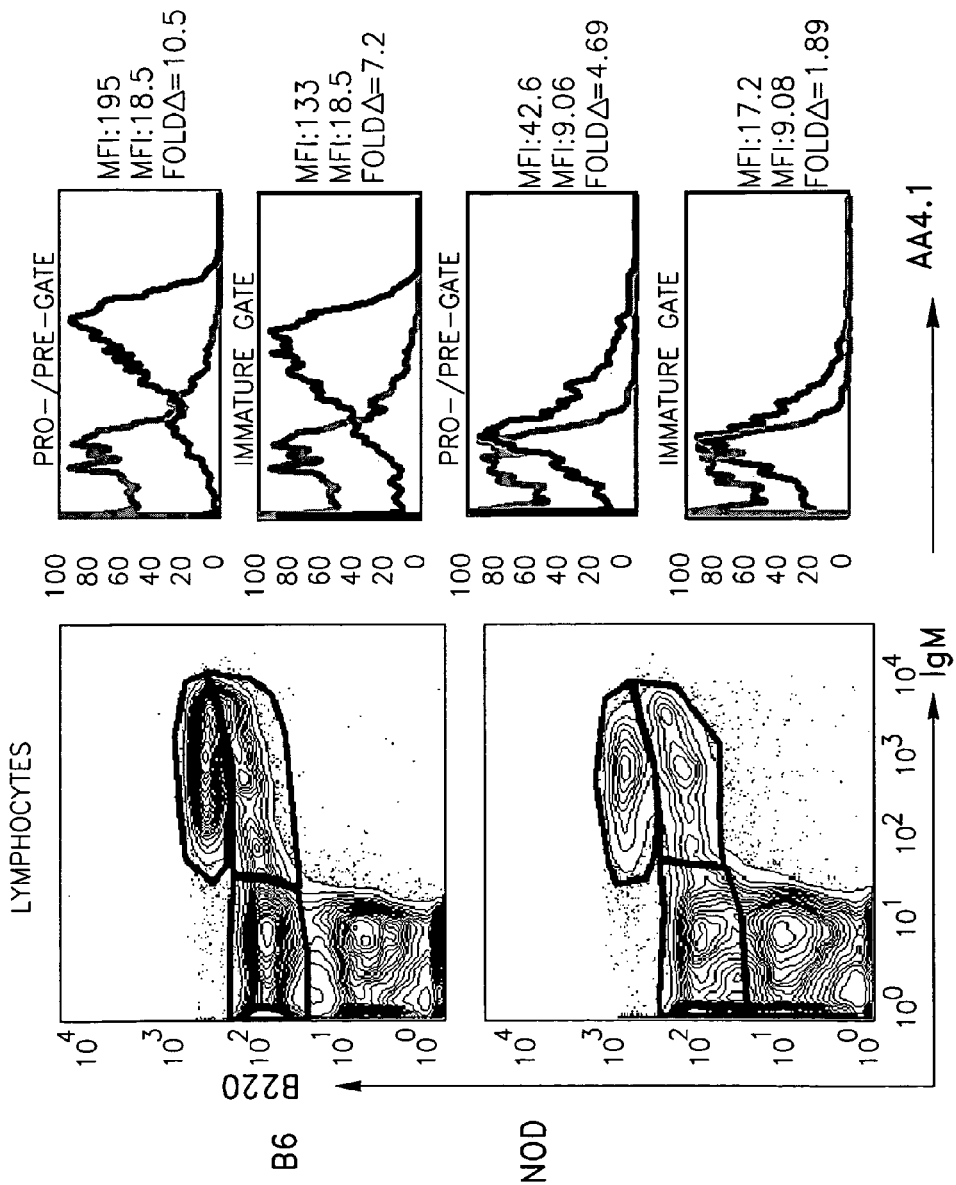
FIGS. 1A-C show CD93 expression on various B cell developmental subsets in BM and peripheral lymphoid organs.

In one embodiment, provided herein is a marker gene for autoimmune disease. In another embodiment, described herein, is the use of a polymorph of CD93 in methods and compositions for the detection, prognosis and therapy of Type I Diabetes and systemic lupus erythematosus (SLE).

This invention provides: isolated nucleic acid molecules and polypeptides comprising a mutated C1qRP sequence and methods for detecting C1qRP polymorphisms, identifying a subject having or at risk for developing auto-immune disease, and treating autoimmune disease. In another embodiment, the terms C1qRP and CD93 are interchangeable.

In one embodiment, described herein is aberrant expression of CD93 (interchangeable with AA4.1 in one embodiment, or C1qRp in another discrete embodiment) by NOD B cells in the Pro/Pre, immature and TR subsets. This defect is associated in one embodiment, with a coding polymorphism in the NOD CD93 allele. The CD93 locus maps to the Idd13 locus (84 cM on chromosome 2) in a region encoding a high degree of penetrance for diabetes progression in NOD mice. Interestingly, described herein, is this CD93 polymorphism in NZB/W F1 mice, to which the lupus susceptibility loci, Wbw1 and Nkt2, are tightly linked. In one embodiment, Idd13 and the Wbw1/Nkt2 loci are implicated in regulating NKT cell function. Consistent with the possibility that CD93 is an important autoimmune susceptibility locus influencing NKT cells, described herein are subsets of CD93−/− mice exhibiting a profound state of NKT cell deficiency.

In one embodiment, using three distinct mAb specific for mouse CD93, aberrant expression by early B cell progenitors is shown in these autoimmune susceptible mice. In another embodiment, the aberrant cell surface expression of CD93 is associated with an Asn→His polymorphism at amino acid 264 in NOD and NZB/W F1 mice. This polymorphism falls within the first EGF-like domain of CD93. In one embodiment, mutations within the EGF-like domains of the selectin family members, to which CD93 bears a unique resemblance, inhibit their activity as adhesion molecules. In one embodiment, a defect in TR B cell production in NOD mice results from inefficient egress from the BM. In another embodiment, this homeostatic lesion translates into relaxed negative selection at the TR→FO stage of B cell development and may set the stage for B cell autoimmunity in another embodiment. In one embodiment, CD93 has a role of as an adhesion molecule, regulating the efficiency of immature B-cell egress from the BM, and by extension the rate of peripheral TR B cell production.

Accordingly and in one embodiment, provided herein is an isolated nucleic acid molecule encoding a mutated CD93 protein.

In one embodiment, the present invention provides an isolated nucleic acid molecule comprising the nucleotide sequence set forth in SEQ ID No: 3. In another embodiment, the isolated nucleic acid molecule is a fragment of SEQ ID No: 3, wherein the fragment comprises residue 790 of SEQ ID No: 3 or an equivalent residue thereof. In another embodiment, the isolated nucleic acid molecule is a DNA molecule. In another embodiment, the isolated nucleic acid molecule is an RNA molecule. In another embodiment, the isolated nucleic acid molecule is any other type of nucleotide molecule known in the art. In another embodiment, the fragment is at least 20 nucleotides in length. Each possibility represents a separate embodiment of the present invention.

In another embodiment, a nucleotide molecule utilized in methods and compositions of the present invention is at least 8 nucleotides in length. In another embodiment, the length is at least 10 nucleotides. In another embodiment, the length is at least 12 nucleotides. In another embodiment, the length is at least 15 nucleotides. In another embodiment, the length is at least 20 nucleotides. In another embodiment, the length is at least 25 nucleotides. In another embodiment, the length is at least 30 nucleotides. In another embodiment, the length is at least 40 nucleotides. In another embodiment, the length is at least 50 nucleotides. In another embodiment, the length is at least 70 nucleotides. In another embodiment, the length is at least 100 nucleotides. In another embodiment, the length is at least 120 nucleotides. In another embodiment, the length is at least 150 nucleotides. In another embodiment, the length is at least 200 nucleotides. In another embodiment, the length is at least 250 nucleotides. In another embodiment, the length is at least 300 nucleotides. In another embodiment, the length is at least 400 nucleotides. In another embodiment, the length is at least 500 nucleotides. In another embodiment, the length is at least 600 nucleotides. In another embodiment, the length is at least 700 nucleotides. In another embodiment, the length is at least 800 nucleotides. In another embodiment, the length is at least 1000 nucleotides. In another embodiment, the length is at least 1500 nucleotides. In another embodiment, the length is over 1500 nucleotides.

In another embodiment, a nucleotide molecule of the present invention is complementary to a C1qRP sequence over a stretch of at least 10 nucleotides. In another embodiment, the stretch is at least 12 nucleotides. In another embodiment, the stretch is at least 15 nucleotides. In another embodiment, the stretch is at least 20 nucleotides. In another embodiment, the stretch is at least 25 nucleotides. In another embodiment, the stretch is at least 30 nucleotides. In another embodiment, the stretch is at least 40 nucleotides. In another embodiment, the stretch is at least 50 nucleotides. In another embodiment, the stretch is at least 70 nucleotides. In another embodiment, the stretch is at least 100 nucleotides. In another embodiment, the stretch is at least 120 nucleotides. In another embodiment, the stretch is at least 150 nucleotides. In another embodiment, the stretch is at least 200 nucleotides. In another embodiment, the stretch is at least 250 nucleotides. In another embodiment, the stretch is at least 300 nucleotides. In another embodiment, the stretch is at least 400 nucleotides.

Each length represents a separate embodiment of the present invention.

In another embodiment, the present invention provides an isolated nucleic acid molecule complementary to an isolated nucleic acid molecule of described herein.

In another embodiment, the present invention provides an isolated nucleic acid molecule, wherein the isolated nucleic acid molecule encodes an polypeptide, wherein the polypeptide comprises the AA sequence set forth in SEQ ID No: 4. In another embodiment, the present invention provides a nucleic acid molecule complementary to the above isolated nucleic acid molecule. In another embodiment, the nucleic acid molecule is a DNA molecule. In another embodiment, the nucleic acid molecule is an RNA molecule. Each possibility represents a separate embodiment of the present invention.

In another embodiment, the present invention provides an isolated nucleic acid molecule, wherein the isolated nucleic acid molecule encodes an polypeptide, wherein the polypeptide comprises a fragment of the AA sequence set forth in SEQ ID No: 4, wherein the fragment comprises residue 264 of SEQ ID No: 4 or an equivalent residue thereof. In another embodiment, the AA fragment is at least 10 AA in length. In another embodiment, the present invention provides a nucleic acid molecule complementary to the above isolated nucleic acid molecule. In another embodiment, the nucleic acid molecule is a DNA molecule. In another embodiment, the nucleic acid molecule is an RNA molecule. Each possibility represents a separate embodiment of the present invention.

"Equivalent residue" refers, in another embodiment, to a corresponding residue in a sequence that is homologous or is a variant or isomer of the reference sequence. In another embodiment, the corresponding residue need not have exactly the same position in the primary protein structure; e.g. if a homologous sequence contains a gap or insertion relative to the reference sequence. Each possibility represents a separate embodiment of the present invention.

In another embodiment, a polypeptide utilized in methods and compositions of the present invention is at least 8 AA in length. In another embodiment, the length is at least 10 AA. In another embodiment, the length is at least 12 AA. In another embodiment, the length is at least 15 AA. In another embodiment, the length is at least 20 AA. In another embodiment, the length is at least 25 AA. In another embodiment, the length is at least 30 AA. In another embodiment, the length is at least 40 AA. In another embodiment, the length is at least 50 AA. In another embodiment, the length is at least 70 AA. In another embodiment, the length is at least 100 AA. In another embodiment, the length is at least 120 AA. In another embodiment, the length is at least 150 AA. In another embodiment, the length is at least 200 AA. In another embodiment, the length is at least 250 AA. In another embodiment, the length is at least 300 AA. In another embodiment, the length is at least 400 AA. In another embodiment, the length is at least 500 AA. In another embodiment, the length is at least 600 AA. In another embodiment, the length is at least 700 AA. In another embodiment, the length is at least 800 AA. In another embodiment, the length is at least 1000 AA. In another embodiment, the length is at least 1500 AA. In another embodiment, the length is over 1500 AA.

Each length represents a separate embodiment of the present invention.

In one embodiment, C1qRP encodes an approximately 120 kDa O-sialoglycoprotein. In one embodiment, C1qRp, functions as an intercellular adhesion molecule. In one embodiment, C1qRP is a heavily O-glycosylated cell surface protein involved in the regulation of phagocytic activity. In one embodiment, C1qRp is selectively expressed by cells with a myeloid lineage, endothelial cells, platelets, monocytes, neutrophils, stem cells, and microglia. In one embodiment C1qRP defines a stem cell population with hematopoietic and hepatic potential. In one embodiment, C1qRp is a positive marker of bone marrow repopulating stem cells. In one embodiment C1qRp is expressed on both CD34− and CD34+ stem cells from umbilical cord blood and adult bone marrow.

The polymorphism detected in methods of the present invention, in another embodiment, renders the C1qRP gene inactive. In another embodiment, the gene product is conformationally inactive. In another embodiment, the gene product is transcriptionally inactive. In another embodiment, the gene product is translationally inactive. In another embodiment, the gene product is rendered inactive by any other mechanism known in the art. In another embodiment, the polymorphism reduces the expression of the gene product. In another embodiment, the polymorphism abrogates expression of the gene product. In another embodiment, the polymorphism reduces the activity of the gene product. In another embodiment, the polymorphism abrogates activity of the gene product. Each possibility represents a separate embodiment of the present invention.

In another embodiment, the polymorphism detected in methods of the present invention is located in the coding sequence of the gene. In another embodiment, the polymorphism is located in an intron. In another embodiment, the polymorphism is located in a 3' untranslated region. In another embodiment, the polymorphism is located in a 5' untranslated region. In another embodiment, the polymorphism is located in the promoter region. In another embodiment, the polymorphism is located in a transcriptional enhancer. In another embodiment, the polymorphism is located in a translational regulatory region. In another embodiment, the polymorphism is located in any other location that affects the gene product or its expression level. Each possibility represents a separate embodiment of the present invention.

In another embodiment, the polymorphism is located in a region encoding an EGF-like domain of the expression product of the C1qRP gene. In another embodiment, the polymorphism is in a region encoding a calcium-binding motif of an EGF-like domain of a product of the gene. In another embodiment, a polymorphism of the present invention, while not in the region encoding the EGF-like domain, affects the structure and/or function of the EGF-like domain of the protein product. In another embodiment, a polymorphism of the present invention, while not in the region encoding the calcium-binding motif, affects the structure and/or function of the calcium-binding motif of the protein product. In another embodiment, the effect is due to secondary and/or tertiary structural interaction.

In another embodiment, a polymorphism of a present invention is in the coding region of the C1qRP gene. In another embodiment, the polymorphism is in a non-coding region of the C1qRP gene. In another embodiment, the polymorphism is in the codon encoding Asn267. In another embodiment, the polymorphism results in an Asn267His mutation in the protein product. In another embodiment, the polymorphism is A802C. In another embodiment, the polymorphism is in a residue corresponding with A802 on a homologous C1qRP gene. In another embodiment, the polymorphism disrupts the binding site of MAb AA4.1 on the protein product, or a corresponding epitope thereof on a protein product homologous to the mouse C1qRP product. In another embodiment, the polymorphism disrupts the binding site of MAb 493 on the protein product, or a corresponding epitope thereof.

The C1qRP gene that is analyzed in methods of the present invention is, in another embodiment, in a somatic cell of the human subject. In another embodiment, the cell is in a germ-line cell of the human subject. "Cell of the subject" includes, in another embodiment, both a cell associated with the subject at the time of testing and a cell isolated from the subject, using any appropriate tissue or cell isolation method known in the art. In another embodiment, both in vivo and ex vivo methods are included in the present invention. Each possibility represents a separate embodiment of the present invention.

In another embodiment, the cell wherefrom the C1qRP gene is isolated is a B cell. In another embodiment, the cell is a B cell precursor. In another embodiment, the cell is a hematopoietic cell. In another embodiment, the cell is a bone marrow hematopoietic cell. In another embodiment, the cell is a B cell progenitor. In another embodiment, the cell is an immature B cell. In another embodiment, the cell is a transitional B cell. In another embodiment, the cell is any other type of B cell precursor known in the art. In another embodiment, the cell is any other type of B cell progenitor known in the art. In another embodiment, the cell is any other cell type known in the art. Each possibility represents a separate embodiment of the present invention. In one embodiment, a defect in antigen presenting ability of B-cells gives rise to islet reactive CD4$^+$ T cells that precipitate T1DM.

CD93 gene maps to the Idd13 locus but has not, hitherto, been considered as a diabetes susceptibility gene. The CD93 gene is tightly linked to the Lupus susceptibility loci, Wbw1 and Nkt2, in the region of 82-84 cM on mouse chromosome 2. Interestingly, Idd13 subcongenic NOD mice, which do not harbor the B6 CD93 allele, exhibit a higher spontaneous diabetes incidence than those with the B6 allele introgressed. In one embodiment, NOD CD93 polymorphism acts as a diabetes susceptibility locus by causing defective immature B cell egress from the bone marrow and, thereby, compromising TR B cell compartment homeostasis and clonal selection at the TR→FO checkpoint.

In one embodiment, Non obese diabetic (NOD) mouse strain serves as a model for investigating pathogenesis of autoimmune mediated Type 1 Diabetes (T1D) in humans. Genetic linkage studies have revealed that the defect(s) in NOD mouse lies in the Idd locus on chromosome 2. Scientists widely believe that multiple genes in this locus might contribute to T1DM and Lupus among other autoimmune diseases. Besides containing other genes, this locus also codes for immune system molecules such as MHC/HLA antigens. HLA DQ8 and its mouse equivalent I-Ag7 have been studied in detail. Studies point to the hypothesis that pathogenesis of T1DM and NOD is remarkably similar.

Accordingly and in one embodiment, described herein is a method of providing a prognosis for a subject developing an autoimmune disease, comprising the steps of: Obtaining a biological sample from the subject; and Analyzing the sample for a mutation in a CD93 gene or its encoded protein, whereby if the CD93 gene or its encoded protein is mutated, the subject has an increased risk of developing an autoimmune disease.

In another embodiment, provided herein is a method for identifying a human subject having an auto-immune disease, the method comprising the step of detecting the presence or absence of a genetic polymorphism associated with insulin-dependent diabetes mellitus in a C1qRP gene of the subject, whereby the presence of the genetic polymorphism identifies a subject that has the auto-immune disease. In another embodiment, the auto-immune disease is a diabetes mellitus. In another embodiment, the auto-immune disease is any other auto-immune disease known in the art. In another embodiment, the method further comprises the step of obtaining from the subject a tissue sample containing C1qRP gene. In another embodiment, provided herein is a kit for performing the above method, the kit comprising a means for detecting the presence or absence of a genetic polymorphism associated with insulin-dependent diabetes mellitus in a C1qRP gene. Each possibility represents a separate embodiment of the present invention.

In another embodiment, provided herein is a method for identifying a human subject at risk for developing an auto-immune disease, the method comprising the step of detecting the presence or absence of a genetic polymorphism associated with SLE in a C1qRP gene of the subject, whereby the presence of the genetic polymorphism identifies a subject that is at risk for developing an auto-immune disease. In another embodiment, the auto-immune disease is SLE. In another embodiment, the auto-immune disease is any other auto-immune disease known in the art to be associated with idd13 locus. In another embodiment, provided herein is a kit for performing the above method, the kit comprising a means for detecting the presence or absence of a genetic polymorphism associated with insulin-dependent diabetes mellitus in a C1qRP gene. Each possibility represents a separate embodiment of the present invention.

In another embodiment, the activity is mediated by an EGF-like domain of an expression product of the C1qRP gene. In another embodiment, the activity is mediated by a calcium-binding motif of an EGF-like domain of an expression product of the C1qRP gene. In another embodiment, the activity is any other activity of an expression product of the C1qRP gene. Each possibility represents a separate embodiment of the present invention.

In another embodiment of methods and compositions of the present invention, a B cell of the subject is contacted with the therapeutic or diagnostic modality. In another embodiment, a B cell precursor is contacted. In another embodiment, a hematopoietic cell of the subject is contacted. In another embodiment, a bone marrow hematopoietic cell of the subject is contacted. In another embodiment, a B cell progenitor of the subject is contacted. In another embodiment, an immature B cell of the subject is contacted. In another embodiment, a transitional B cell of the subject is contacted. In another embodiment, any other type of B cell precursor known in the art of the subject is contacted. In another embodiment, any other type of B cell progenitor known in the art of the subject is contacted. In another embodiment, any other cell type known in the art is contacted. Each possibility represents a separate embodiment of the present invention.

In another embodiment, provided herein is a method for treating a subject having an auto-immune disease, comprising the step of contacting the subject with a compound or composition that increases an expression of a wild type C1qRP protein in a cell of the subject, thereby treating a subject having an auto-immune disease. In another embodiment, the auto-immune disease is a diabetes mellitus. In another embodiment, the auto-immune disease is any other auto-immune disease known in the art. In another embodiment, provided herein is a kit for performing the above method, the kit comprising a means for increasing C1qRP protein expression in a subject. Each possibility represents a separate embodiment of the present invention.

In another embodiment, provided herein is a method for halting a progression of an auto-immune disease in a subject, comprising the step of contacting the subject with a compound or composition that increases an expression of a C1qRP protein in a cell of the subject, thereby halting a progression of an auto-immune disease in a subject. In another embodiment, the auto-immune disease is a diabetes mellitus. In another embodiment, the auto-immune disease is any other auto-immune disease known in the art. In another embodiment, provided herein is a kit for performing the above method, the kit comprising a means for increasing wild type C1qRP protein expression in a subject. Each possibility represents a separate embodiment of the present invention.

In another embodiment, provided herein is a method for impeding a progression of an auto-immune disease in a subject, comprising the step of contacting the subject with a compound or composition that increases an expression of a wild type C1qRP protein in a cell of the subject, thereby impeding a progression of an auto-immune disease in a subject. In another embodiment, the auto-immune disease is a diabetes mellitus. In another embodiment, the auto-immune disease is any other auto-immune disease known in the art. In another embodiment, provided herein is a kit for performing the above method, the kit comprising a means for increasing wild type C1qRP protein expression in a subject. Each possibility represents a separate embodiment of the present invention.

In another embodiment, provided herein is a method for treating a subject having an auto-immune disease, comprising the step of contacting the subject with a wild type C1qRP protein, fragment thereof, or nucleotide molecule encoding the C1qRP protein or fragment thereof, thereby treating a subject having an auto-immune disease. In another embodiment, the auto-immune disease is a diabetes mellitus. In another embodiment, the auto-immune disease is any other auto-immune disease known in the art. In another embodiment, provided herein is a kit for performing the above method, the kit comprising a nucleotide molecule encoding the C1qRP protein or a fragment thereof. Each possibility represents a separate embodiment of the present invention.

In another embodiment, the agonist or antagonist is a protein mimetic. In another embodiment, the agonist or antagonist is a C1qRP protein mimetic. Each possibility represents a separate embodiment of the present invention.

In another embodiment, a kit of the present invention further comprises a manual or instructional material.

In another embodiment, the interacting protein is an EGF family member. In another embodiment, the interacting protein is any other protein known in the art. Each possibility represents a separate embodiment of the present invention.

As provided herein, the presence of a mutant C1qRP protein is correlated with susceptibility to diabetes. Thus, the present invention shows that decreasing the aberrant activity of the mutated C1qRP protein is therapeutic for diabetes type (I).

The auto-immune disease that is detected or treated by a method of the preset invention is, in another embodiment, systemic lupus erythematosus (SLE). Accordingly and in one embodiment, provided herein is a method of treating, or in another embodiment, inhibiting or suppressing, or in another embodiment, ameliorating symptoms associated with SLE, comprising the step of contacting a subject in need thereof with the compositions described herein.

In another embodiment, the target C1qRP gene of the present invention is also known as CD93. In another embodiment, the target gene is also known as C1QR1. In another embodiment, the target gene is also known as CDw93. In another embodiment, the target gene is also known as MXRA4. In another embodiment, the target gene is also known as C1qR(P). In another embodiment, the target gene is also known as dJ737E23.1. In another embodiment, the target gene is any other C1qRP-related gene known in the art. Each possibility represents a separate embodiment of the present invention.

Throughout the following description "C1qRP" is used to refer to either C1qRP or CD93.

As provided herein, a C1qRP gene having the following sequence was disrupted:

(SEQ ID No: 1)
atggccatctcaactggtttgttcctgctgctggggctccttggccagc cctgggcaggggctgctgctgattcacaggctgtggtgtgcgaggggac tgcctgctatacagcccattggggcaagctgagtgccgctgaagcccag catcgctgcaatgagaatggaggcaatcttgccaccgtgaagagtgagg aggaggcccggcatgttcagcaagccctgactcagctcctgaagaccaa ggcacccttggaagcaaagatgggcaaattctggatcgggctccagcga gagaagggcaactgtacgtaccatgatttgccaatgaggggcttcagct gggtgggtggtggagaggacacagcttattcaaactggtacaaagccag caagagctcctgtatcttaaacgctgtgtgtccctcatactggacctg tccttgacacctcaccccagccatctgcccaagtggcatgagagtccct gtgggacccccgaagctccaggtaacagcattgaaggtttcctgtgcaa gttcaacttcaaaggcatgtgtaggccactggcgctgggtggtccaggg cgggtgacctataccacccctttccaggccactacctcctctctggagg ctgtgcctttgcctctgtagccaatgtagcttgtggggatgaagctaag agtgaaacccactatttcctatgcaatgaaaagactccaggaatatttc actggggcagctcaggcccactctgtgtcagcccaagtttggttgcag tttcaacaacgggggctgccagcaggattgcttcgaaggtggcgatggc tccttccgctgcggctgccggcctggatttcgactgctggatgatctag taacttgtgcctccaggaaccctgcagctcaaacccatgcacaggagg tggcatgtgccattctgtaccactcagtgaaaactacacttgccgttgt cccagcggctaccagctggactctagccaagtgcactgtgtggatatag atgagtgccaggactcccctgtgcccaggattgtgtcaacactctagg gagcttccactgtgaatgttgggttggttaccaacccagtggccccaag gaagaggcctgtgaagatgtggatgagtgtgcagctgccaactcgccct gtgcccaaggctgcatcaacactgatggctcttctactgctcctgtaa agagggctatattgtgtctggggaagacagtacccagtgtgaggatata gatgagtgttcggacgcaaggggcaatccatgtgattccctgtgcttca acacagatggttccttcaggtgtggctgcccgccaggctgggagctggc tcccaatggggtcttttgtagcagggcactgtgttttctgaactacca gccaggcctccccaaaaggaagacaacgatgacagaaaggagagtacta tgcctcctactgaaatgcccagttctcctagtggctctaaggatgtctc caacagagcacagacaacaggtctcttcgtccaatcagatattcccact gcctctgttccactagaaatagaaatccctagtgaagtatctgatgtct -continued

```
ggttcgagttgggcacatacctccccacgacctccggccacagcaagcc gacacatgaagattctgtgtctgcacacagtgacaccgatgggcagaac ctgcttctgtttacatcctggggacggtggtggccatctcactcttgct ggtgctggccctagggattctcatttatcataaacgagagccaagaag gaggagataaaagagaagaagcctcagaatgcagccgacagctattcct gggttccagagcgagcagagagccaagccccgagaatcagtacagccc aacaccagggacagactgctga.
```

In one embodiment, SEQ ID No: 1 encodes a protein having the following sequence:

(SEQ ID No: 2)
```
MAISTGLFLLLGLLGQPWAGAAADSQAVVCEGTACYTAHWGKLSAAEA
QHRCNENGGNLATVKSEEEARHVQQALTQLLKTKAPLEAKMGKFWIGL
QREKGNCTYHDLPMRGFSWVGGGEDTAYSNWYKASKSSC1FKRCVSLI
LDLSLTPHPSHLPKWHESPCGTPEAPGNSIEGFLCKFNFKGMCRPLAL
GGPGRVTYTTPFQATTSSLEAVPFASVANVACGDEAKSETHYFLCNEK
TPGIFHWGSSGPLCVSPKFGCSFNNGGCQQDCFEGGDGSFRCGCRPGF
RLLDDLVTCASRNPCSSNPCTGGGMCHSVPLSENYTCRCPSGYQLDSS
QVHCVDIDECQDSPCAQDCVNTLGSFHCECWVGYQPSGPKEEACEDVD
ECAAANSPCAQGCINTDGSFYCSCKEGYIVSGEDSTQCEDIDECSDAR
GNPCDSLCFNTDGSFRCGCPPGWELAPNGVFCSRGTVFSELPARPPQK
EDNDDRKESTIVIPPTEMPSSPSGSKDVSNRAQTTGLFVQSDIPTASV
PLEIEIPSEVSDVWFELGTYLPTTSGHSKPTHEDSVSAHSDTDGQNLL
LFYILGTVVAISLLLVLALGILIYHKRRAKKEEIKEKKPQNAADSYSW
VPERAESQAPENQYSPTPGTDC.
```

The mutated C1qRP gene identified herein had the sequence:

(SEQ ID No: 3)
```
atggccatctcaactggtttgttcctgctgctggggctccttggccag ccctgggcaggggctgctgctgattcacaggctgtggtgtgcgagggg actgctgctatacagcccattggggcaagctgagtgccgctgaagcc cagcatcgctgcaatgagaatggaggcaatcttgccaccgtgaagagt gaggaggaggcccggcatgttcagcaagccctgactcagctcctgaag accaaggcaccttggaagcaaagatgggcaaattctggatcgggctc cagcgagagaagggcaactgtacgtaccatgatttgccaatgaggggc ttcagctgggtggtggtggagaggacacagcttattcaaactggtac aaagccagcaagagctcctgtatctttaaacgctgtgtgtccctcata ctggacctgtccttgacacctcacccagccatctgcccaagtggcat gagagtccctgtgggaccccgaagctccaggtaacagcattgaaggt ttcctgtgcaagttcaacttcaaaggcatgtgtaggccactggcgctg ggtggtccagggcgggtgacctataccaccccttccaggccactacc
```

-continued

```
tcctctctggaggctgtgccttttgcctctgtagccaatgtagcttgt ggggatgaagctaagagtgaaacccactatttcctatgcaatgaaaag actccaggaatatttcactggggcagctcaggcccactctgtgtcagc cccaagtttggttgcagtttccacaacgggggctgccagcaggattgc ttcgaaggtggcgatggctccttccgctgcggctgccggcctggattt cgactgctggatgatctagtaacttgtgcctccaggaaccctgcagc tcaaacccatgcacaggaggtggcatgtgccattctgtaccactcagt gaaaactacacttgccgttgtcccagcggctaccagctggactctagc caagtgcactgtgtggatatagatgagtgccaggactcccctgtgcc caggattgtgtcaacactctagggagcttccactgtgaatgtgggtt ggttaccaacccagtggccccaaggaagaggcctgtgaagatgtggat gagtgtgcagctgccaactcgccctgtgcccaaggctgcatcaacact gatggctctttctactgctcctgtaaagagggctatattgtgtctggg gaagacagtaccccagtgtgaggatatagatgagtgttcggacgcaagg ggcaatccatgtgattccctgtgcttcaacacagatggttcttcagg tgtggctgcccgccaggctgggagctggctcccaatggggtcttttgt agcaggggcactgtgttttctgaactaccagccaggcctccccaaaag gaagacaacgatgacagaaaggagagtactatgcctctactgaaatg cccagttctcctagtggctctaaggatgtctccaacagagcacagaca acaggtctcttcgtccaatcagatattcccactgcctctgttccacta gaaatagaaatccctagtgaagtatctgatgtctggttcgagttgggc acatacctccccacgacctccggccacagcaagccgacacatgaagat tctgtgtctgcacacagtgacaccgatgggcagaacctgcttctgttt tacatcctggggacggtggtggccatctcactcttgctggtgctggcc ctagggattctcatttatcataaacgagagccaagaaggaggagata aaagagaagaagcctcagaatgcagccgacagctattcctgggttcca gagcgagcagagagccaagccccgagaatcagtacagcccaacacca gggacagactgctga.
```

SEQ ID No: 3 encodes a protein having the following sequence:

(SEQ ID No: 4)
```
MAISTGLFLLLGLLGQPWAGAAADSQAVVCEGTACYTAHWGKLSAAEA
QHRCNENGGNLATVKSEEEARHVQQALTQLLKTKAPLEAKMGKFWIGL
QREKGNCTYHDLPMRGFSWVGGGEDTAYSNWYKASKSSCIFKRCVSLI
LDLSLTPHPSHLPKWHESPCGTPEAPGNSIEGFLCKFNFKGMCRPLAL
GGPGRVTYTTPFQATTSSLEAVPFASVANVACGDEAKSETHYFLCNEK
TPGIFHWGSSGPLCVSPKFGCSFHNGGCQQDCFEGGDGSFRCGCRPGF
RLLDDLVTCASRNPCSSNPCTGGGMCHSVPLSENYTCRCPSGYQLDSS
QVHCVDIDECQDSPCAQDCVNTLGSFHCECWVGYQPSGPKEEACEDVD
ECAAANSPCAQGCINTDGSFYCSCKEGYIVSGEDSTQCEDIDECSDAR
GNPCDSLCFNTDGSFRCGCPPGWELAPNGVFCSRGTVFSELPARPPQK
```

```
EDNDDRKESTMPPTEMPSSPSGSKDVSNRAQTTGLFVQSDIPTASVPL

EIEIPSEVSDVWFELGTYLPTTSGHSKPTHEDSVSAHSDTDGQNLLLF

YILGTVVAISLLLVLALGILIYHKRRAKKEEIKEKKPQNAADSYSWVP

ERAESQAPENQYSPTPGTDC.
```

In another embodiment, the C1qRP gene that is disrupted is a human homologue of SEQ ID No: 1.

In another embodiment, the C1qRP gene that is disrupted encodes a human homologue of a protein whose sequence is set forth in SEQ ID No: 2.

In another embodiment, the mutated C1qRP gene is a human homologue of SEQ ID No: 3.

In another embodiment, the mutated C1qRP gene encodes a human homologue of SEQ ID No: 4.

In another embodiment, the C1qRP gene that is disrupted has the sequence:

```
                                              (SEQ ID No: 5)
atggccacctccatgggcctgctgctgctgctgctgctgctcctgac ccagcccggggcgggacgggagctgacacggaggcggtggtctgcg tggggaccgcctgctacacggcccactcgggcaagctgagcgctgcc gaggcccagaaccactgcaaccagaacgggggcaacctggccactgt gaagagcaaggaggaggcccagcacgtccagcgagtactggcccagc tcctgaggcgggaggcagccctgacgcgaggatgagcaagttctgg attgggctccagcgagagaagggcaagtgcctggaccctagtctgcc gctgaagggcttcagctgggtgggcggggggaggacacgccttact ctaactggcacaaggagctccggaactcgtgcatctccaagcgctgt gtgtctctgctgctggacctgtcccagccgctccttccagccgcct ccccaagtggtctgagggccctgtgggagcccaggctcccccggaa gtaacattgagggcttcgtgtgcaagttcagcttcaaaggcatgtgc cggcctctggccctggggggcccaggtcaggtgacctacaccaccc cttccagaccaccagttcctccttggaggctgtgcccttgcctctg cggccaatgtagcctgtggggaaggtgacaaggacgagactcagagt cattatttcctgtgcaaggagaaggccccgatgtgttcgactggg cagctcgggcccctctgtgtcagcccaagtatggctgcaacttca acaatggggctgccaccaggactgctttgaagggggatggctcc ttcctctgcggctgccgaccaggattccggctgctggatgacctggt gacctgtgcctctcgaaaccctgcagctccagcccatgtcgtgggg gggccacgtgcgccctgggaccccatgggaaaactacacgtgccgc tgccccaagggtaccagctggactcgagtcagctggactgtgtgga cgtggatgaatgccaggactccccctgtgcccaggagtgtgtcaaca cccctggggcttccgctgcgaatgctgggttggctatgagccggc ggtcctggagaggggcctgtcaggatgtggatgagtgtgctctggg tcgctcgccttgcgcccagggctgcaccaacacagatggctcatttc actgctcctgtgaggagggctacgtcctggccggggaggacgggact cagtgccaggacgtggatgagtgtgtgggcccggggggcccctctg
```

```
cgacagcttgtgcttcaacacacaagggtccttccactgtggctgcc tgccaggctgggtgctggcccaaatggggtctcttgcaccatgggg cctgtgtctctgggaccaccatctgggccccccgatgaggaggacaa aggagagaaagaagggagccaccgtgccccgcgctgcaacagccagtc ccacaaggggccccgagggcacccccaaggctacacccaccacaagt agaccttcgctgtcatctgacgcccccatcacatctgccccactcaa gatgctggccccagtgggtcctcaggcgtctggagggagcccagca tccatcacgccacagctgcctctggccccaggagcctgcaggtggg gactcctccgtggccacacaaaacaacgatggcactgacgggcaaaa gctgcttattctacatcctaggcaccgtggtggccatcctactcct gctggccctggctctggggctactggtctatcgcaagcggagagcga agagggaggagaagaaggagaagaagccccagaatgcggcagacagt tactcctgggtccagagcgagctgagagcagggccatggagaaccag tacagtccgacacctgggacagactgctga.
```

In another embodiment, the C1qRP gene that is disrupted encodes a protein having the sequence:

```
                                              (SEQ ID No: 6)
MATSMGLLLLLLLLLTQPGAGTGADTEAVVCVGTACYTAHSGKLSA

AEAQNHCNQNGGNLATVKSKEEAQHVQRVLAQLLRREAALTARMSK

FWIGLQREKGKCLDPSLPLKGFSWVGGGEDTPYSNWHKELRNSCIS

KRCVSLLLDLSQPLLPSRLPKWSEGPCGSPGSPGSNIEGFVCKFSF

KGMCRPLALGGPGQVTYTTPFQTTSSSLEAVPFASAANVACGEGDK

DETQSHYFLCKEKAPDVFDWGSSGPLCVSPKYGCNFNNGGCHQDCF

EGGDGSFLCGCRPGFRLLDDLVTCASRNPCSSSPCRGGATCALGPH

GKNYTCRCPQGYQLDSSQLDCVDVDECQDSPCAQECVNTPGGFRCE

CWVGYEPGGPGEGACQDVDECALGRSPCAQGCTNTDGSFHCSCEEG

YVLAGEDGTQCQDVDECVGPGGPLCDSLCFNTQGSFHCGCLPGWVL

APNGVSCTMGPVSLGPPSGPPDEEDKGEKEGSTVPRAATASPTRGP

EGTPKATPTTSRPSLSSDAPITSAPLKMLAPSGSSGVWREPSIHHA

TAASGPQEPAGGDSSVATQNNDGTDGQKLLLFYILGTVVAILLLLA

LALGLLVYRKRRAKREEKKEKKPQNAADSYSWVPERAESRAMENQY

SPTPGTDC.
```

In another embodiment, the mutated C1qRP gene has the sequence:

```
                                              (SEQ ID No: 7)
atggccacctccatgggcctgctgctgctgctgctgctcctgacc cagcccggggcgggacgggagctgacacggaggcggtggtctgcgtg gggaccgcctgctacacggcccactcgggcaagctgagcgctgccgag gcccagaaccactgcaaccagaacgggggcaacctggccactgtgaag agcaaggaggaggcccagcacgtccagcgagtactggcccagctcctg
```

-continued

```
aggcgggaggcagccctgacggcgaggatgagcaagttctggattggg
ctccagcgagagaagggcaagtgcctggaccctagtctgccgctgaag
ggcttcagctgggtgggcggggggaggacacgccttactctaactgg
cacaaggagctccggaactcgtgcatctccaagcgctgtgtgtctctg
ctgctggacctgtcccagccgctccttcccagccgcctcccaagtgg
tctgagggcccctgtgggagcccaggctccccggaagtaacattgag
ggcttcgtgtgcaagttcagcttcaaaggcatgtgccggcctctggcc
ctgggggccccaggtcaggtgacctacaccaccccttccagaccacc
agttcctccttggaggctgtgccctttgcctctgcggccaatgtagcc
tgtggggaaggtgacaaggacgagactcagagtcattatttcctgtgc
aaggagaaggccccgatgtgttcgactggggcagctcgggcccctc
tgtgtcagcccaagtatggctgcaacttcaaccatgggggctgccac
caggactgctttgaaggggggatggctccttcctctgcggctgccga
ccaggattccggctgctggatgacctggtgacctgtgcctctcgaaac
ccttgcagctccagcccatgtcgtggggggccacgtgcgccctggga
ccccatgggaaaaactacacgtgccgctgccccaagggtaccagctg
gactcgagtcagctggactgtgtggacgtggataatgccaggactcc
ccctgtgccaggagtgtgtcaacacccctgggggcttccgctgcgaa
tgctgggttggctatgagccgggcggtcctggagaggggcctgtcag
gatgtggatgagtgtgctctgggtcgctcgccttgcgcccagggctgc
accaacacagatggctcatttcactgctcctgtgaggagggctacgtc
ctggccggggaggacgggactcagtgccaggacgtggatgagtgtgtg
ggcccggggggccccctctgcgacagcttgtgcttcaacacacaaggg
tccttccactgtggctgcctgccaggctgggtgctggcccaaatggg
gtctcttgcaccatggggcctgtgtctctgggaccaccatctgggccc
cccgatgaggaggacaaaggagagaaaggggagcaccgtgccccgc
gctgcaacagccagtcccacaaggggcccgagggcaccccaaggct
acacccaccacaagtagaccttcgctgtcatctgacgccccatcaca
tctgccccactcaagatgctggccccagtggggtcctcaggcgtctgg
agggagcccagcatccatcacgccacagctgcctctggccccaggag
cctgcaggtgggactcctccgtggccacacaaaacaacgatggcact
gacgggcaaaagctgctatattctacatcctaggcaccgtggtggcca
tcctactcctgctggccctggctctggggctactggtctatcgcaagc
ggagagcgaagagggaggagaagaaggagaagaagccccagaatgcgg
cagacagttactcctgggttccagagcgagctgagagcagggccatgg
agaaccagtacagtccgacacctgggacagactgctga.
```

In another embodiment, the mutated C1qRP gene encodes a protein having the sequence:

(SEQ ID No: 8)
```
MATSMGLLLLLLLLLTQPGAGTGADTEAVVCVGTACYTAHSGKLSAAE
AQNHCNQNGGNLATVKSKEEAQHVQRVLAQURREAALTARMSKFWIGL
QREKGKCLDPSLPLKGFSWVGGGEDTPYSNWHKELRNSCISKRCVSLL
LDLSQPLLPSRLPKWSEGPCGSPGSPGSNIEGFVCKFSFKGMCRPLAL
GGPGQVTYTTPFQTTSSSLEAVPFASAANVACGEGDKDETQSHYFLCK
EKAPDVFDWGSSGPLCVSPKYGCNFHNGGCHQDCFEGGDGSFLCGCRP
GFRLLDDLVTCASRNPCSSSPCRGGATCALGPHGKNYTCRCPQGYQLD
SSQLDCVDVDECQDSPCAQECVNTPGGFRCECWVGYEPGGPGEGACQD
VDECALGRSPCAQGCTNTDGSFHCSCEEGYVLAGEDGTQCQDVDECVG
PGGPLCDSLCFNTQGSFHCGCLPGWVLAPNGVSCTMGPVSLGPPSGPP
DEEDKGEKEGSTVPRAATASPTRGPEGTPKATPTTSRPSLSSDAPITS
APLKMLAPSGSSGVWREPSIHHATAASGPQEPAGGDSSVATQNNDGTD
GQKLLLFYILGTVVAILLLLALALGLLVYRKRRAKREEKKEKKPQNAA
DSYSWVPERAESRAMENQYSPTPGTDC.
```

In another embodiment, an isolated nucleotide molecule of the present invention has the sequence set forth in SEQ ID No: 5 or 7. In another embodiment, the nucleotide molecule is a homologue of SEQ ID No: 5 or 7, having a mutation in a residue of codon 267 or an equivalent codon thereof. In another embodiment, the nucleotide molecule is a variant of SEQ ID No: 5 or 7, having a mutation in a residue of codon 267 or an equivalent codon thereof. In another embodiment, the nucleotide molecule is an isomer of SEQ ID No: 5 or 7, having a mutation in a residue of codon 267 or an equivalent codon thereof. In another embodiment, the nucleotide molecule is a fragment of a homologue of SEQ ID No: 5 or 7, having a mutation in a residue of codon 267 or an equivalent codon thereof. In another embodiment, the nucleotide molecule is a fragment of a variant of SEQ ID No: 5 or 7, having a mutation in a residue of codon 267 or an equivalent codon thereof. In another embodiment, the nucleotide molecule is a fragment of an isomer of SEQ ID No: 5 or 7, having a mutation in a residue of codon 267 or an equivalent codon thereof. In another embodiment, the residue of codon 267 is residue 802 of the coding sequence or an equivalent residue thereof. In another embodiment, the mutation is a point mutation. In another embodiment, the mutation is a mutation to a codon encoding a His residue. Each possibility represents a separate embodiment of the present invention.

In another embodiment, an isolated nucleotide molecule of the present invention encodes a product that is mutated in an EGF-like domain thereof. In another embodiment, the nucleotide molecule encodes a product that is mutated in a calcium-binding motif of an EGF-like domain thereof. Each possibility represents a separate embodiment of the present invention.

In another embodiment, an isolated nucleotide molecule described herein and used in the methods provided, encodes a product wherein the epitope for MAb AA4.1 (Ebioscience, San Diego, Calif.), or an equivalent epitope thereof, immunoreactivity is disrupted. In another embodiment, the nucleotide molecule encodes a product wherein the epitope for MAb 493 (Rolink A G et al, Molecular mechanisms guiding late stages of B-cell development. Immunol Rev. 2004; 197: 41-50), or an equivalent epitope thereof, immunoreactivity is disrupted. Each possibility represents a separate embodiment of the present invention.

In one embodiment, the term "mutation" refers to an alteration in either a nucleotide sequence or an amino acid (AA) sequence, relative to the wild-type sequence.

In another embodiment, an isolated polypeptide described herein and used in the methods provided, contains a mutation that disrupts recognition by MAb AA4.1, or an epitope equivalent to the mouse epitope recognized by MAb AA4.1. In another embodiment, the polypeptide contains a mutation that disrupts recognition by MAb 493, or an epitope equivalent to the mouse epitope recognized by MAb 493. Each possibility represents a separate embodiment of the present invention.

In another embodiment, a mimetic compound described herein and used in the methods provided, is derived from C1qRP by incorporating 1 or more modified AA residues. In another embodiment, one or more of the termini is derivatized to include a blocking group, i.e. a chemical substituent suitable to protect and/or stabilize the N- and C-termini from undesirable degradation. In another embodiment, "undesirable degradation" refers to any type of enzymatic, chemical or biochemical breakdown of the compound at its termini which is likely to affect the function of the compound, i.e. sequential degradation of the compound at a terminal end thereof.

In one embodiment, macrophages from CD93-deficient mice are not deficient in their response to C1q, however, they do exhibit an impaired uptake of apoptotic cells in vivo indicating that in another embodiment, this receptor contributes to the removal of dying cells. In one embodiment, priming of autoreactive T and B cells in both autoimmune diabetes and lupus involves an initial response to apoptotic target cells. Accordingly, in another embodiment, CD93 polymorphism in NOD and NZB/W F1 mice leads to inefficient clearance of apoptotic bodies, thereby setting the stage for the initiation of an autoimmune response.

In one embodiment, Idd13 and the Nkt2 loci on mouse chromosome 2 are implicated in regulating the differentiation of NKT cells, whose relative deficiency in NOD mice is in another embodiment, pathognomonic of islet inflammation. NKT cells constitutively express NK cell markers and receptors encoded by the NK-gene complex (NKC). In one embodiment, the CD93 protein comprises a C-type lectin carbohydrate recognition domain (CRD), similarly to many of the NKC-encoded receptors, including NKRP1 thereby making CD93 constructive in one embodiment, in NKT cell development and function.

Accordingly and in one embodiment, provided herein is a method of providing a prognosis for a subject developing an autoimmune disease, comprising the steps of: Obtaining a biological sample from the subject; and Analyzing the sample for a mutation in a CD93 gene or its encoded protein, whereby if the CD93 gene or its encoded protein is mutated, the subject has an increased risk of developing an autoimmune disease.

In another embodiment, the invention provides a method of providing a prognosis for a subject developing Type I diabetes (DM(I)), comprising the steps of: Obtaining a biological sample from the subject; and Analyzing the sample for a mutation in a CD93 gene or its encoded protein, whereby if the CD93 gene or its encoded protein is mutated, the subject has an increased risk of developing an autoimmune disease In another embodiment, the invention provides a method of providing a prognosis for a subject developing systemic lupus erythematosus (SLE), comprising the steps of: Obtaining a biological sample from the subject; and Analyzing the sample for a mutation in a CD93 gene or its encoded protein, whereby if the CD93 gene or its encoded protein is mutated, the subject has an increased risk of developing systemic lupus erythematosus (SLE)

In another embodiment, provided herein is a method for detecting a risk or susceptibility of a subject to diabetes mellitus. In another embodiment, the risk for developing diabetes is due to a mutation in the C1qRP gene. In another embodiment, the risk for developing diabetes is associated with a mutation in the C1qRP gene. As provided herein, mutations in the C1qRP gene have been correlated by the inventors with the disease. In another embodiment, given the disclosure of the invention that such mutations are associated with a susceptibility to diabetes, methods are utilized to detect mutations in the C1qRP gene, including the mutations disclosed herein, that are associated with a susceptibility to diabetes. In another embodiment, methods described herein and used in the methods provided, include detecting, in a tissue of the subject, the presence or absence of a polymorphism of the C1qRP gene. The detection of a polymorphism in the C1qRP gene includes, in another embodiment, ascertaining the existence of at least one of: a deletion of one or more nucleotides; an addition of one or more nucleotides, a substitution of 1 or more nucleotides; a gross chromosomal rearrangement; an alteration in the level of a messenger RNA transcript; the presence of a non-wild type splicing pattern of a messenger RNA transcript; a non-wild type level of a C1qRP protein; and/or an aberrant level of a C1qRP protein. Each possibility represents a separate embodiment of the present invention.

In one embodiment, C1qRP regulates the developmental fitness of immature B cells for egress from the bone marrow. In one embodiment, the NOD C1qRP mutation causes a homeostatic defect in TR B cell production and abrogates the TR→FO B cell tolerance checkpoint. In one embodiment, the NOD C1qRP mutation limits the availability of BLyS during NOD B cell repertoire formation and/or normalizes the stringency of B cell selection, abrogates autoantibody production and prevents autoimmune diabetes in NOD mice.

Diabetes in the NOD mouse exhibits a number of similarities with T1D in humans. For example, position 57 of the beta chain of the I-Ag7 MHC class II molecule (i.e. the NOD haplotype) is characterized by a similar polymorphism seen in the HLA-DQ8 haplotype in humans, and is tightly linked to disease in the same way that the HLA-DQ8 haplotype is tightly linked to disease in humans. Further, transgenic human HLA-DQ8 can substitute for I-Ag7 in selecting diabetogenic T cells in mice. Thus, diabetes in the NOD mouse shares a high degree of mechanistic conservation with T1D in humans.

The diabetes that is detected, screened for, or treated by methods and compositions described herein and used in the methods provided, is, in another embodiment insulin-dependent diabetes mellitus.

In another embodiment, the target C1qRP molecule of methods and compositions described herein and used in the methods provided, is a wild-type C1qRP. In another embodiment, the target is a mutant molecule. Each possibility represents a separate embodiment of the present invention.

In another embodiment, detecting the polymorphism includes (i) providing a probe/primer comprised of an oligonucleotide that hybridizes to a sense or antisense sequence of a C1qRP gene or naturally occurring mutants thereof, or 5' or 3' flanking sequences naturally associated with a C1qRP gene; (ii) contacting an appropriate nucleic acid-containing sample with the probe/primer; and (iii) detecting, by hybridization of the probe/primer to the nucleic acid, the presence or absence of the polymorphism. In another embodiment, detection of the polymorphism comprises utilizing the probe/primer to determine the nucleotide sequence of a C1qRP gene. In another embodiment, the sequence of flanking nucleic acid sequences is also determined. In another embodiment, the primer is employed in a polymerase chain reaction (PCR). In another embodiment, the primer is employed in a ligase chain reaction (LCR). In another embodiment, the primer is employed in any other amplification reaction known in the art. In another embodiment, the level of a C1qRP protein is detected in an immunoassay using an antibody specifically immuno-reactive with the C1qRP protein. Each possibility represents a separate embodiment of the present invention.

The subject of methods described herein and used in the methods provided, is, in another embodiment, a human subject. In another embodiment, the subject is any other subject known in the art. Each possibility represents a separate embodiment of the present invention.

In another embodiment of methods of the present invention, alteration of the wild-type C1qRP locus is detected. "Alteration" refers, in another embodiment, to all forms of mutations including deletions, insertions and point mutations in the coding and noncoding regions. "Deletions" refers, in another embodiment, to deletions of either the entire gene or only a portion of the gene. Point mutations can introduce, in another embodiment, stop codons, frameshift mutations or amino acid (AA) substitutions. In another embodiment, point mutations or deletions in the promoter change transcription and thereby alter the gene function. Somatic mutations are those that occur only in certain tissues and are not inherited in the germline. Germline mutations can be found in any of a body's tissues and are inherited. In another embodiment, a C1qRP allele not containing a polymorphism described herein and used in the methods provided, is screened for other mutations, such as insertions, small deletions, and point mutations. In another embodiment, point mutational events can occur in a codon region; in a regulatory region, such as the promoter of the gene; in an intron region; or in intron/exon junctions. Each possibility represents a separate embodiment of the present invention.

In another embodiment, fluorescent in situ hybridization (FISH) is utilized in a diagnostic technique of the present invention. In another embodiment, direct DNA sequencing is utilized. In another embodiment, manual sequencing is utilized. In another embodiment, automated fluorescent sequencing is utilized. In another embodiment, PFGE analysis is utilized. In another embodiment, Southern blot analysis is utilized. In another embodiment, single stranded conformation analysis (SSCA) is utilized. In another embodiment, RNase protection assay is utilized. In another embodiment, allele-specific oligonucleotide (ASO) hybridization is utilized. In another embodiment, for ASO assay, an oligonucleotide is designed that detects a specific sequence, and the assay is performed by detecting the presence or absence of a hybridization signal. In another embodiment, dot blot analysis is utilized. In another embodiment, PCR-SSCP is utilized. In another embodiment, DNA microchip technology is utilized. In another embodiment, a technique described in U.S. Pat. Nos. 5,837,492 or 5,800,998, each incorporated herein by reference, is utilized. In another embodiment, any other technique for detecting a polymorphism is utilized. Each possibility represents a separate embodiment of the present invention.

In another embodiment, predisposition to disease is ascertained by testing a tissue of a human for mutations of the C1qRP gene. In another embodiment, a subject who has inherited a germline C1qRP mutation is prone to develop IDDM. In another embodiment, prenatal diagnosis is performed by testing fetal cells, placental cells or amniotic cells for mutations of the C1qRP gene. Each possibility represents a separate embodiment of the present invention.

In another embodiment, single-stranded conformation polymorphism assay (SSCA) is utilized. SSCA detects, in another embodiment, a band that migrates differentially because of a sequence change-induced difference in single-strand, intramolecular base pairing. In another embodiment, high molecular weight (MW) DNA (20 micrograms [mcg]) is digested completely with a restriction endonuclease, DNA fragments are precipitated and DNA precipitates are denatured, electrophoresed, transferred to a membrane, and hybridized to labeled probe. In another embodiment, DNA precipitates are dissolved in denaturing solution (e.g. 0.3 M NaOH/1 mM EDTA) and then mixed with loading buffer (e.g. 50% (vol/vol) glycerol/0.25% xylene cyanol/0.25% bromophenol blue). The mixture is applied to a neutral 5% polyacrylamide gel (20×40×0.2 cm) with or without 10% glycerol in a well of 10 mm width and subjected to electrophoresis (e.g. in 90 millimolar (mM) Tris-borate, pH 8.3/4 mM EDTA at 180 V for 12-36 hr at 17° C.). In another embodiment, DNA fragments in the gel are then transferred to a nylon membrane (e.g. Hybond-N®, Amersham) by electrophoretic blotting (e.g. in 0.025 M sodium phosphate, pH 6.5). In another embodiment, fragments with shifted mobility on SSCA gels are sequenced to determine the exact nature of the polymorphism. Each possibility represents a separate embodiment of the present invention.

In another embodiment, an approach based on the detection of mismatches between complementary DNA strands is utilized. In another embodiment, clamped denaturing gel electrophoresis (CDGE) (Sheffield V C et al., Identification of novel rhodopsin mutations associated with retinitis pigmentosa by GC-clamped denaturing gradient gel electrophoresis. Am J Hum Genet 49(4):699-706, 1991) is utilized. In another embodiment, heteroduplex analysis (HA) (Dereure O et al, Arch Dermatol 2003, 139(12):1571-5) is utilized.

In another embodiment, chemical mismatch cleavage (CMC) (Grompe, M, et al, (1989), Proc Natl Acad Sci USA 86:5855-5892) is utilized. In another embodiment, the radioactive template for chemical cleavage is generated by an amplification of the wild-type PCR product with radiolabeled primers. The radiolabeled oligonucleotide and the corresponding unlabeled primer are then, in another embodiment, used to reamplify 1 ng of the wild-type PCR product. In another embodiment, the probe and unlabeled target DNA (e.g. mutant or wild-type PCR products) are used to form a heteroduplex. In another embodiment, the strands are allowed to rehybridize (e.g. for 2 hr at 42° C.), and the hybridized DNA is precipitated (e.g. in ice-cold ethanol). In another embodiment, cleavage reactions are performed for each PCR product (e.g. an osmium tetroxide [5 min at 37° C., 0.8% wt/vol] and hydroxylamine reaction [15 min at 37TC, 2.5 M solution] for each strand). After piperidine cleavage, the fragments are analyzed by electrophoresis in a denaturing polyacrylamide gel, followed by autoradiography.

In another embodiment, a protein truncation assay is utilized. In another embodiment, an asymmetric assay is utilized. In another embodiment, 1 of these assays is used to detect a large deletion, duplication, or insertion, or a regulatory mutation that affects transcription or translation of the protein.

In another embodiment, once a mutation is known, an allele specific detection approach (e.g. ASO hybridization) is utilized to rapidly screen large numbers of other samples for that same mutation.

In another embodiment, detection of point mutations is accomplished by molecular cloning of the C1qRP allele(s) and sequencing the allele(s) using techniques well known in the art. In another embodiment, the gene sequences are amplified directly from a genomic DNA preparation from the tissue, using known techniques. The DNA sequence of the amplified sequences is then determined.

In another embodiment, the presence of a susceptibility allele is confirmed using SSCA. In another embodiment, denaturing gradient gel electrophoresis (DGGE) is utilized, as described in U.S. Pat. No. 5,190,856, incorporated herein by reference. In another embodiment, DGGE detects a difference in migration rates of a mutant sequence compared to a wild-type sequence, using a denaturing gradient gel.

In another embodiment, RNase protection assays are utilized. RNase protection comprises, in another embodiment, cleavage of the mutant polynucleotide into 2 or more smaller fragments.

In another embodiment, ASO hybridization is utilized. In another embodiment, for ASO hybridization, the oligonucleotide probe is designed to be an appropriate length (e.g. about 19 nucleotides long) in order to have a high probability of recognizing a unique sequence. In another embodiment, the polymorphism is positioned near the center of the sequence to maximize thermal instability of mismatch hybridization.

In another embodiment, proteins that recognize nucleotide mismatches (e.g. the *E. coli* mutS protein) are utilized. In another embodiment, the mutS protein binds only to sequences that contain a nucleotide mismatch in a heteroduplex between mutant and wild-type sequences.

In another embodiment, allele-specific PCR is utilized. In another embodiment, primers that hybridize at their 3' ends to a particular C1qRP mutation are used. If the particular C1qRP mutation is not present, an amplification product is not observed. In another embodiment, Amplification Refractory Mutation System (ARMS) is utilized. In another embodiment, the primer is synthesized in 2 forms. The "normal" form is refractory to PCR on mutant template DNA, and the "mutant" form is refractory to PCR on normal DNA. In another embodiment, if a single 3'-mismatched base allows amplification to proceed, additional mismatches are introduced near the 3' end of the primers.

In another embodiment, insertions and deletions of genes are detected by cloning, sequencing and amplification. In another embodiment, restriction fragment length polymorphism (RFLP) probes for the gene or surrounding marker genes are used to score alteration of an allele or an insertion in a polymorphic fragment. In another embodiment, this method is utilized for screening relatives of an affected individual for the presence of the C1qRP mutation found in that individual.

In another embodiment, DNA probes are used to detect mismatches, through enzymatic or chemical cleavage. In another embodiment, hydroxylamine is utilized. In another embodiment, 2.5 M of hydroxylamine is added for 37°, 2 hours (h). In another embodiment, osmium tetroxide is utilized. In another embodiment, 4% osmium tetroxide in 1 mM EDTA, 10 mM Tris-HCl (pH 7.7) ("TE buffer), and 1.5% (vol/vol) pyridine is added. In another embodiment, chemical cleavage of C and T bases that react with hydroxylamine or osmium tetroxide is achieved by incubating the heteroduplexes with piperidine (e.g. 1 M, 90° C., 30 min).

In another embodiment, mismatches are detected by shifts in the electrophoretic mobility of mismatched duplexes relative to matched duplexes. In another embodiment, with either riboprobes or DNA probes, the cellular mRNA or DNA suspected of containing a polymorphism is amplified by PCR before hybridization. In another embodiment, changes in the C1qRP gene are detected using Southern hybridization. In another embodiment, Southern hybridization is used to detect gross rearrangements, such as deletions and insertions.

In another embodiment, DNA containing the C1qRP gene is amplified by PCR and screened using allele-specific probes. In another embodiment, the probes are nucleic acid oligomers, each of which contains a region of the C1qRP gene sequence harboring a known mutation. In another embodiment, each oligomer corresponds to a portion of the C1qRP gene sequence. By use of a battery of such allele-specific probes, PCR amplification products are screened to identify the presence of a previously identified mutation in the C1qRP gene. Hybridization of allele-specific probes with amplified C1qRP sequences is performed, in another embodiment, on a nylon filter. In another embodiment, hybridization to a particular probe under high stringency hybridization conditions indicates the presence of the same mutation in the tissue as in the allele-specific probe.

In another embodiment, genomic C1qRP sequences from disease patients are directly compared with a control population. In another embodiment, messenger RNA (mRNA) is sequenced after amplification, thereby eliminating the necessity of determining the exon structure of the candidate gene.

"Mismatches" refers, in another embodiment, to hybridized nucleic acid duplexes wherein the 2 strands are not 100% complementary. Lack of total homology is due, in other embodiments, to a deletion, insertion, inversion, or substitution. In another embodiment, mismatch detection is used to detect point mutations in the gene or its mRNA product. An example of a mismatch cleavage technique is the RNase protection method. In another embodiment, a labeled riboprobe complementary to the human wild-type C1qRP gene coding sequence is utilized. The riboprobe and either mRNA or DNA isolated from the tumor tissue are annealed (hybridized) together and subsequently digested with RNase A, which is able to detect some mismatches in a duplex RNA structure. If a mismatch is detected by RNase A, it cleaves at the site of the mismatch. In another embodiment, when the annealed RNA preparation is separated on an electrophoretic gel matrix, an RNA product is seen that is smaller than the full-length duplex RNA for the riboprobe and the mRNA or DNA. The riboprobe need not be, in another embodiment, the full length of the C1qRP mRNA or gene but can be a segment of either. In another embodiment, if the riboprobe covers only a segment of the C1qRP mRNA or gene, a number of these probes are used to screen the whole mRNA sequence for mismatches.

In another embodiment, primer pairs described herein and used in the methods provided, are utilized for determination of the nucleotide sequence of a particular C1qRP allele using PCR. The pairs of single-stranded DNA primers are annealed, in another embodiment, to sequences within or surrounding the C1qRP gene, in order to prime amplifying DNA synthesis of the C1qRP gene itself. A complete set of these primers makes possible, in another embodiment, synthesis of all of the nucleotides of the C1qRP gene coding sequences, i.e., the exons. In another embodiment, synthesis of both intron and exon sequences is performed.

In another embodiment, to facilitate subsequent cloning of amplified sequences, restriction enzyme site sequences are appended to their 5' ends of primers. In another embodiment, primers are designed based on the sequences of the C1qRP exons and alternate exons.

The nucleic acid probes described herein and used in the methods provided, are utilized, in another embodiment, in Southern hybridization to genomic DNA. In another embodiment, the probes are utilized in an RNase protection method for detecting point mutations. In another embodiment, the probes are used to detect PCR amplification products. In another embodiment, the probes are used to detect mismatches with the C1qRP gene or mRNA using other techniques. Each possibility represents another embodiment of the present invention.

In another embodiment, mutations from disease patients falling outside the coding region of C1qRP are detected by examining the non-coding regions, such as introns and regulatory sequences near or within the C1qRP gene. In another embodiment, Northern blotting of mRNA of abnormal size or abundance is found in disease patients, indicating that either noncoding regions play a role in disease etiology or a mutation in another protein, which regulates expression of C1qRP, is involved.

C1qRP mRNA expression is detected, in another embodiment, by Northern blot analysis. In another embodiment, PCR amplification is utilized. In another embodiment, RNase protection is utilized. Diminished or increased mRNA expression indicates an alteration of the wild-type C1qRP gene. In another embodiment, alteration of C1qRP genes is detected by screening for alteration of wild-type C1qRP protein. In another embodiment, monoclonal antibodies immunoreactive with C1qRP are used to screen a tissue. In another embodiment, antibodies specific for products of mutant alleles are used to detect a mutant C1qRP gene product. In another embodiment, Western blots are utilized. In another embodiment, immuno-histochemical assays are utilized. In another embodiment, ELISA assays are utilized. In another embodiment, a functional assay is utilized. In another embodiment, an assay that detects C1qRP biochemical function is utilized. In another embodiment, any other technique known in the art for determining gene expression is utilized. Each possibility represents another embodiment of the present invention.

Nucleic Acid Diagnosis and Diagnostic Kits

In another embodiment, to detect the presence of a C1qRP allele predisposing an subject to diabetes, a biological sample such as blood is prepared and analyzed for the presence or absence of predisposing alleles of C1qRP. In another embodiment, the subject is also tested for diabetes. Diabetes tests are well known in the art, and are described, for example, in U.S. Pat. No. 5,800,998. In another embodiment, any diabetes test known in the art is utilized. Each possibility represents a separate embodiment of the present invention.

In another embodiment, a screening method for a C1qRP polymorphism comprises amplification of the relevant C1qRP sequences. In another embodiment, the screening method involves a non-PCR based strategy. In another embodiment, the screening method includes a two-step label amplification methodology. Two-step label amplification methodologies are well known in the art. Both PCR and non-PCR based screening strategies can detect target sequences with a high level of sensitivity. Each possibility represents a separate embodiment of the present invention.

In another embodiment, target amplification is utilized. Here, the target nucleic acid sequence is amplified with polymerases. In another embodiment, polymerase chain reaction (PCR) is utilized. PCR and other polymerase-driven amplification assays can achieve, in another embodiment, over a million-fold increase in copy number through the use of polymerase-driven amplification cycles. In another embodiment, the, the resulting amplified nucleic acid is sequenced or used as a substrate for DNA probes. Each possibility represents a separate embodiment of the present invention.

In another embodiment, when probes are used to detect the presence of the target sequences, the biological sample to be analyzed, is treated to extract the nucleic acids. In another embodiment, the sample is blood. In another embodiment, the sample is serum. In another embodiment, the sample is any other type of biological sample known in the art. In another embodiment, the sample nucleic acid is prepared to facilitate detection of the target sequence. In another embodiment, the preparation comprises denaturation. In another embodiment, the preparation comprises restriction digestion. In another embodiment, the preparation comprises electrophoresis. In another embodiment, the preparation comprises dot blotting. In another embodiment, the targeted region of the analyte nucleic acid is prepared to be at least partially single-stranded to form hybrids with the targeting sequence of the probe. In another embodiment (e.g. wherein the sequence is naturally single-stranded), denaturation is not required. Methods for DNA denaturation can be carried out by various techniques known in the art. Each possibility represents a separate embodiment of the present invention.

In another embodiment, analyte nucleic acid and probe are incubated under conditions that promote stable hybrid formation of the target sequence in the probe with the putative targeted sequence in the analyte. In another embodiment, the region of the probes used to bind to the analyte is made completely complementary to the targeted region. In another embodiment, the probes are complementary to a region(s) of the chromosome unique in the genome. In another embodiment, high stringency conditions are used in order to prevent false positives. The stringency of hybridization is determined, in another embodiment, by a number of factors during hybridization and during the washing procedure, including temperature, ionic strength, base composition, probe length, and concentration of formamide. These factors are well known in the art, and are described, for example, Molecular Cloning: A Laboratory Manual, eds. J. Sambrook, E. F. Fritsch, T. Maniatis Cold Spring Harbor Laboratory Press, NY (1989). In another embodiment, higher order hybrids, such as triplexes, quadraplexes, etc, are utilized to detect target sequences. Each possibility represents a separate embodiment of the present invention.

In another embodiment, the resulting hybrid is usually detected by the use of labeled probes. In another embodiment, the probe is unlabeled and is detectable by specific binding with a ligand that is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies and the like. Variations of this basic scheme are known in the art, and include those variations that facilitate separation of the hybrids to be detected from extraneous materials and/or that amplify the signal from the labeled moiety. These methods are well known in the art, and are described in, for example, Matthews and Kricka (1988). Anal. Biochem. 169:1; Landegren U, Kaiser R, et al, Science 1988; 242(4876):229-37; Mittlin (1989) Clinical Chem 35:1819; U.S. Pat. No. 4,868,105; and EPO Publication No. 225,807. Each possibility represents a separate embodiment of the present invention.

In another embodiment, for non-PCR based screening assays utilized in the present invention, a nucleic acid probe (or an analog such as a methyl phosphonate backbone replacing the normal phosphodiester) is hybridized to the low level DNA target. In another embodiment, the probe has an enzyme covalently linked thereto, such that the covalent linkage does not interfere with the specificity of the hybridization. In another embodiment, the enzyme-probe-conjugate-target nucleic acid complex is isolated away from the free probe enzyme conjugate, and a substrate is added for enzyme detection. Enzymatic activity is observed, in another embodiment, as a change in color development or luminescent output resulting in a $10^3$-$10^6$ increase in sensitivity. Oligodeoxynucleotide-alkaline phosphatase conjugates and their use as hybridization probes are well known in the art, and are described, for example, in Jablonski, E., et al. (1986). Nuc. Acids Res. 14:6115-6128. Each possibility represents a separate embodiment of the present invention.

Two-step label amplification methodologies are known in the art. These assays work on the principle that a small ligand (such as digoxigenin, biotin, or the like) is attached to a nucleic acid probe capable of specifically binding C1qRP.

In another embodiment, a small ligand attached to a nucleic acid probe is specifically recognized by an antibody-enzyme conjugate. In another embodiment, digoxigenin is attached to the nucleic acid probe. Hybridization is detected by an antibody-alkaline phosphatase conjugate which turns over a chemiluminescent substrate. Methods for labeling nucleic acid probes are well known in the art, and are described, for example, in Martin et al., 1990. In another embodiment, the small ligand is recognized by a second ligand-enzyme conjugate that is capable of specifically complexing to the first ligand. In another embodiment, a biotin-avidin type interaction is utilized. Methods for labeling nucleic acid probes and their use in biotin-avidin based assays are well known in the art, and are described, for example, in Rigby, P. W. J., et al. (1977). J. Mol. Biol. 113:237-251 and Nguyen, Q, et al. (1992). BioTechniques 13:116-123. Each possibility represents a separate embodiment of the present invention.

In another embodiment, a nucleic acid probe assay of this invention employs a cocktail of nucleic acid probes capable of detecting C1qRP. In another embodiment, more than one probe complementary to C1qRP is employed. In another embodiment, 2, 3, 4, 5, or more different nucleic acid probe sequences are utilized. In another embodiment, to detect the presence of mutations in the C1qRP gene sequence in a patient, more than 1 probe complementary to C1qRP is employed, wherein the cocktail includes probes capable of binding to the allele-specific mutations identified in populations of patients with alterations in C1qRP. In another embodiment, the probes correspond to the major gene mutations identified as predisposing an individual to diabetes. Each possibility represents a separate embodiment of the present invention.

Each method and kit represents a separate embodiment of the present invention.

Methods of Use: Peptide Diagnosis and Diagnostic Kits

In another embodiment, susceptibility to diabetes is be detected on the basis of the alteration of wild-type C1qRP polypeptide. In another embodiment, peptide alterations are determined by sequence analysis in accordance with conventional techniques. In another embodiment, antibodies (polyclonal or monoclonal) are used to detect differences in, or the absence of, C1qRP peptides. Methods for preparing, raising, and purifying antibodies are well known in the art. In another embodiment, antibodies are immunoprecipitate C1qRP proteins or fragments of the C1qRP protein from solution. In another embodiment, the antibodies react with C1qRP peptides on Western or immunoblots of polyacrylamide gels. In another embodiment, antibodies detect C1qRP proteins and protein fragments in paraffin or frozen tissue sections, using immunocytochemical techniques. Each possibility represents a separate embodiment of the present invention.

In another embodiment, provided herein is compounds that are agonists of a normal (functional) C1qRP bioactivity and their use in preventing or treating diabetes. In another embodiment, to ameliorate disease symptoms involving insufficient expression of a C1qRP gene and/or inadequate amount of functional C1qRP bioactivity in a subject, a gene therapeutic (comprising a gene encoding a functional C1qRP protein) or a protein therapeutic (comprising a functional C1qRP protein or fragment thereof is administered to the subject. In another embodiment, a C1qRP agonist is administered. In another embodiment, a receptor for C1qRP or fragments thereof is administered. Each possibility represents a separate embodiment of the present invention.

In another embodiment, a peptide having C1qRP activity is supplied to cells that lack CE93 or carry mutant C1qRP alleles. Methods for peptide therapy are well known in the art, and are described, for example, in U.S. Pat. Nos. 5,800,998 and 5,891,628. Each possibility represents a separate embodiment of the present invention.

In another embodiment, a recombinant peptide or protein is produced by expression of the cDNA sequence in bacteria. In another embodiment, an expression vector is utilized. In another embodiment, a C1qRP polypeptide is extracted from C1qRP-producing mammalian cells. In another embodiment, synthetic chemistry is employed to synthesize C1qRP protein. In another embodiment, the resulting preparation is substantially free of other human proteins. Each possibility represents a separate embodiment of the present invention.

In another embodiment, active C1qRP molecules (e.g. peptides, proteins, or mimetics) are introduced into cells using liposomes. In another embodiment, microinjection is utilized. In another embodiment, active molecules are actively taken up by cells. In another embodiment, active molecules are taken up by diffusion. In another embodiment, supply of molecules with C1qRP activity leads to partial reversal of the diabetic phenotype. In another embodiment, a method of present invention further comprises administration of another compound that stimulates or substitutes for C1qRP activity, e.g. a peptide, drug, or organic compound. In another embodiment, a C1qRP mimetic is utilized. Each possibility represents a separate embodiment of the present invention.

In another embodiment, wild-type C1qRP function is supplied to a cell which lacks a C1qRP gene or carries 1 or more mutant C1qRP alleles. In another embodiment, the wild-type C1qRP gene or fragment thereof is introduced into the cell in an extrachromosomal vector. In another embodiment, the wild-type C1qRP gene or fragment thereof is introduced into the mutant cell in such a way that it recombines with the endogenous mutant C1qRP gene present in the cell. Such recombination requires, in another embodiment, a double recombination event that results in the correction of the C1qRP gene mutation.

In another embodiment, an antibody utilized in a method described herein and used in the methods provided, is a polyclonal antibody. In another embodiment, the antibody is a monoclonal antibody. In another embodiment, the antibody is an Fab fragment. In another embodiment, the antibody is an F(ab')$_2$ fragment. In another embodiment, the antibody is a single chain antibody. In another embodiment, the antibody is a chimeric antibody. In another embodiment, the antibody is a humanized antibody. Each possibility represents a separate embodiment of the present invention.

In another embodiment, an antagonist of a physiological process that stimulates or increases C1qRP bioactivity is utilized to prevent or treat diabetes. In another embodiment, an antagonistic antibody specific for mutant C1qRP gene product is utilized.

In another embodiment, an antisense nucleic acid molecule is administered. In another embodiment, a ribozyme antagonist is administered. In another embodiment, a triplex antagonist is administered. In another embodiment, an anti-C1qRP antibody is administered. Each possibility represents a separate embodiment of the present invention.

In another embodiment, the antagonist is an antisense, ribozyme, or triple helix molecule. Techniques for the production of antisense, ribozyme, and triple helix molecules and use of such molecules are well known to those of skill in the art, such as described herein or in U.S. Pat. No. 5,800,998, incorporated herein by reference. In another embodiment, the antagonist reduces or prevents gene expression. In another embodiment, to ameliorate disease symptoms involving the regulation via a C1qRP protein, a C1qRP protein fragment, or an upstream or downstream element in a C1qRP mediated biochemical pathway (e.g. signal transduction), a therapeutically effective amount of an agonist or antagonist compound (e.g. small molecule, peptide, peptidomimetic, protein or antibody) is utilized to induce a therapeutic effect. Each possibility represents a separate embodiment of the present invention.

In another embodiment, provided herein is a method of treating a diabetes in a subject, comprising the step of contacting the subject with an agonist of a ligand of a C1qRP protein or a protein that interacts with a C1qRP protein. In another embodiment, the ligand or interacting protein is an EGF family member. In another embodiment, the ligand or interacting protein is any other protein known in the art that interacts with a C1qRP protein. Each possibility represents a separate embodiment of the present invention.

"Ribozymes" refers, in another embodiment, to enzymatic RNA molecules capable of catalyzing the specific cleavage of RNA. The mechanism of ribozyme action involves sequence specific hybridization of the ribozyme molecule to complementary target RNA, followed by an endonucleolytic cleavage. The composition of ribozyme molecules includes, in another embodiment, 1 or more sequences complementary to the target C1qRP mRNA, preferably the mutant C1qRP mRNA, and the catalytic sequence responsible for mRNA cleavage, as described, for example, in U.S. Pat. No. 5,093,246, which is incorporated by reference herein in its entirety. In another embodiment, engineered hammerhead motif ribozyme molecules are utilized that specifically and efficiently catalyze endonucleolytic cleavage of RNA sequences encoding C1qRP. In another embodiment, the targets are preferably mutant C1qRP proteins. Each possibility represents a separate embodiment of the present invention.

Specific ribozyme cleavage sites within any potential RNA target are initially identified, in another embodiment, by scanning the target molecule for ribozyme cleavage sites that include the following sequence: GUA, GUU and GUC. Once identified, short RNA sequences of between 15 and ribonucleotides corresponding to the region of the target gene containing the cleavage site are evaluated for predicted structural features, such as secondary structure, that may render the oligonucleotide sequence unsuitable. The suitability of candidate targets is evaluated, in another embodiment, by testing their accessibility to hybridization with complementary oligonucleotides, using ribonuclease protection assays. Each possibility represents a separate embodiment of the present invention.

Triplex helix formation utilizes, in another embodiment, nucleic acid molecules that are single stranded and composed of deoxynucleotides. The base composition of these oligonucleotides is designed to promote triple helix formation via Hoogsteen base pairing rules, which generally require sizeable stretches of either purines or pyrimidines to be present on 1 strand of a duplex. In another embodiment, the nucleotide sequences are pyrimidine-based, which results in TAT and CGC$^+$ triplets across the 3 associated strands of the resulting triple helix. The pyrimidine-rich molecules provide base complementarity to a purine-rich region of a single strand of the duplex in a parallel orientation to that strand. In another embodiment, purine-rich nucleic acid molecules are chosen. In another embodiment, the molecules contain a stretch of guanidine residues. These molecules will form a triple helix with a DNA duplex that is rich in GC pairs, in which the majority of the purine residues are located on a single strand of the targeted duplex, resulting in GGC triplets across the 3 strands in the triplex. Each possibility represents a separate embodiment of the present invention.

In another embodiment, the potential sequences that can be targeted for triple helix formation are increased by creating a so called "switchback" nucleic acid molecule. Switchback molecules are synthesized in an alternating 5'-3', 3'-5' manner, such that they base pair with one strand of a duplex first and then the other, eliminating the necessity for a sizeable stretch of either purines or pyrimidines to be present on one strand of a duplex.

In another embodiment, the antisense, ribozyme, and/or triple helix molecules described herein reduce or inhibit translation of mRNA produced by both normal and mutant C1qRP alleles. In another embodiment, to ensure that substantial normal levels of C1qRP activity are maintained in the cell, nucleic acid molecules that encode and express C1qRP polypeptides exhibiting normal C1qRP activity are introduced into cells that do not contain sequences susceptible to that antisense, ribozyme, or triple helix treatments. In ano these sequences are introduced via gene therapy methods. In another embodiment, normal C1qRP protein is coadministered into the cell or tissue, to maintain the requisite level of cellular or tissue C1qRP activity. Each possibility represents a separate embodiment of the present invention.

Antisense RNA and DNA molecules, ribozyme molecules and triple helix molecules of the invention can be prepared by any method known in the art for the synthesis of DNA and RNA molecules. Techniques for chemically synthesizing oligodeoxyribonucleotides and oligoribonucleotides, including phosphoramidite chemical synthesis and solid phase synthesis, are well known in the art. In another embodiment, RNA molecules are generated by in vitro or in vivo transcription of DNA sequences encoding same. In another embodiment, the DNA sequences are incorporated into a vector that incorporates a suitable RNA polymerase promoter. In another embodiment, an antisense cDNA construct that directs synthesis of antisense RNA is introduced stably into cell lines. In another embodiment, the synthesis is constitutive. In another embodiment, the synthesis is inducible. Each possibility represents a separate embodiment of the present invention.

In another embodiment, a modification is introduced into the DNA molecule as a means of increasing intracellular stability and half-life. In another embodiment, the modifications include addition of flanking sequences of ribo- or deoxy- nucleotides to the 5' and/or 3' ends of the molecule. In another embodiment, the modifications include use of phosphorothioate or 2' O-methyl rather than phosphodiesterase linkages within the oligodeoxyribonucleotide backbone. In another embodiment, any other modification known in the art is utilized. Each possibility represents a separate embodiment of the present invention.

In another embodiment, a method described herein and used in the methods provided, comprises gene therapy. Methods for gene therapy are well known in the art, and are described, for example, in U.S. Pat. Nos. 5,837,492 and 5,800,998, which are incorporated by reference herein. Expression vectors in the context of gene therapy are meant to include those constructs containing sequences sufficient to express a polynucleotide that has been cloned therein. For viral expression vectors, the construct contains, in another embodiment, viral sequences sufficient to support packaging of the construct. In another embodiment, the expression vector further includes sequences, such as selectable markers and other sequences conventionally used. Each possibility represents a separate embodiment of the present invention.

In another embodiment provided herein is a method of screening a test compound to identify compounds therapeutic for diabetes, by testing effect of compounds on an interaction between a C1qRP protein and molecule that binds thereto or interacts therewith. In another embodiment, the method includes the steps of (i) combining a C1qRP polypeptide or bioactive fragment thereof, a C1qRP target molecule, and a test compound, e.g., under conditions wherein, but for the test compound, the C1qRP protein and C1qRP target molecule are able to interact; and (ii) detecting the formation of a complex which includes the C1qRP protein and the target molecule. In another embodiment, the detection comprises directly quantifying the complex. In another embodiment, the detection comprises measuring inductive effects of the C1qRP protein or fragments of C1qRP protein. A statistically significant change, such as a decrease, in the interaction of the C1qRP and C1qRP target molecule in the presence of a test compound (relative to interaction detected in the absence of the test compound) is indicative of a modulation (e.g., inhibition or potentiation of the interaction between the C1qRP protein or fragments of the C1qRP protein and the target molecule). Each possibility represents a separate embodiment of the present invention.

In another embodiment, a wild-type or mutant C1qRP polypeptide or binding fragment thereof is used to screen compounds.

In another embodiment, the C1qRP polypeptide or fragment thereof is free in solution. In another embodiment, the peptide or fragment is affixed to a solid support. In another embodiment, the peptide or fragment is borne on a cell surface. In another embodiment, eukaryotic or prokaryotic host cells are stably transformed with recombinant polynucleotides expressing the polypeptide or fragment, preferably in competitive binding assays. In another embodiment, such cells, either in viable or fixed form, are used for standard binding assays. In another embodiment, formation of complexes between a C1qRP polypeptide or fragment and the agent being tested is measured. In another embodiment, interference of formation of a complex between a C1qRP polypeptide or fragment and a known ligand, e.g. C1qRP receptor (AT1), is tested. Each possibility represents a separate embodiment of the present invention.

In another embodiment, a competitive binding assay is utilized. In another embodiment, the C1qRP polypeptide or fragment is labeled. In another embodiment, free C1qRP polypeptide or fragment is separated from that present in a protein:protein complex, and the amount of free (i.e., uncomplexed) label is a measure of the binding of the agent being tested to C1qRP or its interference with C1qRP:ligand binding, respectively. Each possibility represents a separate embodiment of the present invention.

In another embodiment, high throughput screening is performed to identify compounds having suitable binding affinity to the C1qRP polypeptides. In another embodiment, large numbers of different small peptide test compounds are synthesized on a solid substrate, such as plastic pins or some other surface. The peptide test compounds are reacted with C1qRP polypeptides and washed. Bound C1qRP polypeptides are then detected by methods well known in the art. Methods for high throughput screening are well known in the art. Each method represents a separate embodiment of the present invention.

In another embodiment of the aforementioned drug screening techniques, purified C1qRP is coated directly onto plates. In another embodiment, non-neutralizing antibodies to the polypeptide are used to capture antibodies to immobilize the C1qRP polypeptide on the solid phase. Each possibility represents a separate embodiment of the present invention.

In another embodiment, competitive drug screening assays are utilized, wherein neutralizing antibodies capable of specifically binding the C1qRP polypeptide compete with a test compound for binding to the C1qRP polypeptide or fragments thereof. In another embodiment, the antibodies are used to detect the presence of any peptide which shares one or more antigenic determinants of the C1qRP polypeptide. Each possibility represents a separate embodiment of the present invention.

In another embodiment, the screening assay utilizes host eukaryotic cell lines or cells that express a wild-type or mutant C1qRP gene and accordingly demonstrate a specific phenotype. The phenotype of the cells is examined to determine if the compound is capable of modulating the phenotype and thereby C1qRP function.

In another embodiment, to screen for substances that modulate activity of a polypeptide, 1 or more test substances are contacted with the polypeptide in a suitable reaction medium, then activity of the treated polypeptide is testing and compared with activity of the polypeptide in comparable reaction medium lacking the test substance. A difference in activity between the treated and untreated polypeptides is indicative, in another embodiment, of a modulating effect of the relevant test substance or substances. Each possibility represents a separate embodiment of the present invention.

In another embodiment, prior to or in addition to being screened for modulation of activity, test substances are screened for ability to interact with the polypeptide, e.g., in a yeast two-hybrid system. Methods for yeast two-hybrid systems are well known in the art. This system is used, in another embodiment, as a coarse screen prior to testing a substance for actual ability to modulate activity of the polypeptide. In another embodiment, the screen is used to screen test substances for binding to a C1qRP specific binding partner or to find mimetics of a C1qRP polypeptide. Each possibility represents a separate embodiment of the present invention.

In another embodiment, transcription levels of certain genes in a cell are modulated by modulating C1qRP bioactivity, (e.g., by potentiating or disrupting a C1qRP bioactivity). In another embodiment, the target cell is treated with an effective amount of a C1qRP therapeutic (agonist or antagonist of a C1qRP bioactivity) so as to alter, relative to the cell in the absence of treatment, the level of transcription of certain genes. In another embodiment, the method can be carried out with C1qRP therapeutics, e.g. peptides, peptidomimetics, or other molecules identified in drug screens that agonize or antagonize the effects of a C1qRP bioactivity (e.g. transcription) of a gene regulated by a C1qRP protein. In another embodiment, another C1qRP therapeutic is utilized, e.g. an antisense construct for inhibiting expression of C1qRP proteins or a dominant negative C1qRP mutant that competitively inhibits interactions between ligands (e.g. proteins) and nucleic acids upstream or downstream of the wild-type C1qRP protein. Each possibility represents a separate embodiment of the present invention.

In another embodiment, provided herein is a composition for treating diabetes, the composition comprising a C1qRP-encoding nucleic acid, C1qRP protein or fragment thereof, or C1qRP agonist, antagonist, or inhibitor. Each possibility represents a separate embodiment of the present invention.

In another embodiment, provided herein is a method of increasing the efficacy of an immune response in a subject (e.g. an immune response to a vaccine), the method comprising the step of contacting the subject with a compound or composition that disrupts an immuno-regulatory function of C1qRP protein. In another embodiment, the immuno-regulatory function requires binding to a calcium ion. In another embodiment, the compound or composition disrupts C1qRP protein function by sterically blocking or hindering calcium binding. In another embodiment, immuno-regulatory function is B cell compartment homeostasis. Each possibility represents a separate embodiment of the present invention.

In another embodiment, a C1qRP nucleic acid or protein described herein and used in the methods provided, is homologous to a nucleic acid or protein enumerated, mentioned, or disclosed herein. The terms "homology," "homologous," etc, when in reference to any protein or peptide, refer, in one embodiment, to a percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Methods and computer programs for the alignment are well known in the art.

Homology is, in another embodiment, determined by computer algorithm for sequence alignment, by methods well described in the art. For example, computer algorithm analysis of nucleic acid sequence homology can include the utilization of any number of software packages available, such as, for example, the BLAST, DOMAIN, BEAUTY (BLAST Enhanced Alignment Utility), GENPEPT and TREMBL packages.

In another embodiment, "homology" refers to identity to a sequence selected from SEQ ID No: 1-8 of greater than 62%. In another embodiment, "homology" refers to identity to a sequence selected from SEQ ID No: 1-8 of greater than 72%. In another embodiment, "homology" refers to identity to one of SEQ ID No: 1-8 of greater than 75%. In another embodiment, "homology" refers to identity to a sequence selected from SEQ ID No: 1-8 of greater than 78%. In another embodiment, "homology" refers to identity to one of SEQ ID No: 1-8 of greater than 80%. In another embodiment, "homology" refers to identity to one of SEQ ID No: 1-8 of greater than 82%. In another embodiment, "homology" refers to identity to a sequence selected from SEQ ID No: 1-8 of greater than 83%. In another embodiment, "homology" refers to identity to one of SEQ ID No: 1-8 of greater than 85%. In another embodiment, "homology" refers to identity to one of SEQ ID No: 1-8 of greater than 87%. In another embodiment, "homology" refers to identity to a sequence selected from SEQ ID No: 1-8 of greater than 88%. In another embodiment, "homology" refers to identity to one of SEQ ID No: 1-8 of greater than 90%. In another embodiment, "homology" refers to identity to one of SEQ ID No: 1-8 of greater than 92%. In another embodiment, "homology" refers to identity to a sequence selected from SEQ ID No: 1-8 of greater than 93%. In another embodiment, "homology" refers to identity to one of SEQ ID No: 1-8 of greater than 95%. In another embodiment, "homology" refers to identity to a sequence selected from SEQ ID No: 1-8 of greater than 96%. In another embodiment, "homology" refers to identity to one of SEQ ID No: 1-8 of greater than 97%. In another embodiment, "homology" refers to identity to one of SEQ ID No: 1-8 of greater than 98%. In another embodiment, "homology" refers to identity to one of SEQ ID No: 1-8 of greater than 99%. In another embodiment, "homology" refers to identity to one of SEQ ID No: 1-8 of 100%. Each possibility represents a separate embodiment of the present invention.

In one embodiment, the step of analyzing the biological sample using the methods and kits described herein, comprises contacting the biological sample with an antibody or its fragment, immunoreactive with the mutated CD93 protein, forming an immunocomplex; and comparing the quantity of said immunocomplex to the quantity of immunocomplex formed under identical conditions with the same antibody and a control biological sample from one or more subjects known not to have an autoimmune disease. In one embodiment, the antibody is immunoreactive with a wild type CD93.

Protein and/or peptide homology for any AA sequence listed herein is determined, in another embodiment, by methods well described in the art, including immunoblot analysis, or via computer algorithm analysis of AA sequences, utilizing any of a number of software packages available, via established methods. Some of these packages include the FASTA, BLAST, MPsrch or Scanps packages, and, in another embodiment, employ the use of the Smith and Waterman algorithms, and/or global/local or BLOCKS alignments for analysis, for example. Each method of determining homology represents a separate embodiment of the present invention.

In another embodiment of the present invention, "nucleic acids" or "nucleotide" refers to a string of at least two base-sugar-phosphate combinations. The term includes, in one embodiment, DNA and RNA. "Nucleotides" refers, in one embodiment, to the monomeric units of nucleic acid polymers. RNA is, in one embodiment, in the form of a tRNA (transfer RNA), snRNA (small nuclear RNA), rRNA (ribosomal RNA), mRNA (messenger RNA), anti-sense RNA, small inhibitory RNA (siRNA), micro RNA (miRNA) and ribozymes. The use of siRNA and miRNA has been described (Caudy A A et al, Genes & Devel 16: 2491-96 and references cited therein). DNA can be, in other embodiments, in form of plasmid DNA, viral DNA, linear DNA, or chromosomal DNA or derivatives of these groups. In addition, these forms of DNA and RNA can be single, double, triple, or quadruple stranded. The term also includes, in another embodiment, artificial nucleic acids that contain other types of backbones but the same bases. In one embodiment, the artificial nucleic acid is a PNA (peptide nucleic acid). PNA contain peptide backbones and nucleotide bases and are able to bind, in one embodiment, to both DNA and RNA molecules. In another embodiment, the nucleotide is oxetane modified. In another embodiment, the nucleotide is modified by replacement of one or more phosphodiester bonds with a phosphorothioate bond. In another embodiment, the artificial nucleic acid contains any other variant of the phosphate backbone of native nucleic acids known in the art. The use of phosphothiorate nucleic acids and PNA are known to those skilled in the art, and are described in, for example, Neilsen P E, Curr Opin Struct Biol 9:353-57; and Raz N K et al Biochem Biophys Res Commun. 297:1075-84. The production and use of nucleic acids is known to those skilled in art and is described, for example, in Molecular Cloning, (2001), Sambrook and Russell, eds. and Methods in Enzymology: Methods for molecular cloning in eukaryotic cells (2003) Purchio and G. C. Fareed. Each nucleic acid derivative represents a separate embodiment of the present invention.

In another embodiment, provided herein is a kit comprising a compound or composition utilized in performing a method of the present invention. In another embodiment, provided herein is a kit comprising a composition, tool, or instrument of the present invention. Each possibility represents a separate embodiment of the present invention.

In another embodiment, provided herein is a vector comprising the mutated CD93 gene described herein.

In one embodiment, "contacting" refers to a method of exposure that can be direct or indirect. In one method such contact comprises direct injection of the cell through any means well known in the art, such as microinjection. In another embodiment, supply to the cell is indirect, such as via provision in a culture medium that surrounds the cell, or administration to a subject, or via any route known in the art. In another embodiment, the term "contacting" means that the compound described herein and used in the methods provided, is introduced into a subject receiving treatment, and the active compound is allowed to come in contact with the target receptor in vivo. Each possibility represents a separate embodiment of the present invention.

In another embodiment of the methods of the present invention, an active compound described herein and used in the methods provided, is carried in the subjects' bloodstream to the target cell. In another embodiment, the compound is carried by diffusion to the target cell. In another embodiment, the compound is carried by active transport to the target cell. In another embodiment, the compound is administered to the subject in such a way that it directly contacts the target cell. Each possibility represents a separate embodiment of the present invention.

In another embodiment, the active compound is administered throughout the course of disease (e.g. diabetes). In another embodiment, the compound is administered during symptomatic stages of the disease. In another embodiment, the compound is administered as a pretreatment for prevention of the disease. In another embodiment, the compound is administered as a post-treatment for preventing relapse of the disease. Each possibility represents a separate embodiment of the present invention.

The following examples are presented in order to more fully illustrate the preferred embodiments of the invention. They should in no way be construed, however, as limiting the broad scope of the invention.

EXPERIMENTAL DETAILES SECTION

Materials and Methods
Mice

C57BL/6J, NOD/ShiLtJ, NOR/LtJ, C3H/HeJ, BALB/cJ, NZBWF1/J, MRL/MpJ, B6.NOD$^{Idd13\text{-}(D2Mit274\text{-}D2Mit343)}$ (Jax #3046), NOD.B6$^{Idd13\text{-}(D2Mit490\text{-}Ada)}$ (Jax #2346), NOD.B6$^{Idd13\text{-}(Zfp106\text{-}111a)}$ (Jax #3050), and NOD.B6$^{Idd13\text{-}(111a\text{-}Pcna)}$ (Jax#3051) mice were obtained from Jackson Laboratories (Bar Harbor, Me.). CD93−/− mice were donated. All animals used in the described experiments were between 5 and 16 weeks old and were housed in specific pathogen free conditions at the University of Pennsylvania Medical Center. Animal procedures were in accordance with the Animal Welfare Act.

Abs and Flow Cytometric Analysis

The antibodies used in this study were as follows: PerCP conjugated anti-CD45R (B220, RA3-6B2), APC conjugated anti-IgM (II/41), FITC/PE conjuagated anti-CD21/35 (7G6) PE conjugated anti-AA4.1, biotinilated 493 mAb (BD Bioscieces, San Diego, Calif.), mAb1696 (R&D systems, Minneapolis, Minn.), and anti-Rat IgG2b (RG7/11.1) (BD Biosciences). Biotinylated mAb were detected by streptavidin-allophycocanin (BD Biosences). A total of 1-2×10⁶ splenocytes, BM or PBL derived cells from age and sex matched mice were surface stained in 96-well microtiter plates with various combinations of the previously described antibodies. FACS analysis was performed using a FACSCalibur (BD Biosciences, San Jose, Calif.) and the data were analyzed using FlowJo Software (version 8, Tree Star, Inc, Ashland, Oreg.).

Immunohistochemistry

For immunohistochemical staining, bone marrow from representative NOD and B6 mice were snap frozen and sectioned. Tissue sections were then single stained with AA4.1 and counterstained with Heamatoxylin.

Bone Marrow Derived Macrophages

Bone marrow derived macrophages were prepared from bone marrow progenitors. Briefly, bone marrow was flushed from femurs of 5 or 10 week-old mice and plated in cell culture dishes with Dulbecco's modified Eagle's medium (DMEM; Invitrogen, San Diego, Calif.) supplemented with 15% L929 cell-conditioned medium (as a source of M-CSF), 10% heat inactivated FCS, 100 units/ml penicillin/streptomycin (Invitrogen), and 10 mM HEPES. Additional media was added on day 4, and cells were incubated at 37° C. in 5% CO2 for 7-8 days until uniform layers of macrophages were established.

sCD93 ELISA

Blood was collected by cardiac puncture, placed on ice, centrifuged for 10 min at 3200 rpm at 4° C., then serum was stored at −70° C. until use. Mouse serum was assayed for soluble CD93 using CD93 sandwich ELISA. Briefly, Immulon 2 HB plates (Thermo Labsystems, Franklin, Mass.) were coated overnight at 4° C. with 2 □g/ml rat monoclonal anti-mouse CD93 (mAB 1696, R&D Systems, Minneapolis, Minn.) in 0.1 M carbonate buffer, pH 7.4, washed with phosphate buffer saline (PBS) containing 0.05% Tween-20 (PBST), and blocked with PBST containing 3% dried milk (block buffer) for 1 hr. Diluted serum samples were added to wells and incubated for 1 hr. After washing with PBST, 1 □g/ml sheep anti-mouse CD93 antibody (AF1696, R&D Systems) was added to wells for 1 hr followed by incubation with anti-sheep horseradish peroxidase-conjugated streptavidin (Jackson, Immunoresearch, West Grove, Pa.) diluted 1:2,000 in 1% dried milk. Sigma fast 0-phenylenediamine dihydrochloride peroxidase substrate (Sigma) was added and the change in absorbance at 405 nm was measured.

Western Blot

For western blot analysis, bone marrow derived macrophages were harvested into lysis buffer (50mM HEPES, pH 7.0, 150 mM NaCl, 10% glycerol, 1.2% Triton X-100, 1.5 mM MgCl$_2$, 10 mM sodium pyrophosphate, 100 mM NaF, 1.25 mM sodium orthovanadate, and 1 mM phenylmethylsulfonyl fluoride plus 0.15 units/ml aprotinin, 10 □g/ml leupeptin, 10 □g/ml pepstatin A) and incubated on ice for 30 min. After incubation, lysates were centrifuged at 14,000×g for 10 min. The supernatants were collected, and protein concentrations were determined using the BCA kit (Pierce Biotechnology, Rockford, Ill.). Soluble cell extracts were then separated by 8% SDS-PAGE and then transferred to polyvinylidene difluoride (PVDF). The membrane was blocked overnight with 5% dry milk in TBST (0.05% Tween-20 in 20 mM Tris, pH 7.4, 150 mM NaCl) and blots were probed for 2 h at room temperature with polyclonal anti-CD93 cytoplasmic tail Ab 1150 generated against C-terminal 11 aa of CD93. Blots were washed and probed with secondary HRP-conjugated for 1 h at room temperature and developed using ECL (Amersham Biosciences).

PCR Amplification and Genomic Sequencing

Genomic DNA was obtained from lysed tails. The CD93 gene was PCR amplified from genomic DNA using primers designed from the published cDNA sequence. The forward oligonucleotide used was 5'-ATGGCCATCTCAACTG-GTTT-3' (Seq Id No. 9) and the reverse oligonucleotide used was 5'-TCAGCAGTCTGTCCCTGGTG-3' (Seq Id No. 10). The PCR product of 1,835 by was isolated on an agarose gel. The bands were cut and purified DNA was extracted using the QIAGEN QIAquick Gel Extraction kit. Samples were sent for sequencing at the University of Pennsylvania School of Medicine DNA Sequencing Facility.

EXAMPLE 1

Figure 1B:
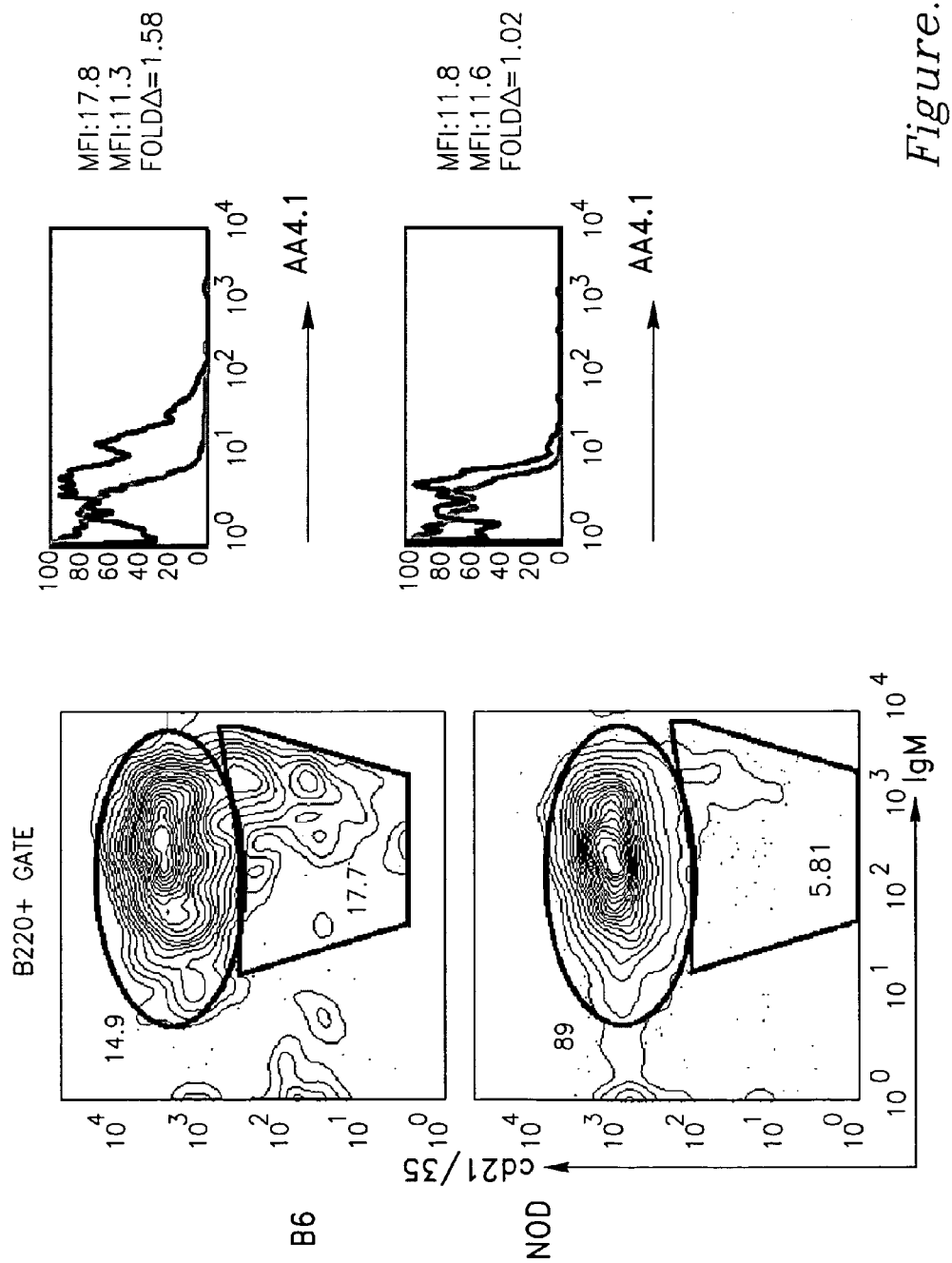
Figure 1C:
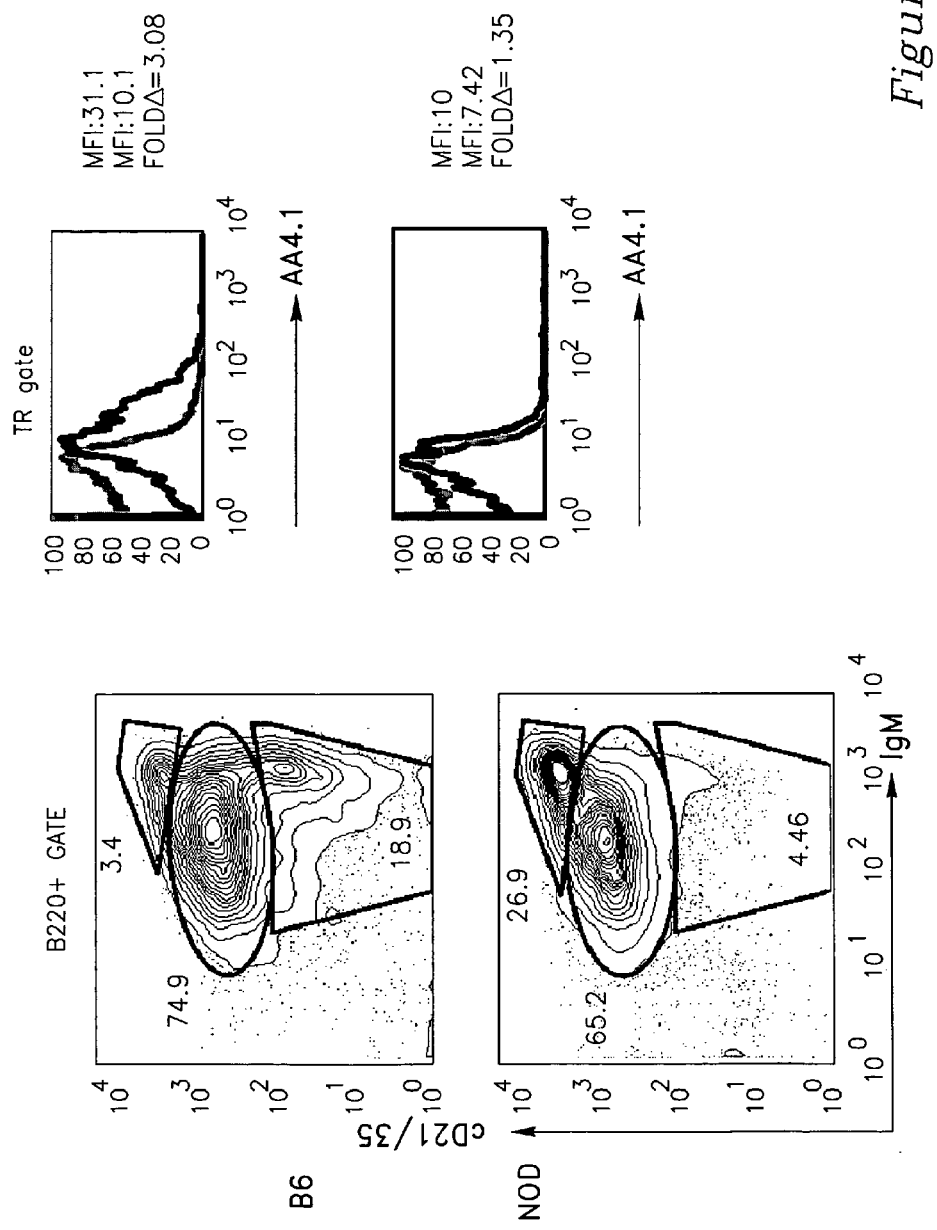
Figure 2:
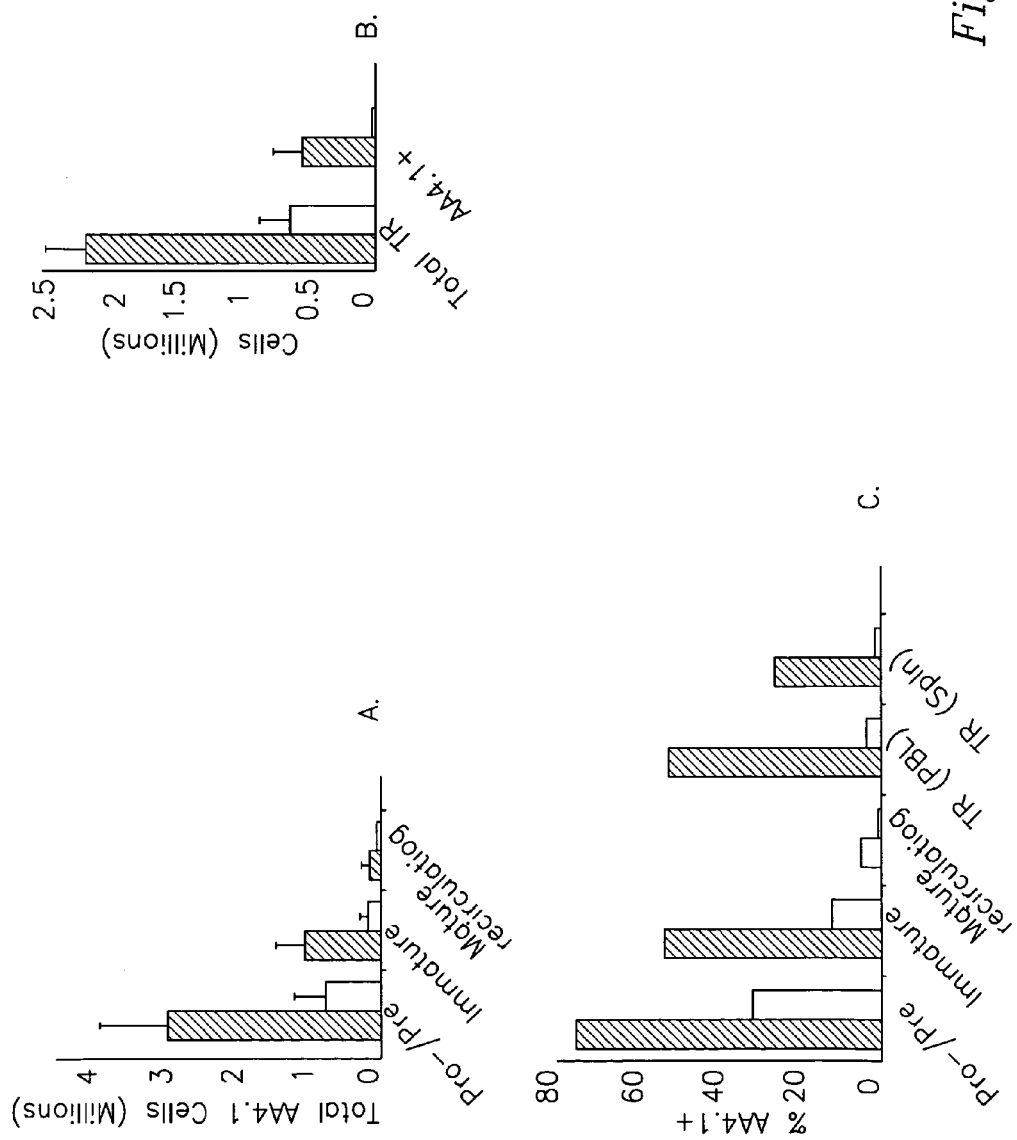
FIGS. 2A-C show the absolute number (panels A and B) and percentage (panel C) of AA4.1+cells in various B cell developmental subsets.
Figure 3A:
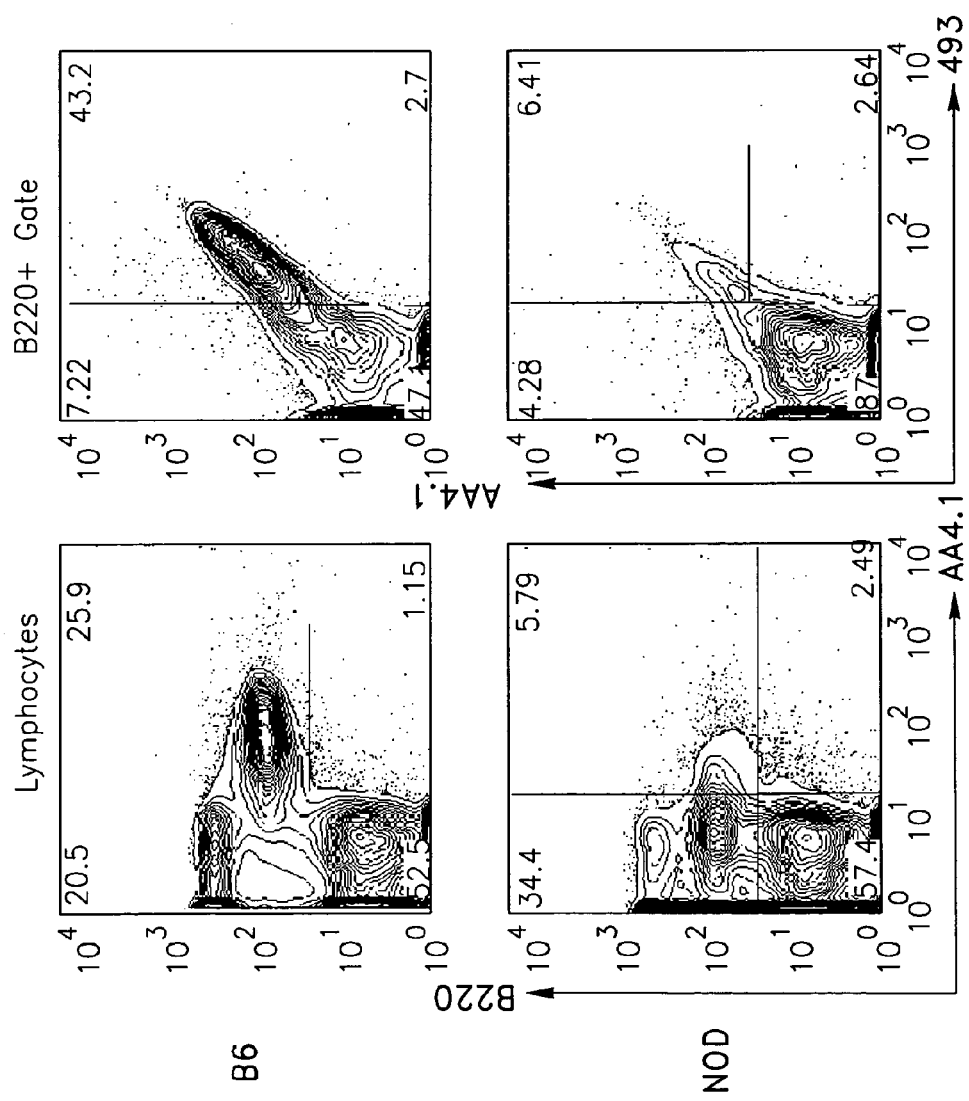
FIGS. 3A-C show flow cytometric (panels A and B) and immunohistochemical staining (panel C) of CD93 in B cell developmental subsets.
Figure 3B:
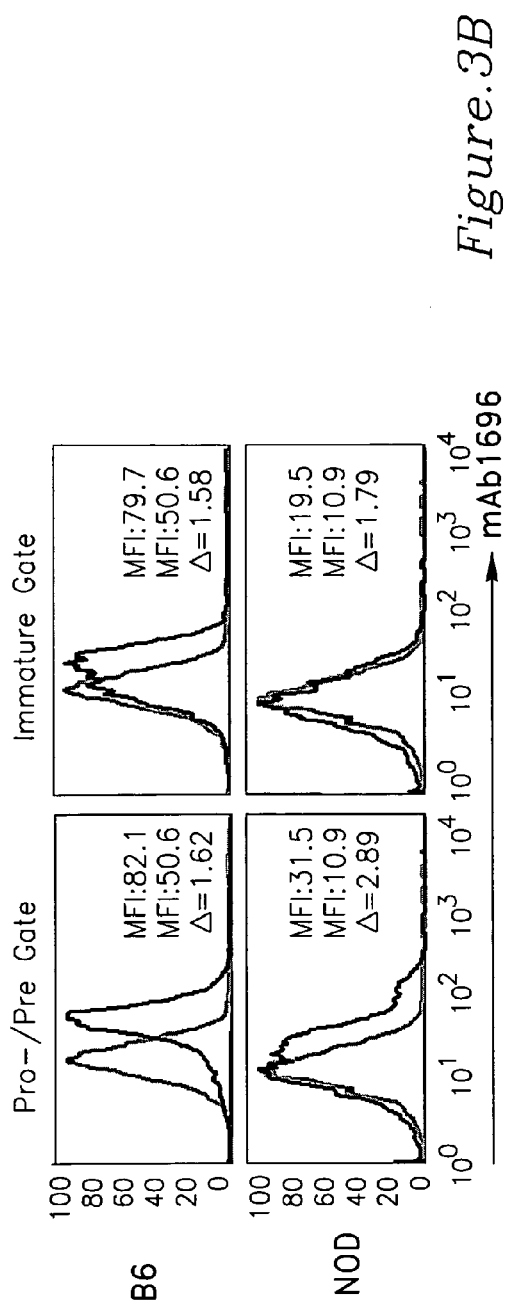
Figure 3C:
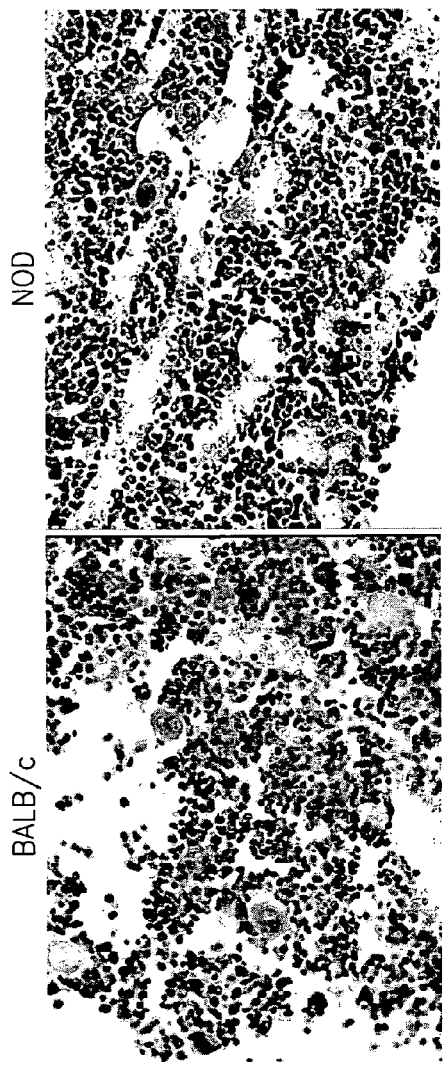

CD93 Expression by Pro-/Pre-, Immature and Transitional B Cells is Deficient in NOD Mice The expression of CD93 on the various B cell developmental subsets was characterized using a flow cytometric gating scheme. In the BM, we resolved the Pro-/Pre-, immature and mature recirculating B cell subsets based on their expression of IgM and B220(FIG. 1, panel A). The $B220^{Low}/IgM^{Negative}$ gate contains Pro- and Pre-B cells, the $B220^{Low}/IgM^{Positive}$ gate contains immature B cells and the $B220^{High}/IgM^{Positive}$ gate contains mature/recirculating B cells. In the peripheral blood and spleen we resolved the transitional (TR) B cell compartment using a $B220^{Low}/IgM^{Positive}/CD21^{Low}$ gate and the Mature/Follicular subset using a $B220^{High}/IgM^{Positive}/CD21^{Positive}$ gate (FIG. 1, panel B). CD93 is routinely used as an early B cell developmental marker in non-autoimmune strains of mice { Cancro, 2004 #2}. In C57BL/6 (B6) mice CD93 is expressed at high levels on Pro-/Pre- and immature B cell progenitors in the BM (FIG. 1, panel A). Its expression continues on peripheral blood and splenic TR B cells; albeit at a lower level than that seen on B cell progenitors in the BM (FIG. 1). On the other hand, characterization of CD93 expression using the various B cell developmental subsets in NOD mice revealed a deficiency in its expression by Pro-/Pre-, immature and TR B cells in the BM, peripheral blood and splenic compartments (FIG. 1). Overall, cell surface staining of CD93 using the AA4.1 mAb revealed a 5-10 fold reduced expression on the surface of early NOD B cell progenitors, as compared to their B6 counterparts (FIG. 1C). Both the absolute number and proportion of CD93+ B cells (i.e., AA4.1+) was drastically reduced in all early B cell developmental subsets (FIG. 2). Three distinct mAbs were used to quantify the cell surface expression of CD93 in NOD versus B6 mice (FIG. 3, panels a and b). AA4.1, 493 and 1696 are known to bind CD93. AA4.1,493 and 1696 staining are deficient in B cell progenitors of NOD mice as compared to their B6 counterparts (FIG. 3). Moreover, in agreement with flow cytometry results presented herein, immunohistochemical staining of BM revealed an absence of AA4.1 staining in the BM of NOD, but not B6, mice (FIG. 3, panel C).

EXAMPLE 2

The NOD CD93 Defect Maps to Idd13

Figure 4A:
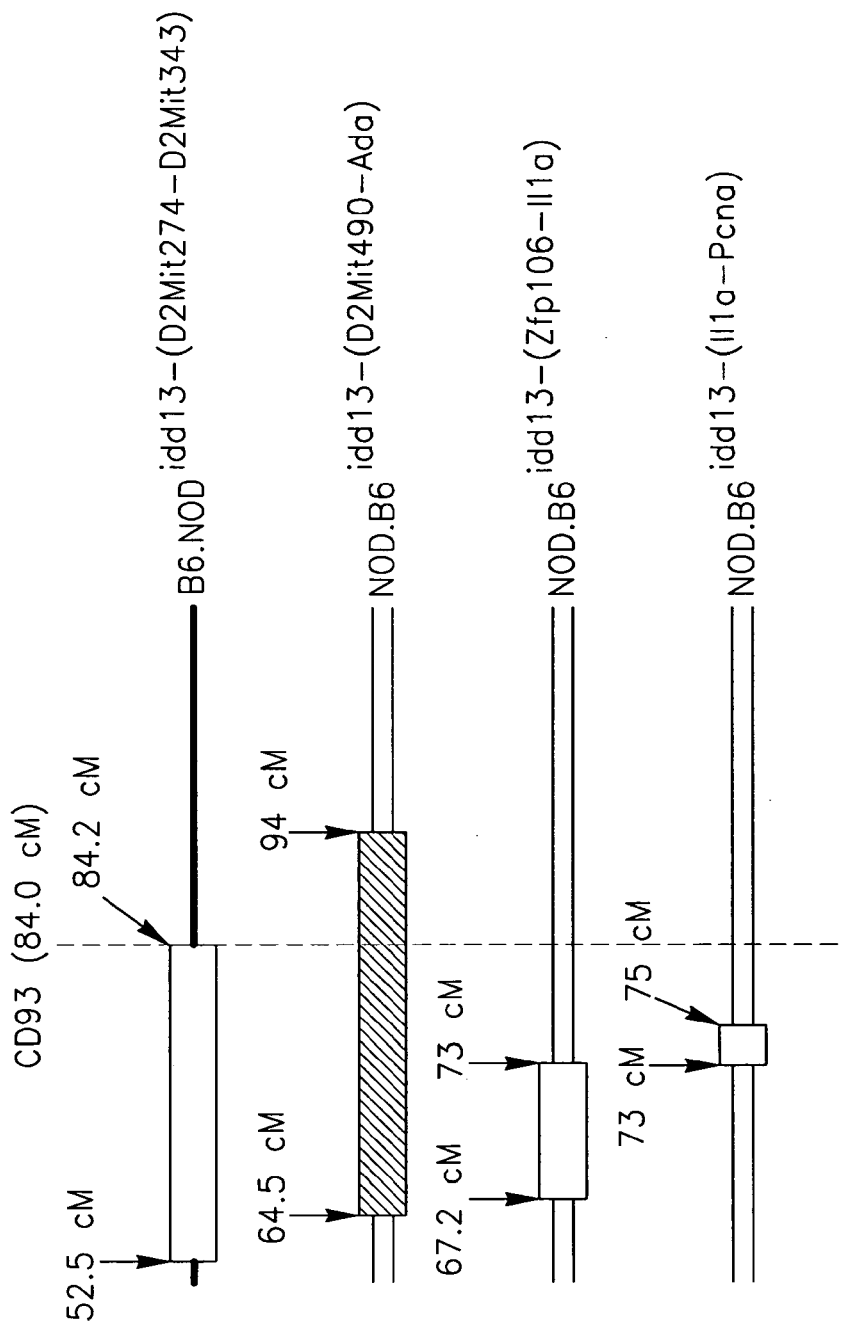
FIGS. 4A-B show that the NOD CD93 defect maps to Idd13. Panel A summarizes the chromosomal regions introgressed from either the B6 or NOD strains onto the NOD and B6 backgrounds for each Idd13 congenic strain, respectively. Panel B shows that early B cell progenitors from these Idd13 subcongenic strains are deficient in CD93 expression as compared to B6 wild-type counterparts, similarly to NOD wild-type mice
Figure 4B:
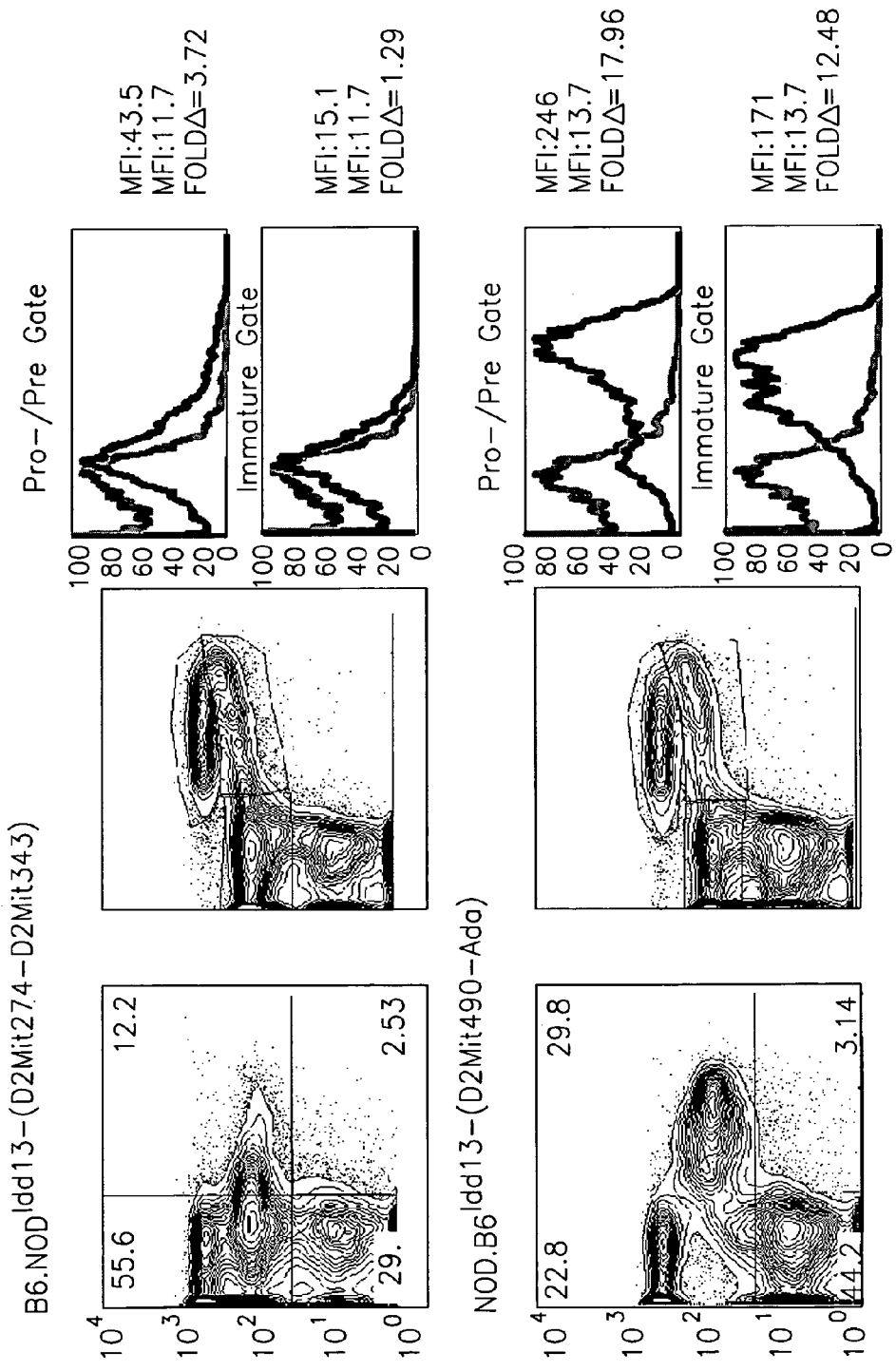
Figure 4B:
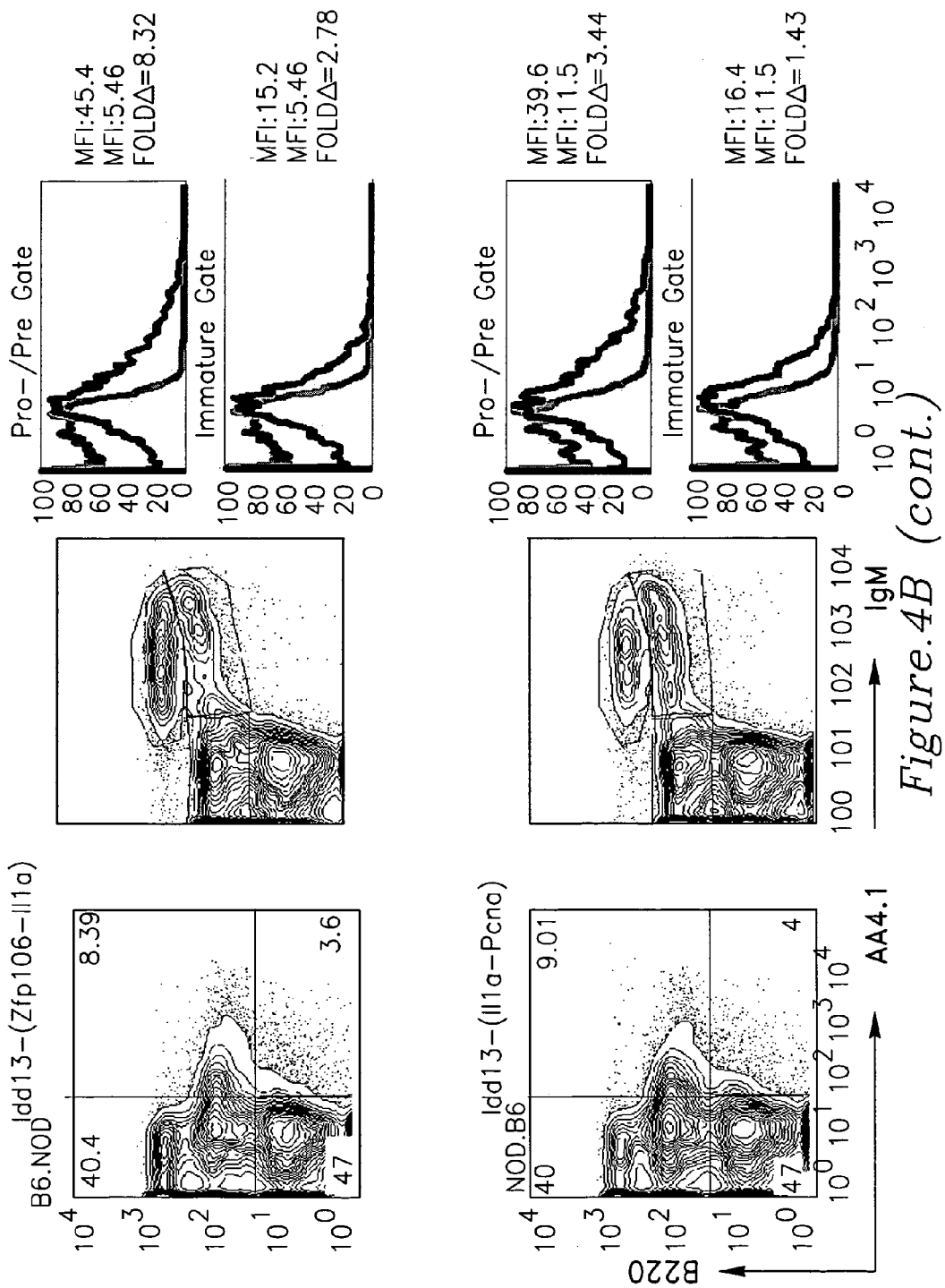

The CD93 gene maps to 84cM on murine chromosome 2 and falls within the NOD Idd13 locus. Idd13 congenic B6 and NOD mice were obtained from Jackson Laboratories in order to establish whether these mice carry the B6 or NOD allele. FIG. 4, Panel A summarizes the chromosomal regions introgressed from either the B6 or NOD strains onto the NOD and B6 backgrounds for each Idd13 congenic strain, respectively. The $B6.NOD^{Idd13}$ strain carries the NOD chromosome 2 from 52.5-84.2 cM. Early B cell progenitors from the $B6.NOD^{Idd13}$ strain are deficient in CD93 expression as compared to B6 wild-type counterparts, similarly to NOD wild-type mice (FIG. 4). Three $NOD.B6^{Idd13}$ sub-congenic mouse lineages (JAX #2346, 3050 and 3051) are currently available from Jackson Laboratories (FIG. 4, Panel A). The $NOD.B6^{Idd13(JAX\ \#2346)}$ strain harbors B6 chromosome 2 in the range of 64.5-94cM and, as such, carries the B6 CD93 allele. Early B cell progenitors in this strain express CD93 similarly to B6 wild-type counterparts (FIG. 4, panel B). On the other hand, $NOD.B6^{Idd13(JAX\ \#3050)}$ and $NOD.B6^{Idd13(JAX\ \#3051)}$ harbor B6 chromosome 2 in the range of 67.2-73 cM and 73-75 cM, respectively. Early B cell progenitors from these Idd13 subcongenic strains are deficient in CD93 expression as compared to B6 wild-type counterparts, similarly to NOD wild-type mice (FIG. 4, panel B).

EXAMPLE 3

Figure 5A:
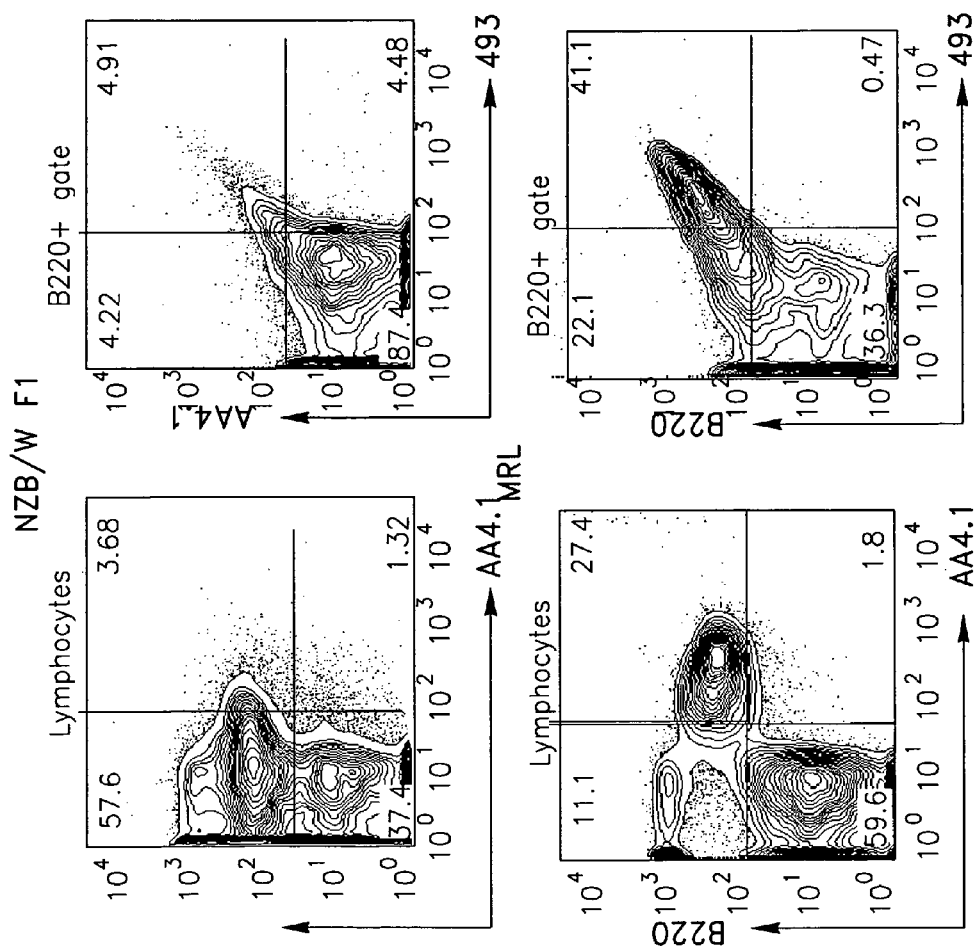
FIGS. 5A-B show CD93 expression by B cell developmental subsets in the BM and periphery of NZB/W F1 and MRL mice.
Figure 5B:
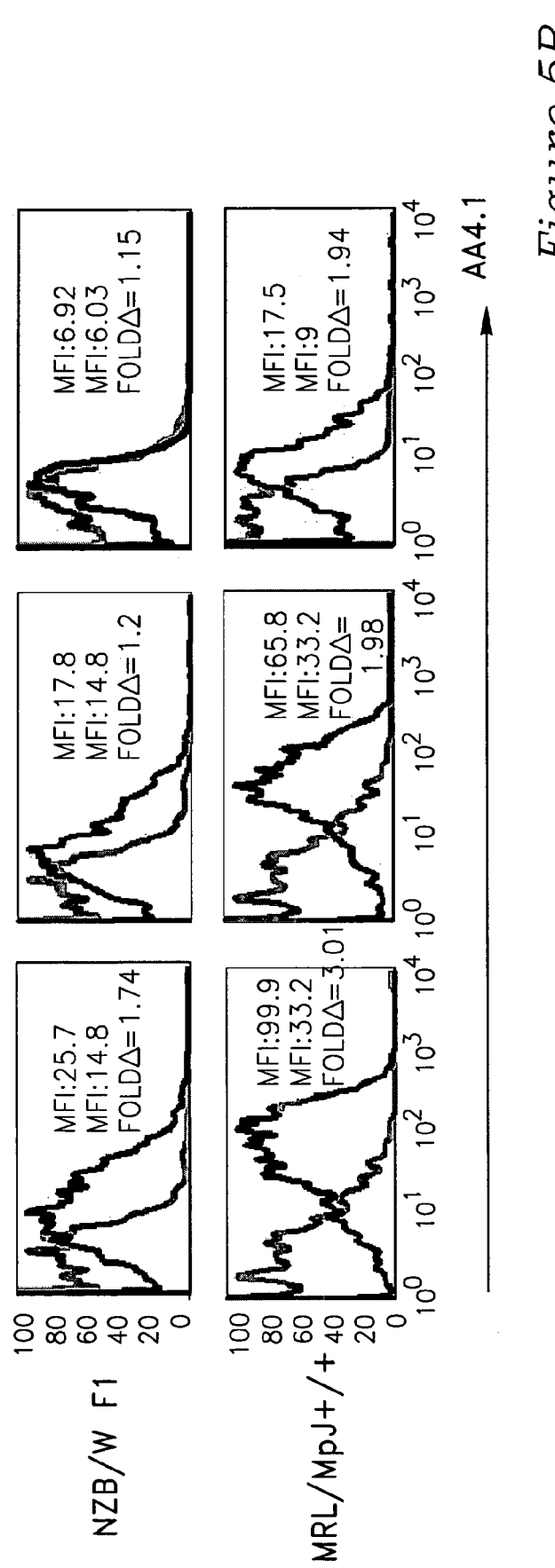

CD93 Expression by Pro-/Pre-, Immature and Transitional B Cells is Deficient in NZB/W F1 Mice Since the Idd13 locus maps to the same region of chromosome 2 as that of the Lupus susceptibility gene(s) in NZBAV F1 mice, termed Wbwl and Nkt2, a determination was sought as to whether NZBAV F1 mice also exhibit a CD93 defect similar to that of NOD mice. NZBAV F1 mice were found to exhibit aberrant CD93 expression on their Pro-/Pre-, Immature and TR B cells (FIG. 5), identical to that of NOD mice. On the other hand, the B cell compartment in lupus-prone MRL mice did not reveal deficient CD93 staining (FIG. 5, panels A and B).

EXAMPLE 4

CD93 Protein is Expressed in Cell Lysates and Serum from NOD and NZB Mice

Figures 6A, 6B:
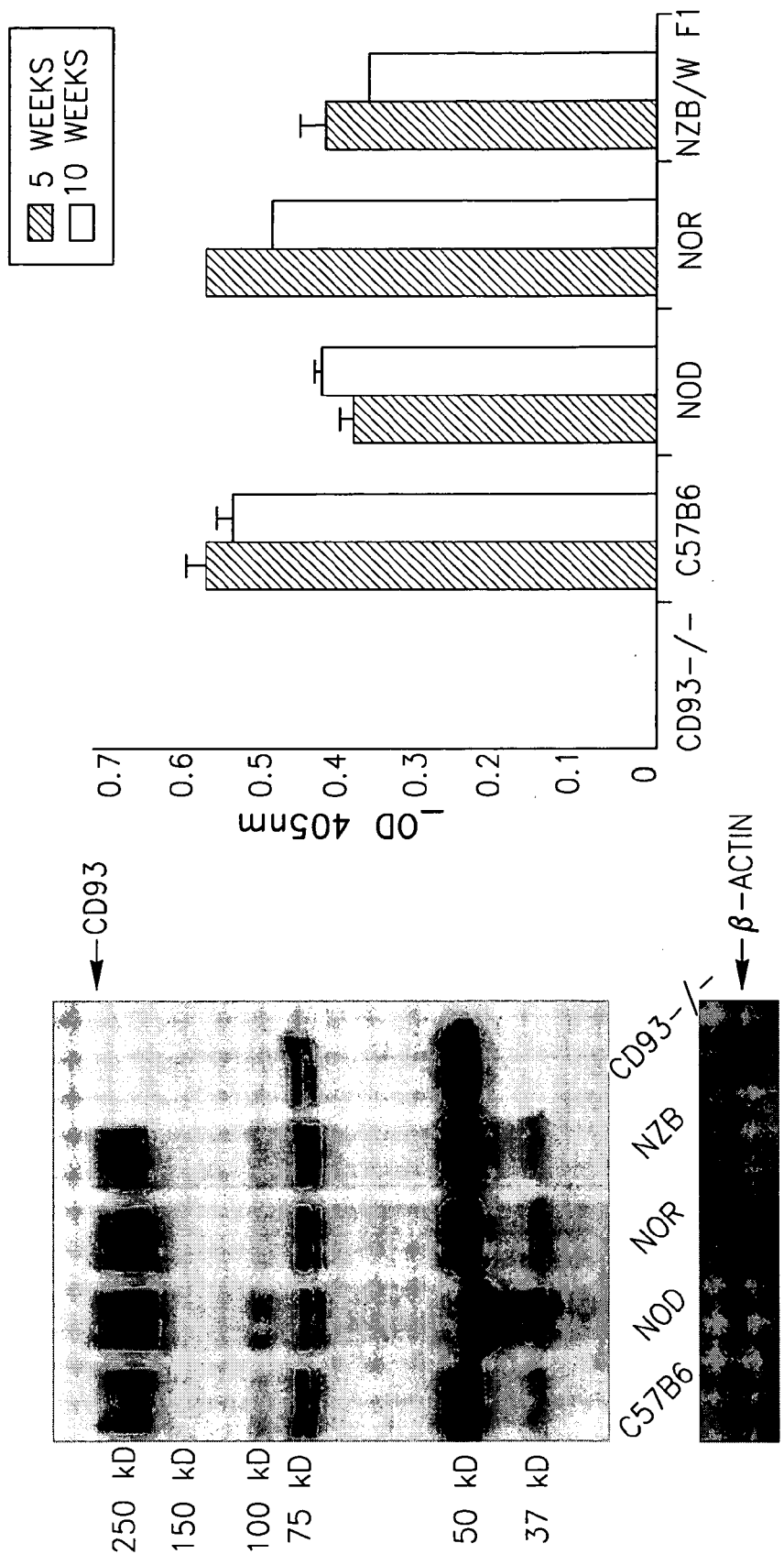
FIGS. 6A-B show CD93 protein is expressed in cell lysates (panel A) and serum (panel B) from NOD and NZB/W F1 mice.

Given the aberrant cell surface expression of CD93 on early B cell progenitors of NOD and NZB/W F1 mice, a determination was sought as to whether the protein is expressed. Lysates from in vitro differentiated, BM derived macrophage lysates were prepared and used in western blot. CD93 protein was detected in both NOD and NZB lysates as assessed using polyclonal anti-CD93 cytoplasmic tail Ab 1150. CD93 bands were seen with NOD and NZB comparable to their respective controls, B6 and NOR (FIG. 6, Panel A). Lysates of BM derived macrophages from the CD93 knock-out were used for a negative control.

CD93 is subject to ectodomain cleavage by metalloproteinase and, as such, exists in soluble form in vivo. Therefore, as another measure of protein expression, serum from NOD and NZB/W F1 mice was assessed for the presence of sCD93 in an ELISA assay. NOD and NZB/W F1 sera contained measurable levels of sCD93, at a slightly lower concentration compared to the control B6 and NOR strains (FIG. 6, panel B). sCD93 levels did not change significantly with age. Additionally, the concentration of sCD93 in NOD mice remained constant for up to 30 weeks of age and no difference was noted between males and females.

EXAMPLE 5

The NOD and NZB/W F1 CD93 Alleles Carry an Asn→His Polymorphism at Amino Scid 264 in its First EGF-Like Domain The aberrant cell surface staining of CD93 on early B cell progenitors in NOD and NZB/W F1 mice using three distinct mAbs, despite the presence of CD93 protein in cell lysates and serum of these mice, suggested a conformational polymorphism. Therefore, a determination was sought as to whether a primary sequence polymorphism(s) may explain this defect in early B cell progenitors.

Genomic CD93 DNA from NOD, MRL, NZBAV F1, B6, and BALB/c was PCR amplified and sequenced using various primers to walk along the amplified DNA. A hitherto unidentified coding polymorphism at cDNA nucleotide position 790, which converts AAC→CAC, was discovered in NOD and NZBAV F1 mice (FIG. 7A). This mutation causes an amino acid substitution from Asn->His at position 264 in the first EGF-like domain of CD93 (FIG. 7, panel B and C). The polymorphism was present in NOD and NZBAV F1 mice, but not in B6, BALB/c, and MRL mice.

EXAMPLE 6

A Subset of CD93−/− Mice Exhibit a Profound State of NKT Cell Deficiency

Figure 8A:
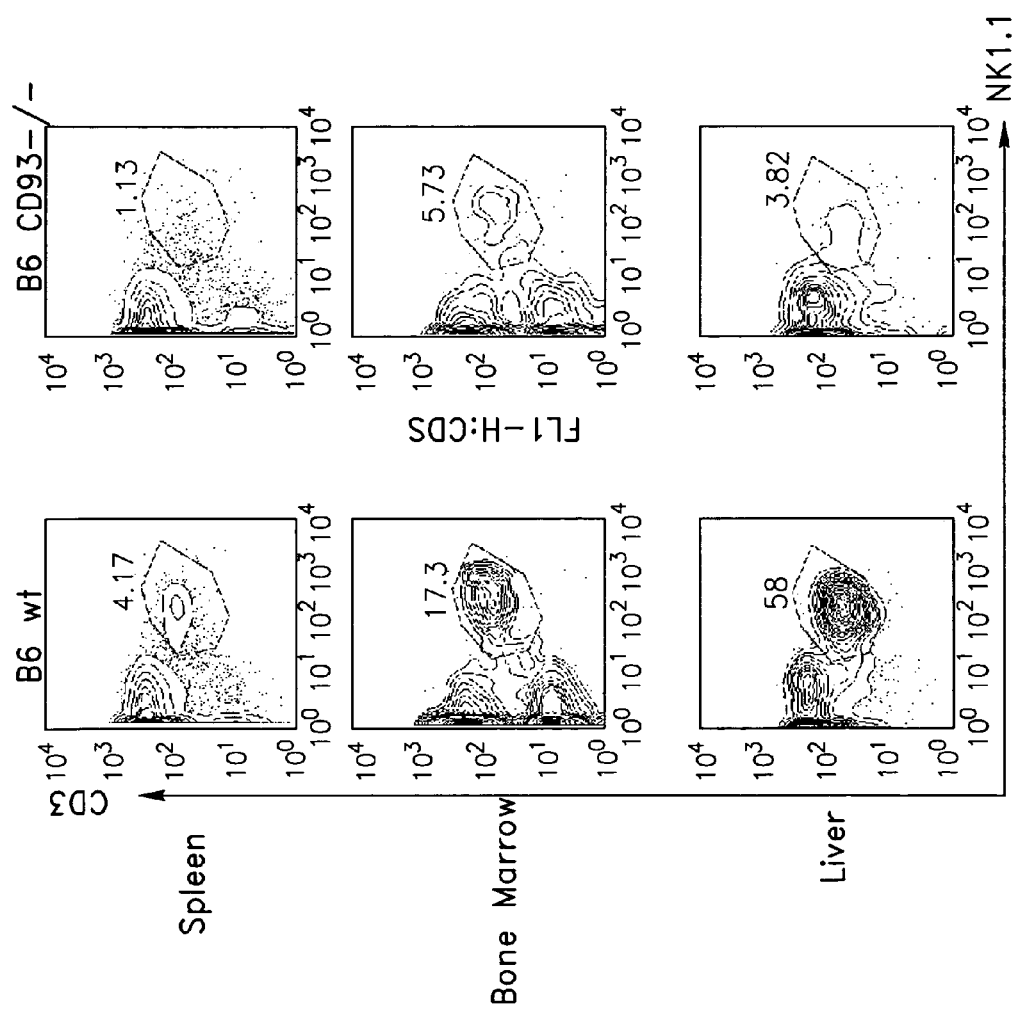
FIG. 8 shows: Panel A) NK1.1 v. CD3 expression in the CD4+ gate in spleen, bone marrow and liver of B6 and B6 CD93−/− mice. Panel B) NK1.1 v. CD3 expression in thymic DN and CD4 SP gate in B6 and B6CD93−/−.
Figure 8B:
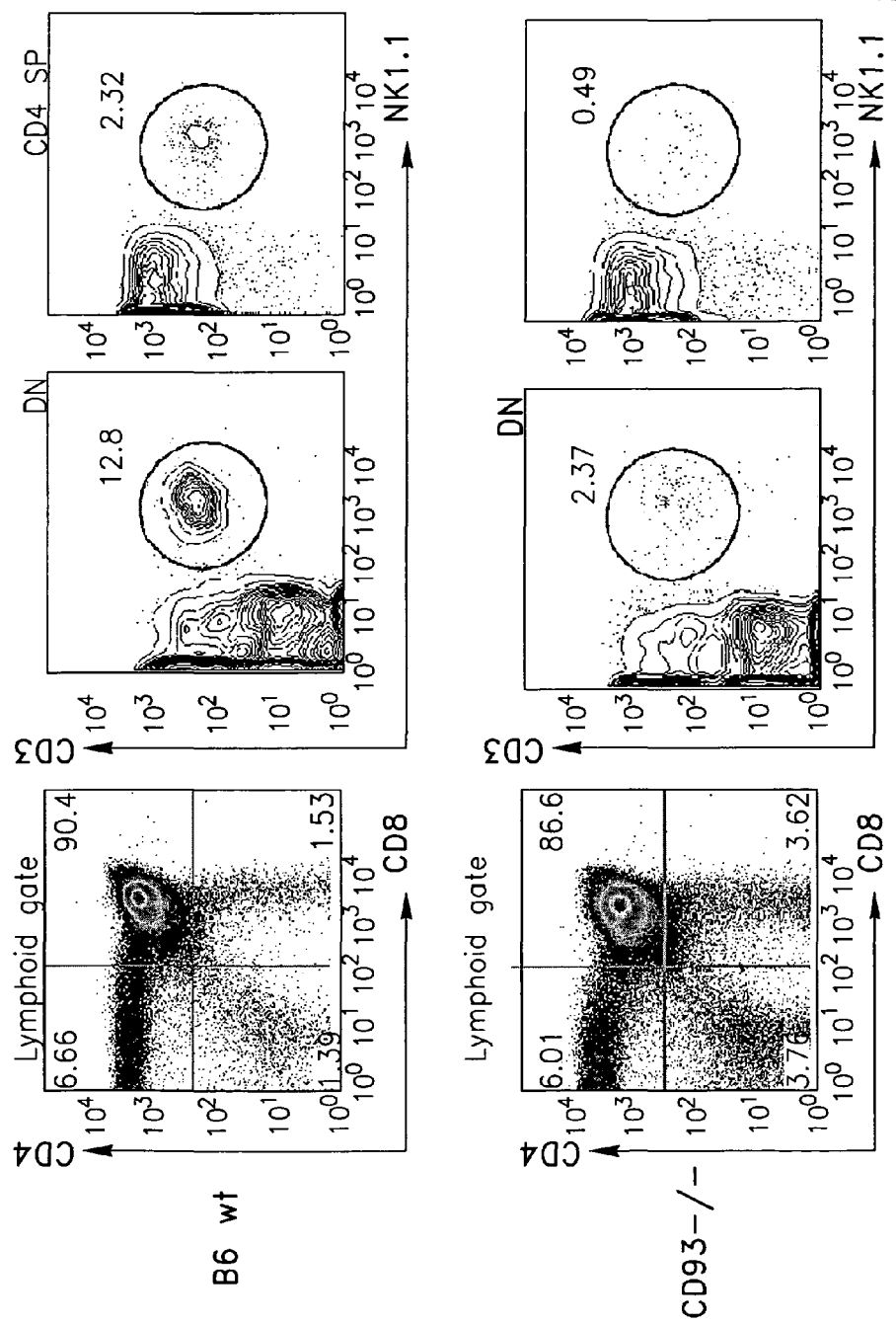
Figure 9A:
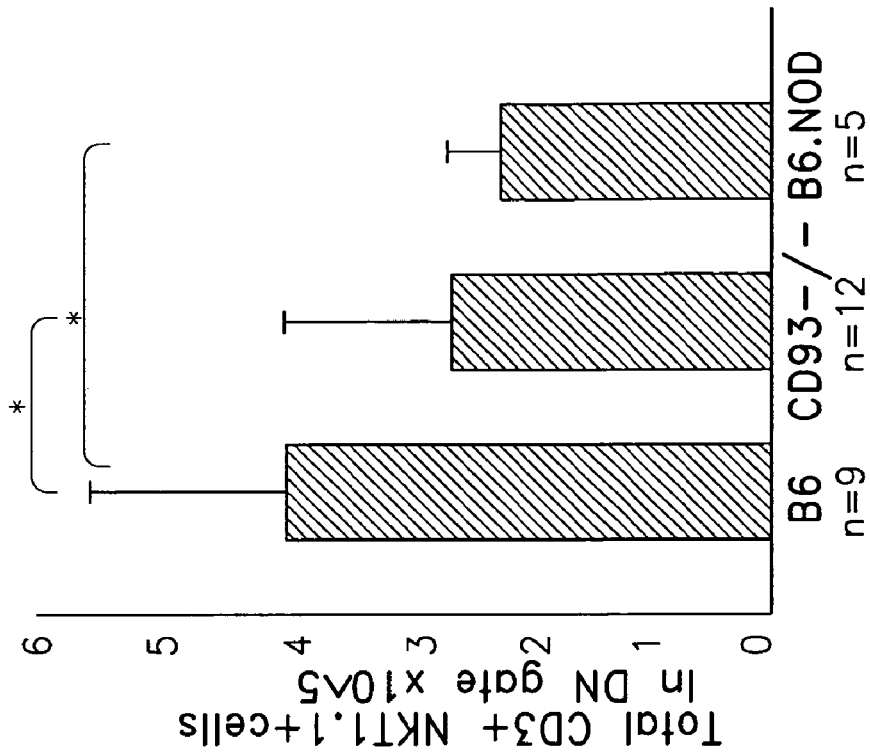
FIG. 9 shows: Panel A) Total CD3+ NK1.1+ cells in the CD4SP gate in the thymus of B6, B6CD93−/− and B6.NODIdd13 mice. Panel B) Total CD3+ NK1.1+ cells in the DN gate in the thymus of B6, B6 CD93−/− and B6.NODIdd13 mice. Panel C) Total CD4+ gated CD3+ NK1.1 cells in the spleen of B6, B6 CD93−/− and B6.NODIdd13 mice. Panel D) Percentage of CD4+ gated CD3+ NK1.1 cells in the liver of B6, B6 CD93−/− and B6.NODIdd13 mice
Figure 9B:
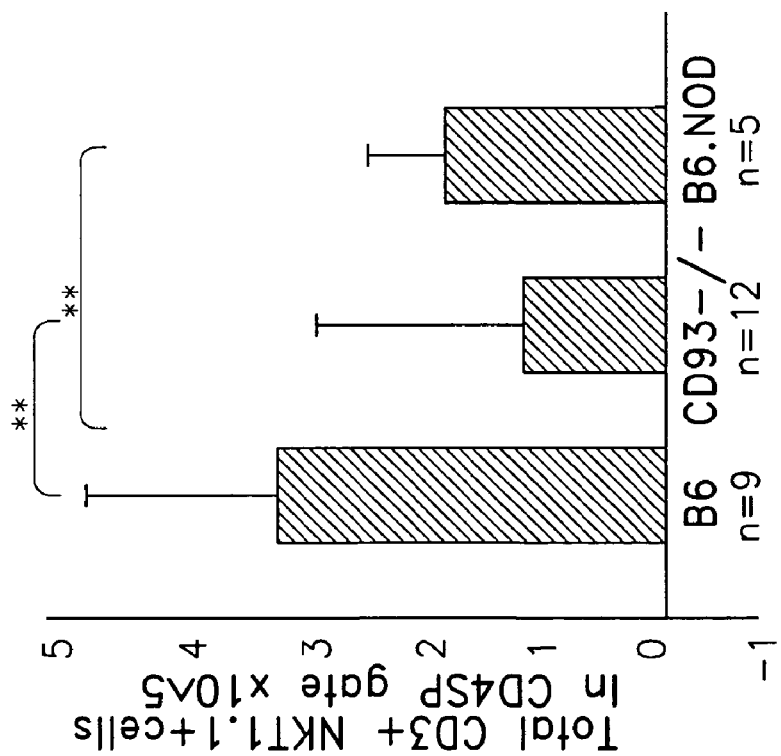

The CD93 locus maps to a region of chromosome 2, which regulates NKT cell function. Therefore, the NKT cell compartment of CD93−/− mice were analyzed in various lymphoid organs including thymus, spleen, lymph nodes, bone marrow and liver. A subset of CD93−/− mice exhibited a profound state of NKT cell deficiency, which was observed in all lymphoid organs analyzed. (See FIG. 8) Overall, CD93−/− mice stratified into two subsets with respect to their NKT cell compartment: 1) NKT cell lymphopenia and 2) a relative decrease in the frequency of NKT cells (See e.g. FIG. 9).

Having described preferred embodiments of the invention with reference to the accompanying drawings and examples, it is to be understood that the invention is not limited to the precise embodiments, and that various changes and modifications may be effected therein by those skilled in the art without departing from the scope or spirit of the invention as defined in the appended claims.

What is claimed is:

1. An isolated nucleic acid molecule encoding a mutated CD93 protein consisting of the amino acid sequence set forth in SEQ ID NO: 4.

2. The isolated nucleic acid of claim 1, wherein said nucleic acid has a nucleotide sequence consisting of the nucleic acid sequence set forth in SEQ ID NO: 3.

3. A vector comprising the nucleic acid molecule of claim 1.

4. A vector comprising the nucleic acid molecule of claim 1, operably linked to a transcriptional promoter.

* * * * *